(12) United States Patent
Eberlin et al.

(10) Patent No.: US 11,737,671 B2
(45) Date of Patent: *Aug. 29, 2023

(54) MINIMALLY INVASIVE COLLECTION PROBE AND METHODS FOR THE USE THEREOF

(71) Applicant: Board of Regents, The University of Texas System, Austin, TX (US)

(72) Inventors: Livia Schiavinato Eberlin, Austin, TX (US); Thomas Milner, Austin, TX (US); Jialing Zhang, Austin, TX (US); Noah Giese, Austin, TX (US); Nitesh Katta, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/453,740

(22) Filed: Nov. 5, 2021

(65) Prior Publication Data

US 2022/0296102 A1 Sep. 22, 2022

Related U.S. Application Data

(63) Continuation of application No. 16/882,801, filed on May 26, 2020, now abandoned, which is a
(Continued)

(51) Int. Cl.
*A61B 5/00* (2006.01)
*H01J 49/04* (2006.01)
(Continued)

(52) U.S. Cl.
CPC .......... *A61B 5/0075* (2013.01); *A61B 1/3132* (2013.01); *A61B 10/02* (2013.01);
(Continued)

(58) Field of Classification Search
CPC ..... A61B 5/0075; A61B 34/30; A61B 1/3132; A61B 10/02; A61B 10/06; A61B 17/34;
(Continued)

(56) References Cited

U.S. PATENT DOCUMENTS

| 5,100,402 A | 3/1992 | Fan |
| 5,152,277 A | 10/1992 | Honda et al. |

(Continued)

FOREIGN PATENT DOCUMENTS

| CN | 201811941 U | 4/2011 |
| CN | 102221614 A | 10/2011 |

(Continued)

OTHER PUBLICATIONS

Zhang et al, "Nondestructive Tissue Analysis for Ex Vivo and In Vivo Cancer Diagnosis Using a Handheld Mass Spectrometry System", Science Translational Medicine, 2017, vol. 9, No. 406 (Year: 2017).*

(Continued)

*Primary Examiner* — David E Smith
(74) *Attorney, Agent, or Firm* — MEUNIER CARLIN & CURFMAN LLC

(57) ABSTRACT

Method and devices are provided for assessing tissue samples from a plurality of tissue sites in a subject using molecular analysis. In certain aspects, devices of the embodiments allow for minimally invasive collection of liquid tissue samples and delivery of the samples for mass spectrometry analysis.

20 Claims, 30 Drawing Sheets

Related U.S. Application Data continuation of application No. PCT/US2018/062625, filed on Nov. 27, 2018.

(60) Provisional application No. 62/640,385, filed on Mar. 8, 2018, provisional application No. 62/591,179, filed on Nov. 27, 2017.

(51) Int. Cl.

| | | |
|---|---|---|
| *H01J 49/16* | (2006.01) | |
| *A61B 34/30* | (2016.01) | |
| *A61B 1/313* | (2006.01) | |
| *A61B 10/02* | (2006.01) | |
| *A61B 17/34* | (2006.01) | |
| *A61M 25/00* | (2006.01) | |
| *G01N 33/483* | (2006.01) | |
| *A61B 90/00* | (2016.01) | |
| *A61B 10/06* | (2006.01) | |

(52) U.S. Cl.
CPC .............. *A61B 17/34* (2013.01); *A61B 34/30* (2016.02); *A61M 25/0026* (2013.01); *G01N 33/4833* (2013.01); *H01J 49/0431* (2013.01); *H01J 49/165* (2013.01); *A61B 10/06* (2013.01); *A61B 2090/395* (2016.02); *A61B 2090/3983* (2016.02)

(58) Field of Classification Search
CPC .............. A61B 2090/395; H01J 49/165; H01J 49/0431
See application file for complete search history.

(56) References Cited

U.S. PATENT DOCUMENTS

| | | | |
|---|---|---|---|
| 5,241,990 A | 9/1993 | Cook | |
| 5,384,260 A | 1/1995 | Osborne et al. | |
| 5,607,389 A | 3/1997 | Edwards et al. | |
| 5,711,816 A | 1/1998 | Kirlin et al. | |
| 5,742,050 A | 4/1998 | Amirav et al. | |
| 5,746,720 A | 5/1998 | Stouder, Jr. | |
| 6,297,499 B1 | 10/2001 | Fenn | |
| 6,534,765 B1 | 3/2003 | Robb et al. | |
| 6,677,593 B1 | 1/2004 | Van Berkel | |
| 6,784,439 B2 | 8/2004 | Van Berkel | |
| 6,803,566 B2 | 10/2004 | Van Berkel | |
| 6,808,510 B1 | 10/2004 | Difiore | |
| 7,295,026 B2 | 11/2007 | Van Berkel et al. | |
| 7,335,897 B2 | 2/2008 | Takats et al. | |
| 7,544,933 B2 | 6/2009 | Cooks et al. | |
| 7,684,934 B2 | 3/2010 | Shvartsburg et al. | |
| 7,847,244 B2 | 12/2010 | Venter et al. | |
| 8,076,639 B2 | 12/2011 | Cooks et al. | |
| 8,084,735 B2 | 12/2011 | Kertesz et al. | |
| 8,203,117 B2 | 6/2012 | Wiseman et al. | |
| 8,207,494 B2 | 6/2012 | Hieftje et al. | |
| 8,314,382 B2 | 11/2012 | Takats | |
| 8,324,570 B2 | 12/2012 | Wiseman et al. | |
| 8,421,005 B2 | 4/2013 | Musselman | |
| 8,604,423 B2 | 12/2013 | Enke et al. | |
| 8,704,167 B2 | 4/2014 | Cooks et al. | |
| 8,710,437 B2 | 4/2014 | Cooks et al. | |
| 8,816,275 B2 | 8/2014 | Ouyang et al. | |
| 8,859,956 B2 | 10/2014 | Ouyang et al. | |
| 8,859,958 B2 | 10/2014 | Ouyang et al. | |
| 8,859,959 B2 | 10/2014 | Ouyang et al. | |
| 8,859,986 B2 | 10/2014 | Cooks et al. | |
| 8,890,063 B2 | 11/2014 | Ouyang et al. | |
| 8,933,398 B2 | 1/2015 | Ouyang et al. | |
| 8,937,288 B1 | 1/2015 | Cooks et al. | |
| 9,024,254 B2 | 5/2015 | Cooks et al. | |
| 9,035,239 B1 | 5/2015 | Cooks et al. | |
| 9,046,448 B2 * | 6/2015 | Takats | A61B 10/02 |
| 9,105,458 B2 | 8/2015 | Trimpin et al. | |
| 9,116,154 B2 | 8/2015 | Ouyang et al. | |
| 9,281,174 B2 | 3/2016 | Takats | |
| 9,297,828 B2 | 3/2016 | Ovchinnikova et al. | |
| 9,305,759 B2 | 4/2016 | Mcewen et al. | |
| 9,500,572 B2 | 11/2016 | Ouyang et al. | |
| 9,538,945 B2 | 1/2017 | Cooks et al. | |
| 9,552,973 B2 | 1/2017 | Mcewen et al. | |
| 9,632,066 B2 | 4/2017 | Van Berkel | |
| 9,700,251 B2 | 7/2017 | Cooks et al. | |
| 10,643,832 B2 * | 5/2020 | Eberlin | G01N 33/6848 |
| 10,943,775 B2 | 3/2021 | Eberlin et al. | |
| 2003/0193020 A1 | 10/2003 | Van Berkel | |
| 2004/0014227 A1 * | 1/2004 | Frederick | G01N 30/24 422/67 |
| 2004/0059530 A1 | 3/2004 | Paulse et al. | |
| 2005/0061967 A1 | 3/2005 | Shvartsburg et al. | |
| 2005/0256424 A1 | 11/2005 | Zimmon | |
| 2006/0169030 A1 | 8/2006 | Stewart et al. | |
| 2006/0292607 A1 | 12/2006 | Caprioli | |
| 2007/0114375 A1 | 5/2007 | Pevsner et al. | |
| 2007/0135779 A1 | 6/2007 | Lalomia et al. | |
| 2007/0197954 A1 | 8/2007 | Keenan | |
| 2008/0156985 A1 | 7/2008 | Venter et al. | |
| 2008/0217524 A1 | 9/2008 | Mawer et al. | |
| 2008/0243141 A1 | 10/2008 | Privitera et al. | |
| 2008/0302957 A1 | 12/2008 | Wang et al. | |
| 2009/0039283 A1 | 2/2009 | Franzen et al. | |
| 2009/0302211 A1 | 12/2009 | Takats | |
| 2010/0148057 A1 | 6/2010 | Jarrell et al. | |
| 2010/0176287 A1 | 7/2010 | Ribbing et al. | |
| 2010/0224013 A1 | 9/2010 | Van Berkel et al. | |
| 2010/0285486 A1 | 11/2010 | Grossman et al. | |
| 2010/0317964 A1 | 12/2010 | Hendriks et al. | |
| 2011/0021451 A1 | 1/2011 | Wenk et al. | |
| 2011/0133077 A1 | 6/2011 | Henion et al. | |
| 2011/0190151 A1 | 8/2011 | Mcmanus et al. | |
| 2011/0250208 A1 | 10/2011 | Frostegaard | |
| 2011/0253889 A1 | 10/2011 | Ishimaru et al. | |
| 2011/0284735 A1 | 11/2011 | Van Berkel et al. | |
| 2012/0053065 A1 | 3/2012 | Van Berkel | |
| 2012/0080592 A1 | 4/2012 | Wiseman et al. | |
| 2012/0083045 A1 | 4/2012 | Van Berkel et al. | |
| 2012/0085903 A1 | 4/2012 | Trimpin | |
| 2012/0149009 A1 | 6/2012 | Levis et al. | |
| 2012/0156712 A1 | 6/2012 | Takats | |
| 2012/0295276 A1 | 11/2012 | Cooks et al. | |
| 2013/0109592 A1 | 5/2013 | Fan et al. | |
| 2013/0115618 A1 | 5/2013 | Swinnen | |
| 2013/0131470 A1 | 5/2013 | Galinkin et al. | |
| 2013/0273560 A1 | 10/2013 | Cooks et al. | |
| 2013/0288355 A1 | 10/2013 | Dewitte et al. | |
| 2014/0179805 A1 | 6/2014 | Stylli | |
| 2014/0216177 A1 | 8/2014 | Van Berkel et al. | |
| 2014/0353488 A1 * | 12/2014 | Takats | G01N 30/7253 250/288 |
| 2015/0008314 A1 | 1/2015 | Sessler et al. | |
| 2015/0076339 A1 | 3/2015 | Fedorov et al. | |
| 2015/0202005 A1 * | 7/2015 | Fuflyigin | A61B 18/20 606/12 |
| 2015/0226745 A1 | 8/2015 | Skotland et al. | |
| 2015/0230738 A1 | 8/2015 | Cooks et al. | |
| 2015/0275298 A1 | 10/2015 | Stylli | |
| 2015/0299808 A1 | 10/2015 | Gonzalez Diaz et al. | |
| 2015/0338413 A1 | 11/2015 | Agar | |
| 2015/0364306 A1 | 12/2015 | Yang et al. | |
| 2016/0041138 A1 | 2/2016 | Pycke et al. | |
| 2016/0047831 A1 | 2/2016 | Cooks et al. | |
| 2016/0168617 A1 | 6/2016 | Yang et al. | |
| 2016/0178629 A1 | 6/2016 | Agar | |
| 2016/0181078 A1 * | 6/2016 | Kovarik | H01J 49/0431 250/424 |
| 2016/0181079 A1 * | 6/2016 | Berkout | H01J 49/0031 250/281 |
| 2016/0194708 A1 | 7/2016 | Wilson | |
| 2016/0296215 A1 | 10/2016 | Bouamrani et al. | |
| 2016/0299041 A1 | 10/2016 | Kertesz et al. | |
| 2016/0314956 A1 | 10/2016 | Cooks et al. | |
| 2016/0341712 A1 * | 11/2016 | Agar | G01N 33/4833 |
| 2017/0014149 A1 | 1/2017 | Nakayashiki et al. | |

(56) References Cited

U.S. PATENT DOCUMENTS

| | | | |
|---|---|---|---|
| 2017/0082604 A1 | 3/2017 | Ouyang et al. | |
| 2017/0097355 A1 | 4/2017 | Raftery et al. | |
| 2017/0248607 A1 | 8/2017 | Cooks et al. | |
| 2017/0284983 A1 | 10/2017 | Jarrold et al. | |
| 2018/0038838 A1 | 2/2018 | Karancsi et al. | |
| 2018/0059119 A1* | 3/2018 | Takáts | A61B 18/20 |
| 2018/0059126 A1 | 3/2018 | Jones et al. | |
| 2018/0067097 A1 | 3/2018 | Eberlin et al. | |
| 2018/0078298 A1* | 3/2018 | Gonzalez | A61B 17/1622 |
| 2018/0144916 A1 | 5/2018 | Richardson et al. | |
| 2018/0158661 A1 | 6/2018 | Eberlin et al. | |
| 2018/0238776 A1* | 8/2018 | Karancsi | A61B 5/0066 |
| 2018/0271502 A1 | 9/2018 | Zarrine-afsar et al. | |
| 2018/0294148 A1 | 10/2018 | Ouyang et al. | |
| 2020/0305723 A1 | 10/2020 | Eberlin et al. | |

FOREIGN PATENT DOCUMENTS

| | | |
|---|---|---|
| JP | 2004000377 A | 1/2004 |
| WO | 2009109879 A2 | 9/2009 |
| WO | 2010114976 A1 | 10/2010 |
| WO | 2015061597 A1 | 4/2015 |
| WO | 2016142689 A1 | 9/2016 |
| WO | 2016142691 A1 | 9/2016 |
| WO | 2018045208 A1 | 3/2018 |
| WO | 2019165351 A1 | 8/2019 |

OTHER PUBLICATIONS

Extended European Search Report and Opinion dated Jul. 27, 2021 in EP 18880750.7.
Extended European Search Report Issued in corresponding European Application No. 17847571.1, dated on Mar. 4, 2020.
International Search Report and Written Opinion issued in corresponding PCT Application No. PCT/US2018/062625, dated Mar. 14, 2019,.
International Search Report and Written Opinion issued in corresponding PCT Application No. PCT/US2019/019371, dated May 13, 2019.
International Search Report and Written Opinion issued in International Application No. PCT/US17/41696 dated Dec. 28, 2017.
International Search Report and Written Opinion issued in International Application No. PCT/US17/49689 dated Jan. 4, 2018.
Invitrogen. Custom Peptide Storage and Dissolution. Jun. 6, 2003 [online] Retrieved from the internet ,URL: http://tools.thermofisher.com/content/sfs/manuals/custompeptide_man.pdf>.
SIGMAALDRICH. Ethanol standards 10% (v/v) Aug. 28, 2017 [online] Retrieved from the Internet <URL: https://www.sigmaaldrich.com/catalog/product/sigma/e2385?lang=en&region=US>.
Azizi, et al., Association of Hashimoto's Thyroiditis with Thyroid Cancer, Endocr. Relat. Cancer, 21:845-852, 2014.
Balasubramanian, et al., Dichotomous roles for externalized cardiolipin in extracellular signaling: Promotion of phagocytosis and attenuation of innate immunity, Sci Signal, 8:1-15, 2015.
Balog, et al., "Intraoperative Tissue Identification Using Rapid Evaporative Ionization Mass Spectrometry", Sci. Transl. Med., 5(194):194ra93, 2013.
Basile, et al., "Analysis of lipids from crude lung tissue extracts by desorption electrospray ionization mass spectrometry and pattern recognition", Anal. Biochem., 408:289-296, 2011.
Bonora, et al., "Defective Oxidative Phosphorylation in Thyroid Oncocytic Carcinoma Is Associated with Pathogenic Mitochondrial DNA Mutations Affecting Complexes I and III", Cancer Res., 66:6087-6096, 2006.
Calligaris, David et al., "Mass spectrometry imaging as a tool for surgical decision-making." Journal of Mass Spectrometry 48.11 (2013): 1178-1187.
Camilleri-Broet, et al., "Distinct alterations in mitochondrial mass and function characterize different models of apoptosis", Erp. Cell Res., 239:277-292, 1998.

Castagna, et al., "Nodules in autoimmune thyroiditis are associated with increased risk of thyroid cancer in surgical series but not in cytological series: evidence for selection bias", J. Clin. Endocrinol. Metab., 99:3193-3198, 2014.
Chang, et al., "Production of multiple cytokines and induction of cachexia in athymic nude mice by a new anaplastic thyroid carcinoma cell line", J. Endocrinol., 179:387-394, 2003.
Chiappetta, et al., "The RET/PTC oncogene is frequently activated in oncocytic thyroid tumors (Hurthle cell adenomas and carcinomas), but not in oncocytic hyperplastic lesions." The Journal of Clinical Endocrinology & Metabolism 87.1 (2002): 364-369.
Chicco, et al., "Role of cardiolipin alterations in mitochondrial dysfunction and disease", Am. J. Physiol. Cell Physiol, 292(1):C33-C44, 2007.
Corrias, et al., "'Thyroid Nodules and Cancer in Children and Adolescents Affected by Autoimmune Thyroiditis", Arch. Pediatrics Adolescent Med., 162(6):526-531, 2008.
Cunha, et al., The crosstalk between thyroid gland and adipose tissue: signal integration in health and disease, J. Thyroid Res., 387062: 1-13, 2011.
De Paepe, , "Mitochondrial markers for cancer: relevance to diagnosis, therapy, and prognosis and general understanding of malignant disease mechanisms", ISRN Pathol., 217162:1-15, 2012.
Dobrinja, et al., "Coexistence of chronic lymphocytic thyroiditis and papillary thyroid carcinoma. Impact on presentation, management, and outcome", Int. J. Surgery, 28:S70-S74. 2016.
Dobrzynska, et al., "Changes in electric charge and phospholipids composition in human colorectal cancer cells", Mot. Cell. Biochem. 276:113-119, 2005.
Dong, LQ et al., "Hashimoto's thyroiditis and papillary carcinoma in an adolescent girl: A case report", Mol. Clin. Oncol., 5:.129-131, 2016.
Doria, et al., "Fatty acid and phospholipid biosynthetic pathways are regulated throughout mammary epithelial cell differentiation and correlate to breast cancer survival", Breast Cancer Res. Treat., 133:635-648) 2012.
Eberlin, et al., "Alteration of the lipid profile in lymphomas induced by MYC overexpression", Proc. Natl. Acad Sci. U.S.A, 111:10450-10455, 2014.
Eberlin, et al., "Classifying human brain tumors by lipid imaging with mass spectrometry", Cancer Res., 72:645-654, 2012.
Eberlin, et al., "Desorption electrospray ionization mass spectrometry for lipid characterization and biological tissue imaging", Biochim. Biophys. Acta, 1811:946-960, 2011.
Eberlin, et al., "Molecular assessment of surgical-resection margins of gastric cancer by mass-spectrometric imaging", Proc. Natl. Acad Sci. USA. 111:2436-2441, 2014.
Ehlers, et al., "Hashimoto's thyroiditis and papillary thyroid cancer: are they immunologically linked?", Trends Endocrinol. Metab., 25:656-664, 2014.
Eriksson, et al., "A genetic variant near olfactory receptor genes influences cilantro preference", PLOS One, 7(e34442):1-8, 2012.
Fatou, et al., "In vivo Real-Time :Mass Spectrometry for Guided Surgery Application." Scientific reports 6 (2016).
Fearon, et al., "Cancer cachexia and fat—muscle physiology", Lancet Oneal., 12:489-495, 2011.
Feider, et al., "Ambient Ionization and FAIMS Mass Spectrometry for Enhanced Imaging of Multiply Charged Molecular Ions in Biological Tissues", Anal. Chem., 88(23): 11533-11541, 2016.
Fernandez, et al., "Early Changes in Intramitochondrial Cardiolipin Distribution during Apoptosis". Cell Growth Differentiation, 13:449-455, 2002.
Fiore, et al., "Iodine, thyroid autoimmunity and cancer", Eur. Thyroid J, 4:26-35, 2015.
Fucikova, et al., "Prognostic and Predictive Value of DAMPs and DAMP-Associated Processes in Cancer", Front. Immunol., 6(402):1-17. 2015.
Fugazzola, et al., "Papillary thyroid carcinoma and inflammation", Front. Endocrinol., 2(88):1-3, 2011.
Galluzzi, et al., "Mitochondrial gateways to cancer", Mol. Aspects Med., 31: 1-20; 2010.

(56) References Cited

OTHER PUBLICATIONS

Gasbarri, et al., "Detection and molecular characterisation of thyroid cancer precursor lesions in a specific subset of Hashimoto's thyroiditis", Br J Cancer, 91(6):1096-1104, 2004.

Gasparre, et al., "Relevance of mitochondrial genetics and metabolism in cancer development", Proc. Natl. Acad Sci., 104:9001-9006, 2007.

Gasparre, et al., "Relevance of mitochondrial genetics and metabolism in cancer development". Cold Spring Harbor Perspect. Biol., 5(a011411):1-19, 2013.

Girod, et al., "Desorption electrospray ionization imaging mass spectrometry of lipids in rat spinal cord", J. Am. Soc Mass Spectrom., 21:1177-1189, 2010.

Giusti, et al., "Fine-Needle Aspiration of Thyroid Nodules: Proteomic Analysis To Identify Cancer Biomarkers", Journal of Proteome Research, vol. 7, No. 9, Sep. 5, 2008 (Sep. 5, 2008), pp. 4079-4088.

Gogvadze, et al., "Targeting mitochondria in fighting cancer", Curr. Pharm. Design, 17:4034-4046, 201 I.

Gonzalez, et al., "Mitochondria, energy and cancer: the relationship with ascorbic acid", J Orthomol. Med., 25:29-38, 2010.

Goonesinghe, et al., "Pro-apoptotic Bid induces membrane perturbation by inserting selected lysolipids into the bilayer", Biochem. J., 387:109-118, 2005.

Gredilla, et al., "Influence of hyper- and hypothyroidism on lipid peroxidation, unsaturation of phospholipids, glutathione system and oxidative damage to nuclear and mitochondrial DNA in mice skeletal muscle", Mol. Cell. Biochem., 221 :41-48, 2001.

Guo, et al., "Significantly increased monounsaturated lipids relative to polyunsaturated lipids in six types of cancer microenvironment are observed by mass spectrometry imaging", Sci. Rep., 4(5959):1-9, 2014.

Guo, et al., "Tissue imaging and serum lipidomic profiling for screening potential biomarkers of thyroid tumors by matrix-assisted laser desorption/ionization—Fourier transform ion cyclotron resonance mass spectrometry", Anal. Bioanal. Chem., 406:4357-4370, 2014.

Han, et al., "Shotgun lipidomics identifies cardiolipin depletion in diabetic myocardium linking altered substrate utilization with mitochondrial dysfunction". Biochemistry, 44:16684-16694, 2005.

Han, et al., "Shotgun lipidomics of cardiolipin molecular species in lipid extracts of biological samples". J Lipid Res., 4 7 :864-879, 2006.

Henry-Mowatt, et al., "Role of mitochondrial membrane permeabilization in apoptosis and cancer", Oncogene, 23:2850-2.860, 2004.

Husain, et al., "Expression of angiogenic switch, cachexia and inflammation factors at the crossroad in undifferentiated thyroid carcinoma with BRAFV600E", Cancer Lett., 380:577-585, 2016.

Ifa, et al., "Ambient ionization mass spectrometry for cancer diagnosis and surgical margin evaluation." Clinical chemistry 62.1 (2016): 111-123.

Igal, et al., "Roles of stearoyl-CoA desaturase-I in the regulation of cancer cell growth, survival and tumorigenesis". Cancers, 3:2462-2477. 2011.

Igal, et al., "Stearoyl-CoA desaturase-1: a novel key player in the mechanisms of cell proliferation, programmed cell death and transformation to cancer", Carcinogenesis, 31: 1509-1515, 2010.

Ishikawa, et al., "Increased expression of phosphatidylcholine (16:0/18:1) and (16:0/18:2) in thyroid papillary cancer", PLoS One. 7(e48873):I-9, 2012.

Iyer, et al., "Rising incidence of second cancers in patients with low-risk (T1N0) thyroid cancer who receive radioactive iodine therapy", Cancer, 117(19):4439-4446, 2011.

Jahnke, et al., "Evidence for Mitochondrial Respiratory Deficiency in Rat Rhabdomyosarcoma Cells", PLOS One, 5(e8637):1-9, 2010.

Jarmusch, et al., "Lipid and metabolite profiles of human brain tumors by desorption electrospray ionization-MS." Proceedings of the National Academy of Sciences 113.6 (2016): 1486-1491.

Kauppila, TJ et al., Effect of the solvent flow rate on the ionization efficiency in atmospheric pressure photoionization-mass spectrometry. Journal of the American Society for Mass Spectrometry. 2005, 16, 1399-1407.

Kiebish, et al., "Cardiolipin and electron transport chain abnormalities in mouse brain tumor mitochondria: lipidomic evidence supporting the Warburg theory of cancer", .J. Lipid Res., 49:2545-2556, 2008.

Konturek, et al., "Coexistence of papillary thyroid cancer with Hashimoto thyroiditis", Langenbeck's Arch. Surgery, 398:389-394, 2013.

Laskin, et al., "Tissue imaging using nanospray desorption electrospray ionization mass spectrometry", Anal. Chem., 84:141-148, 2012.

Li, et al., "In situ biomarker discovery and label-free molecular histopathological diagnosis of lung cancer by ambient mass spectrometry imaging." Scientific reports 5 (2015).

Lutter, et al., "Cardiolipin provides specificity for targeting of tBid to mitochondria", Nature Cell Biol., 2:754-756, 2000.

Maciel, et al., "Liquid chromatography/tandem mass spectrometry analysis of long-chain oxidation products of cardiolipin induced by the hydroxyl radical", Rapid Comm. Mass Spectrom., 25:316-326, 2011.

Massicotte, et al., "Body Composition Variation and Impact of Low Skeletal Muscle Mass in Patients With Advanced Medullary Thyroid Carcinoma Treated With Vandetanib: Results From a Placebo-Controlled Study", J. Clin. Endocrinol. Metab., 98:2401-2408, 2013.

Mejia, et al., "Mammalian Cardiolipin Biosynthesis", Chem. Phys. Lipids, 179:11-16, 2014.

Merchant, et al., "Phospholipid profiles of human colon cancer using 31P magnetic resonance spectroscopy", Int. J Colorectal Dis., 6:121-126, 1991.

Miccoli, et al., "Metabolomics approach to thyroid nodules: A high-resolution magic-angle spinning nuclear magnetic resonance-based study", Surgery, 152: 1118-1124, 2012.

Mimezami, et al., "Chemical mapping of the colorectal cancer microenvironment via MALDI imaging mass spectrometry (MALDI—MSI) reveals novel cancer-associated field effects", Mol. Oncol., 8:39-49, 2014.

Montero, et al., "Cholesterol and Peroxidized Cardiolipin in Mitochondrial Membrane Properties, Permeabilization and Cell Death", Biochim. Biophys. Acta, 1797:1217-1224, 2010.

Morton, et al., "Alteration of mitochondrial function and lipid composition in Morris 7777 hepatoma", Cancer Res., 36:3246-3254, 1976.

Murke, et al., "The mitochondrial phospholipid cardiolipin is involved in tile regulation of T-cell proliferation", Biochim. Biophys. Acta, 1861:748-754, 2016.

Muscaritoli, et al., "The Ubiquitin/Proteasome System in Cancer Cachexia", In: Cachexia and Wasting: A Modern Approach, Mantovani G. et al. (eds), Springer, Milano, pp. 503-508. 2006.

Nicolson, , "Lipid replacement therapy: a nutraceutical approach for reducing cancer-associated fatigue and the adverse effects of cancer therapy while restoring mitochondrial function", Cancer Metastasis Rev., 29:543-552, 2010.

Nicolson, , "Mitochondrial Dysfunction and Disease: Loss of Mitochondrial Function in Chrome Diseases and its Reversal with Lipid Replacement Therapy", Public Health Alert, pp. 1-8, 2012.

Novais, , "Cardiolipin Content in PI9 Embryonal Carcinoma Cells", 'Thesis presented at the University of Coimbra 112 pages, 2014.

Nygren, et al., "Bioimaging TOF-SIMS: High resolution 3D imaging of single cells", Microscopy Res. Tech., 70(11):969-974, 2007.

Pagni, et al., "Proteomics in thyroid cytopathology: Relevance of MALDI-imaging in distinguishing malignant from benign lesions", Proteomics, vol. 16, No. 11-12, Jun. 1, 2016 (Jun. 1, 2016), pp. 1775-1784.

Pagni, et al., "Proteomics for the diagnosis of thyroid lesions: preliminary report", Cytopathology, vol. 26, No. 5, Jul. 20, 2014 (Jul. 20, 2014), pp. 318-324.

Pathak, et al., "Tafazzin protein expression is associated with tumorigenesis and radiation response in rectal cancer: a study of Swedish clinical trial on preoperative radiotherapy", PLoS One, 9(e98317):1-8, 2014.

(56) References Cited

OTHER PUBLICATIONS

Pieczenik, et al., "Mitochondrial Dysfunction and Molecular Pathways of Disease", Exper. Mol. Pathol., 83:84-92, 2007.
Sandra, et al., "Related Apoptosis-Inducing Ligand-Tumor Necrosis Factor", Cancer Res., 65:8286-8297, 2005.
Sapandowski, et al., "Cardiolipin composition correlates with prostate cancer cell proliferation." Molecular and cellular biochemistry 410.1-2 (2015):175-185.
Schild, et al., "Composition of molecular cardiolipin species correlates with proliferation of lymphocytes", Exp. Biol. Med., 237:372-379, 2012.
Schlame, et al., "Microanalysis of cardiolipin in small biopsies including skeletal muscle from patients with mitochondrial disease", .J. Lipid Res .. 40: 1585-1592, 1999.
Schlumberger, et al., "Radioactive iodine treatment and external radiotherapy for lung and bone metastases from thyroid carcinoma." The Journal of Nuclear Medicine 37.4 (1996): 598.
Scott, et al., "Mass spectrometry imaging enriches biomarker discovery approaches with candidate mapping", Health, Phys., 106:120-128, 2014.
Seyfried, et al., "Cancer as a metabolic disease", Nutrition Metab., 7(7): 1-2, 2010.
Shimma, et al., "MALDI-based imaging mass spectrometry revealed abnormal distribution of phospholipids in colon cancer liver metastasis", .J. Chromatogr. B, 855:98-103, 2007.
Shiono, et al., "An analysis of the relationship between metastases and cachexia in lung cancer patients", Cancer Med., 5:2641-2648, 2016.
Shroff, et al., "MYC oncogene overexpression drives renal cell carcinoma in a mouse model through glutamine metabolism", Proc. Natl. Acad. Sci. USA, 112:6539-6544, 2015.
Smith, et al., "Animal and human studies with the mitochondria-targeted antioxidant MitoQ". Ann NY Acad. Sci., 1201:96-103, 2010.
Sotgia, et al., "Mitochondrial oxidative stress drives tumor progression and metastasis: should we use antioxidants as a key component of cancer treatment and prevention?". BMC Med., 9(62) 1-5, 2011.
Tsuchiya, et al., "Cluster Composition Distributions of Pure Ethanol: Influence of Water and Ion-Molecule Reactions Revealed by Liquid-Ionization Tandem Mass Spectrometry", Mass Spectrom., 2(2):A0015, 2013.
Watrous, et al., "Metabolic profiling directly from the Petri dish using nanospray desorption electrospray ionization imaging mass spectrometry". Anal. Chem., 85: 10385-10391, 2013.
Wojakowska, et al., "Application of Metabolomics in Thyroid Cancer Research", Int J. Endocrinol, 2015(258763): 1-13, 2015.
Wojakowska, et al., "Detection of metabolites discriminating subtypes of thyroid cancer: Molecular profiling of FFPE samples using the GC/MS approach", Molecular and Cellular Endocrinology, vol. 417, Sep. 28, 2015 (Sep. 28, 2015), pp. 149-157.
Yang, et al., "Mitochondrial dysregulation and protection in cisplatin nephrotoxicity", Arch. Toxicol., 88:1249-1256, 2014.
Yin, et al., "Free radical oxidation of cardiolipin: chemical mechanisms, detection and implication in apoptosis, mitochondrial dysfunction and human diseases", Free Rad. Res., 46:959-974, 2012.
Zeviar, et al., "The role of mitochondria in cancer and other chronic diseases", .J. Orthomol. Med., 29:157-166, 2014.
Zhang, et al., "Cardiolipins a:re biomarkers of mitochondria-rich thyroid oncocytic tumors", Cancer research, 76(22):6588-6597, 2016.
Zhang, J et al., Nondestructive tissue analysis for ex vivo and in vivo cancer diagnostics using a handheld mass spectrometry system. Science transnational medicine. 2017, 9(406), eean3968.
Zimmermann, et al., "Lack of complex I is associated with oncocytic thyroid tumours", Br. J Cancer, 100:1434-1437, 2009.
Zosin, et al., "Some clinical aspects in chronic autoimmune thyroiditis associated with thyroid differentiated cancer", Maedica, 7:277-283, 2012.

\* cited by examiner

MINIMALLY INVASIVE COLLECTION PROBE AND METHODS FOR THE USE THEREOF

This application is a continuation of U.S. application Ser. No. 16/882,801 filed May 26, 2020, which is a continuation of International Application No. PCT/US2018/062625 filed Nov. 27, 2018, which claims the benefit of U.S. Provisional Patent Application Nos. 62/591,179, filed Nov. 27, 2017 and No. 62/640,385, filed Mar. 8, 2018, each of which are incorporated herein by reference in their entirety.

This invention was made with government support under Grant No. R00CA190783 awarded by the National Institutes of Health. The government has certain rights in the invention.

BACKGROUND OF THE INVENTION

1. Field of the Invention

The present invention relates generally to the field of medicine, molecular biology and biochemistry. More particularly, it concerns methods and devices for assessment of tissue samples using mass spectrometry.

2. Description of Related Art

Clinical diagnosis is commonly performed through the evaluation of tissue samples pre-operatively, intra-operative, and post-operatively, at several other stages of the patient's treatment process. Tissue evaluation is very critical in the diagnosis and management of cancer patients. Intra-operative pathologic assessment of excised tissues, for example, is routinely performed for diagnosis and surgical margin evaluation in a variety of cancer surgeries. The resected tissue specimens are sent to a nearby room, often called the "frozen room", for tissue preparation, staining, and evaluation. The tissue specimen is frozen, sectioned, stained, and interrogated using light microscopy by an expert pathologist who carefully evaluates if the surgical margins contain cancer cells (positive margin) or not (negative margin). While intraoperative frozen section analysis has been performed in clinical practice for decades, it presents many challenges. Freezing artifacts occur during tissue processing and interfere with tissue structure and cell morphology, thus complicating pathologic interpretation, causing the analysis to be unreliable and subjective. Moreover, certain tumor cells are very difficult to recognize due to their atypical pattern of growth and shape. Molecular approaches could provide highly accurate and potentially real-time assessments of tissue samples. Coupling the molecular approaches with minimally invasive surgical techniques, or non-invasive techniques could provide a highly accurate, yet low trauma, way to assess and diagnose tissue and surgical samples. However, to date, adequate devices or methodologies have not been developed that provide effective molecular assessment of tissue samples.

SUMMARY OF THE INVENTION

In a first embodiment there is provided a method for obtaining a mass spectrometry profile comprising using a probe to apply a fixed or discrete volume of a solvent to an assay site (e.g., a tissue site); using the probe to collect the applied solvent to obtain a liquid sample; and subjecting the liquid sample to mass spectrometry analysis. In further embodiment a method is provided for assessing tissue samples comprising obtaining a plurality of liquid samples from a plurality of tissue sites in a subject and subjecting the plurality of liquid samples to mass spectrometry.

Still a further embodiment provides an apparatus for obtaining or producing samples (e.g., from tissues) for mass spectrometry analysis, the apparatus comprising: a chamber comprising a solvent; a gas supply (e.g., a pressurized gas supply); a mass spectrometer; a probe comprising a reservoir, a first conduit, a second conduit and a third conduit, wherein: the reservoir is in fluid communication with the first conduit, the second conduit and the third conduit; the first (solvent) conduit is in fluid communication with the chamber; the second (gas) conduit is in fluid communication with a gas supply; and the third (collection) conduit is in fluid communication with the mass spectrometer. In some aspects, the gas supply can be a pressurized gas supply. In some aspects, the probe is, or is comprised in, the cannula of a surgical instrument. In further aspects, the surgical instrument may be a laparoscope, trocar needle, biopsy guide, or multiple-lumen catheter. In certain aspects, the surgical instrument manually operated. In other aspects, the surgical instrument is robotic.

In yet still further aspects, the probe comprises a distal probe end and the distal probe end comprises a shutter that can be closed to prevent fluid communication outside of the probe. In some aspects, the shutter is a balloon that can be inflated to prevent fluid communication outside of the probe. In certain aspects, the balloon can be inflated with a gas or a liquid. In specific aspects, the shutter is a door that can be closed to prevent fluid communication outside of the probe. In other aspects, the shutter is configured such that is can be opened and closed multiple times. The shutter may be controlled manually or robotically. In several aspects, the first, second or third conduit is more than 1 meter in length. In additional aspects, the first conduit is in fluid communication with the third conduit; and the second conduit is in fluid communication with the third conduit. In further specific aspects, the first conduit is disposed within the third conduit. In other aspects, the second conduit is disposed within the third conduit.

In certain specific aspects, the first conduit and the second conduit are disposed within the third conduit. In further aspects, the first conduit comprises a first distal end; the second conduit comprises a second distal end; the third conduit comprises a third distal end; and the first distal end and the second distal end are located within the third conduit. In some aspects, the third distal end is located within the probe. In another aspect, the first distal end is located a first distance from the distal probe end; the second distal end is located a second distance from the distal probe end; the third distal end is located a third distance from the distal probe end; the first distance is greater than the third distance; and the second distance is greater than the third distance. In an additional aspect, the first distal end and the second distal end terminate proximal to a sample collection region of the third conduit. In certain aspects, the sample collection region is located between the first and second distal ends and the third distal end. In further specific aspects, the sample collection region is in fluid communication with the mass spectrometer via the third conduit. In some additional aspects, the apparatus further comprises a control system configured to control; a solvent flow from the chamber through the first conduit to the first distal end; a gas flow from the gas supply through the second conduit to the second distal end; and a sample flow through the third conduit to the mass spectrometer.

In yet still further aspects, the apparatus may additionally comprise a fourth conduit, wherein the first conduit, the second conduit and the third conduit are each in fluid communication with the fourth conduit. In some aspects, the apparatus may further comprise a first valve configured to control flow between the first conduit and the fourth conduit; and a second valve configured to control flow between the second conduit and the fourth conduit. In an additional aspect, the apparatus may further comprise a third first valve configured to control flow between the third conduit and the fourth conduit. In still additional aspects, the gas supply provides air, nitrogen or carbon dioxide to the probe. In certain aspects, the gas supply is a pressurized gas supply that provides a gas to the probe at a pressure between 0.1 psig and 5.0 psig. In other aspects, the pressurized gas supply provides a gas to the probe at a pressure between 0.5 psig and 2.5 psig. In specific aspects, the pressurized gas supply provides a gas to the probe at a pressure less than 100 psig. In some aspects, the gas for use in an apparatus of the embodiments may be provided by a pressurized gas supply. In further aspects, the gas can be pumped into an apparatus. Likewise, in some aspects, the gas can be pulled through an apparatus by use of a vacuum. In some aspects, the vacuum is provided by the mass spectrometer inlet. In further aspects, an additional vacuum system is employed. In certain aspects wherein the apparatus is used for a laparoscopic procedure, the gas supply is preferably a pressurized gas supply.

In some aspects, the solvent comprises water. In more specific aspects, the solvent comprises sterile water. In several aspects, the solvent comprises ethanol. In certain specific aspects, the solvent comprises an aqueous mixture including from 1 to 25% ethanol.

In still further aspects, the probe comprises a tracking device or dye to track a location of the probe. In additional aspects, the apparatus may further comprise a control system configured to control: a solvent flow from the chamber through the first conduit; a gas flow from the gas supply through the second conduit; and a sample flow through the third conduit to the mass spectrometer. In some aspects, the control system is configured to: control the solvent flow at a flow rate between 200 and 5000 microliters per minute for a period of time between 1 and 3 seconds; control the gas flow at a flow rate between 0.1 and 15 psig for a period of time between 5 and 50 seconds; and/or control the sample flow for a period of time between 5 and 50 seconds. In certain aspects, the control system comprises programing that initiates solvent flow.

In additional aspects, the mass spectrometer is in electronic communication with a computer that can provide sample analysis. In some aspects, the computer provides a visual or auditory read-out of the sample analysis. In further aspects, the apparatus may additionally comprise a waste container in fluid communication with the third conduit. In certain aspects, the apparatus may further comprise a valve configured to diverge a fluid from the third conduit to the waste container. In other aspects, the apparatus may further comprise a pump configured to remove contents of the waste container. In still further aspects, the apparatus may comprise a pump in fluid communication with the third conduit. In some aspects, the pump is configured to increase the velocity of the contents within the third conduit. In several aspects, the apparatus may further comprise a heating element coupled to the third conduit. In a specific aspect, the heating element is a heating wire.

In yet still further aspects, the apparatus may comprise an ionization device in fluid communication with the third conduit. In certain aspects, the ionization device is an electrospray ionization (ESI) device. In other aspects, the ionization device is an atmospheric pressure chemical ionization (APCI) device. In some aspects, the ionization device is to form a spray proximal to an inlet for mass spectrometer. In several aspects, the third conduit is not directly coupled to the mass spectrometer. In specific aspects, the apparatus may further comprise a venturi device in fluid communication with the third conduit. In certain aspects, the apparatus does not include device for application of ultrasonic or vibrational energy.

In a further embodiment there is provided a method for assessing tissue samples from a subject comprising (a) applying a fixed or discrete volume of a solvent to a tissue site in the subject through the cannula of a surgical instrument; (b) collecting the applied solvent to obtain a liquid sample; and (c) subjecting the sample to mass spectrometry analysis. In some aspects, the fixed or discrete volume of a solvent is not applied as a spray. In other aspects, the fixed or discrete volume of a solvent is applied as a droplet. In certain aspects, the surgical instrument is a laparoscope, trocar needle, or biopsy guide. The surgical instrument may be manually operated or robotic.

In further aspects, the cannulas comprised in a probe having a distal probe end and the distal probe end comprises a shutter that can be closed to prevent fluid from passing out of the cannula of the probe. In some aspects, the shutter is a balloon that can be inflated to prevent fluid communication outside of the probe. In specific aspects, the balloon can be inflated with a gas. In certain aspects, the shutter is a door than can be closed to prevent fluid communication outside of the probe. For example, the shutter can be an iris diaphragm, a mechanical closure, gate, or tapenade. In some aspects, the shutter can be manually controlled or may be automated. For example, in some aspects, the shutter may be on a timer that activates the shutter after solvent has been in contact with the tissue site for a predetermined time period (e.g., at least about 1, 2, or 3 seconds). In still further aspects, the fixed or discrete volume of a solvent is applied at using a pressure of less than 100 psig. In other aspects, the fixed or discrete volume of a solvent is applied at using a pressure of less than 10 psig. In some aspects, the fixed or discrete volume of a solvent is applied using a mechanical pump to move the solvent through a solvent conduit. In certain aspects, collecting the applied solvent comprises applying a negative pressure to pull the sample into a collection conduit and/or applying a gas pressure to push the sample into a collection conduit. In other aspects, collecting the applied solvent comprises applying a negative pressure to pull the sample into a collection conduit and applying a positive pressure to push the sample into a collection conduit. In certain specific aspects, the solvent is applied through a solvent conduit that is separate from the collection conduit. In further aspects, the gas pressure is applied through a gas conduit that is separate from the solvent conduit and the collection conduit. In still other aspects, applying a gas pressure to push the sample into a collection conduit comprises applying a pressure of less than 100 psig.

In yet still further aspects, the method produces no detectable physical damage to the tissue. In some aspects, the method does not involve application of ultrasonic or vibrational energy to the tissue. In certain aspects, the solvent may be sterile. In specific aspects, the solvent may be a pharmaceutically acceptable formulation, and further an aqueous solution, and still further sterile water. In further specific aspects, the solvent consists essentially of water. In other aspects, the solvent comprises from about 1 to 20% of an alcohol. In some aspects, the alcohol comprises ethanol. In still additional aspects, the discrete volume of solvent is between about 0.1 and 100 μL. In certain aspects, the discrete volume of solvent is between about 1 and 50 μL. In further aspects, collecting the applied solvent is between 0.1 and 30 seconds after the applying step. In another aspect, collecting the applied solvent is between 1 and 10 seconds after the applying step. In some aspects, the tissue site in an internal tissue site that is being surgically assessed.

In still further aspects, the method additionally comprises collecting a plurality liquid samples from a plurality of tissue sites. In certain aspects, the liquid samples are collected with a probe. In specific aspects, the probe is washed between collection of the different samples. In some aspects, the probe is disposable and is changed between collection of the different samples. In another aspect, the probe comprises a collection tip and further comprising ejecting the collection tip from the probe after the liquid samples are collected. In further aspects, the plurality of tissue sites comprises 2, 3, 4, 5, 6, 7, 8, 9 or 10 tissues sites. In an additional aspect, the plurality of tissue sites surrounds a section of tissue that has been surgically resected. In some aspects, the resected tissue is a tumor. In other aspects, the method is further defined as an intraoperative or post operative method. In certain aspects, the mass spectrometry comprises ambient ionization MS. In certain specific aspects, subjecting the sample to mass spectrometry analysis comprises determining a profile corresponding to the tissue site. In a further aspect, the method comprises comparing the profile to a reference profile to identify tissue sites that include diseased tissue. Still a further aspect comprises resecting tissue sites that are identified to include diseased tissue. In another aspect, the method is performed using an apparatus in accordance with the embodiments and aspects described above.

In further aspects, the mass spectrometer is in communication with a computer that provides a sample analysis. In certain aspects, the results of each sample analysis are provided by a visual or auditory output from the computer. For example, the results of each sample analysis by the computer can be indicated by a differently colored light that is illuminated or by a different frequency of sound produced. In some aspects, the mass spectrometer is a mobile the mass spectrometer. In further aspects, the mass spectrometer can comprise an uninterruptable power supply (e.g., a battery power supply). In still further aspects, the mass spectrometer comprises an inlet that may be closed to keep instrument vacuum. In yet further aspects, the mass spectrometer is separated from the probe by a mesh filter (e.g., to block contamination).

In some aspects, the reservoir is configured to form a droplet of the solvent. In certain aspects, the pressurized gas supply provides a gas to the probe at a pressure between 0.1 psig and 5.0 psig. In further aspects, the pressurized gas supply provides a gas to the probe at a pressure between 0.5 psig and 2.5 psig. In several aspects, the pressurized gas supply provides air to the probe. In other aspects, the pressurized gas supply provides an inert gas such as nitrogen or carbon dioxide to the probe. In some aspects, a gas supply for use according to the embodiments is at atmospheric pressure. For example, the conduit for delivery of gas may be supplied by the atmosphere around the apparatus.

In additional aspects, the apparatus further comprises a pump configured to transfer the solvent from the chamber to the first conduit. In further aspects, the apparatus may comprise a first valve configured to control a flow from the third conduit to the mass spectrometer. In some aspects, the third conduit is under a vacuum when the first valve is in the open position. In other aspects, the apparatus may comprise a second valve configured to control a flow of gas (e.g., pressurized gas) through the second conduit.

In certain aspects, the solvent may comprise water and/or ethanol. In several aspects, the probe is formed from polydimethylsiloxane (PDMS) and/or polytetrafluoroethylene (PTFE). In some aspects, the probe is disposable. In particular aspects, the probe may include a collection tip that is ejectable (e.g. capable of being ejected from the probe). In further aspects, the probe comprises a tracking device configured to track a location of the probe. In some aspects, the reservoir has a volume between 1 microliter and 500 microliters, between about 1 microliter and 100 microliters or between about 2 microliters and 50 microliters. In additional aspects, the reservoir has a volume between 5.0 microliters and 20 microliters.

In still further aspects, the apparatus may additionally comprise a control system configured to control: a solvent flow (e.g., flow of a fixed or discrete volume of solvent) from the chamber through the first conduit to the reservoir; a gas flow from the gas supply through the second conduit to the reservoir; and a sample flow from the reservoir through the third conduit to the mass spectrometer. In some aspects, the control system is configured to: control the solvent flow at a flow rate between 100 and 5000 microliters per minute (e.g., between 200 and 400 microliters per minute) for a period of time between 1 and 3 seconds; control the gas flow at a flow rate between 1 and 10 psig for a period of time between 10 and 15 seconds; and control the sample flow for a period of time between 10 and 15 seconds. For example, in some aspects, the control system comprises a trigger or button to initiate solvent flow. In further aspects, the control system comprises a pedal (i.e., that can be operated by foot action) to initiate solvent flow. A skilled artisan will recognize that the lengths of the first and/or second conduit may be adjusted to fit the particular use of the system. In yet further aspects, the control system is configured to control: a solvent flow (e.g., flow rate for a fixed period of time) from the chamber through the first conduit to the reservoir. In further aspects, an apparatus of the embodiments does not include a device for producing ultrasonic or vibrational energy (e.g., in sufficient amounts to disrupt tissues).

A further embodiment provided a method for assessing tissue samples from a subject comprising applying a solvent to a tissue site on the subject, collecting the applied solvent to obtain a liquid sample, and subjecting the sample to mass spectrometry analysis. In certain aspects, the solvent may be sterile. In some aspects, the solvent is pharmaceutically acceptable formulation. In specific aspects, the solvent is an aqueous solution. For example, the solvent may be sterile water or consist essentially of water. In other aspects, the solvent may comprise from about 1% to 5%, 10%, 15%, 20%, 25% or 30% of an alcohol. In some aspects, the solvent comprises 0.1% to 20% of an alcohol, 1% to 10% of an alcohol or 1% to 5% 1% to 10% of an alcohol (e.g., ethanol). In some cases, the alcohol may be ethanol.

In some aspects, applying the solvent to the tissue comprises applying a discrete volume of solvent to the tissue site. In some aspect, the solvent is applied in a single droplet. In a further aspect, the solvent is applied in a discrete number of droplets from 1 to 10. In some embodiments, the solvent is applied to the sample from the reservoir via a channel independent of the gas. In further embodiments, the solvent is applied to the sample under low pressure. For example, in some aspects, the solvent is applied by a mechanical pump such that solvent is applied to the tissue site (e.g., moved into a reservoir where it is in contact with the tissue site) with minimal force thereby exerting minimal pressure (and producing minimal damage) at a tissue site. The low pressure may be less than 100 psig, less than 90 psig, less than 80 psig, less than 70 psig, less than 60 psig, less than 50 psig, or less than 25 psig. In some embodiments, the low pressure is from about 0.1 psig to about 100 psig, from about 0.5 psig to about 50 psig, from about 0.5 psig to about 25 psig, or from about 0.1 psig to about 10 psig. In particular aspects, the discrete volume of solvent is between about 0.1 and 100 µL, or between about 1 and 50 µL. In further aspects, collecting the applied solvent is between 0.1 and 30 seconds after the applying step. In a specific aspect, collecting the applied solvent is between 1 and 10 seconds after the applying step (e.g., at least 1, 2, 4, 5, 6, 7, 8 or 9 seconds). In further aspects, a method of the embodiments does not involve application of ultrasonic or vibrational energy to a sample or tissue. In some aspects, the tissue site in an internal tissue site that is being surgically assessed.

In a further aspect, a method of the embodiments comprises applying a fixed or discrete volume of a solvent (e.g., using mechanical pump) to a tissue site through a solvent conduit. In some aspects, the fixed or discrete volume of a solvent is moved through a solvent conduit into a reservoir where it is in direct contact with a tissue site (e.g., for 0.5-5.0 seconds). In further aspects, collecting the applied solvent comprises applying a negative pressure to pull the sample into a collection conduit and/or applying a gas pressure to push the sample into a collection conduit. In some aspects, the solvent is applied through a solvent conduit that is separate from the collection conduit. In further aspects, wherein a gas pressure is applied to push the sample into the collection conduit the gas pressure is applied through a gas conduit that is separate from the solvent conduit and the collection conduit. In certain aspects, wherein a gas pressure is applied to push the sample into the collection conduit, the applied gas pressure of less than 100 psig. For example, the gas pressure is preferably less than 10 psig, such as 0.1 to 5 psig. In still further aspects, a method of the embodiments is defined as producing no detectable physical damage to the tissue being assessed.

In still further aspects, the method may additionally comprise collecting a plurality liquid samples from a plurality of tissue sites. In some cases, the device (e.g., the probe) used to collect the samples is washed between each sample collection. In other aspects, a device used to collect the samples includes a disposable collection tip (probe) that can be changed between each sample collection. In particular aspects, the collection tip may be ejectable (e.g. capable of being ejected from the device). In certain aspects, the plurality of tissue sites comprise 2, 3, 4, 5, 6, 7, 8, 9, 10 or more tissues sites in vivo. In another aspect, the plurality of tissue sites surround a section of tissue that has been surgically resected (e.g., ex vivo). In a specific aspect, the resected tissue is a tumor. In some aspects, the method may be defined as an intraoperative method.

A further embodiment provides a method of identifying a sampled tissue site and a method to communicate location of the site to the device (probe) operator. Identification of a sampled tissue site allows the operator to access the molecular information recorded at sampled tissue site at a time after sampling molecules collected from the tissue. At least three types of identification approaches are recognized. In the first approach, an exogenous material is attached to the sampled tissue site that identifies the sampled molecular information. In a second approach, the device (probe) is equipped with a tracking sensor/emitter that allows recording the location of the probe (device) and communication to an imaging device when the molecular information is sampled. In a third approach, the tissue region is modified so that the site may be easily identified after harvesting tissue molecules. In the first approach, materials that may be attached to the sampled tissue site include, for example, a suture, a surgical clip, a biocompatible polymer that adheres to the tissue, or an RFID chip that is attached to a magnetic bead that allows easy reading and removal. In the second approach type, the probe may contain an RF emitter that is part of a RF surgical tracking system, an ultrasound emitter or reflector that is part of an intra-operative US imaging system. In this second approach, when the operator initiates collection of tissue molecules, the tracking system records location of the probe in the associated imaging system (e.g., RF, US, CT, MRI) that may be in communication with the device. The operator may then identify any of the sampled tissue sites at a later time by referring to the recorded image(s) that can indicate the location of sampled sites to the operator. In the third approach, the tissue is modified. In this third approach, a laser source in communication with the probe may be used to ablate or coagulate a pattern into the tissue that identifies the sampled site. Any of these three approaches may be combined. For example, approach 1, 2 and 3 could be combined wherein an exogenous material is attached to the tissue site after harvesting tissue molecules and a laser patterns the exogenous tissue while an RF sensor records location of the harvest location and communicates to the imaging device.

In yet still further aspects, the mass spectrometry comprises ambient ionization MS. As disclosed herein a probe in contact with a tissue site can be in fluid communication with the MS via a conduit. In some aspects, conduit between the probe and tissue site is less than about 10 m, 8 m, 6 m or 4 m from MS. In further aspects, the conduit is between about 0.5, 1.0, 1.5, 2.0, 2.5, 3.0 and 4.0 m in length. In several aspects, subjecting the sample to mass spectrometry analysis may comprise determining a profile corresponding to the tissue site. In another aspect, the method may additionally comprise comparing the profile to a reference profile to identify tissue sites that include diseased tissue. In other aspects, the method also comprises resecting tissue sites that are identified to include diseased tissue. In some aspects, the method is performed using an apparatus in accordance with any of the embodiments and aspects described above.

In a further embodiment, the invention provides an ex vivo method for assessing tissue samples comprising obtaining a plurality of liquid samples from a plurality of tissue sites in a subject, subjecting the plurality of liquid samples to mass spectrometry to obtain a plurality of profiles corresponding to the tissue sites, and comparing the plurality of profiles to reference profiles to identify tissue sites that include diseased tissue. In certain aspects, the liquid samples are comprised in a solvent. In further aspects, the diseased tissues comprise cancer cells.

In some aspects of the embodiments, the diseased tissue sites for assessment by methods and devices of the embodiments comprise (or are suspected of comprising) cancer cells. Cancer cells that may be assessed according to the embodiments include but are not limited to cells or tumor tissues from a thyroid, parathyroid, lymph node, bladder, blood, bone, bone marrow, brain, breast, colon, esophagus, gastrointestine, gum, head, kidney, liver, lung, nasopharynx, neck, ovary, pancreas, prostate, skin, stomach, testis, tongue, or uterus (or tissues surrounding such tumors). In some aspects, the cancer may be a neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxo sarcoma; liposarcoma; leiomyosarcoma; rhabdomyo sarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; or paragranuloma. In further aspects the cancer is a thyroid cancer, brain cancer (e.g., a glioma), a prostate cancer, a breast cancer (e.g., a triple negative breast cancer), a pancreatic cancer (e.g., a pancreatic ductal adenocarcinoma), acute myeloid leukemia (AML), melanoma, renal cell cancer or a cancer that has metastasized to a lymph node.

In still a further embodiment there is provided a method for characterizing a material comprising (a) applying a fixed or discrete volume of a solvent to the material; (b) collecting the applied solvent to obtain a liquid sample; and (c) subjecting the sample to mass spectrometry analysis to provide a mass spectrometry profile that characterizes the material. In some aspects, the material is commodity product and characterizing the material comprises identifying the material. For example, the commodity product can be food, such as a meat, fish, fungus, vegetable or fruit. Thus, in some aspects, characterizing the material comprises identifying the type of meat or fish the material is composed of. In the case where the material is a meat the method can comprise identifying the meat as, for example, lamb, deer, moose, chicken, turkey, sheep, dog, cat, horse, pork, beef, buffalo or goat. In further aspects, the method can be used to identify a meat as meat from a grass fed or grain fed animal. In the case where the material is a fish the method can comprise identifying the fish as, for example, tuna, salmon, cod, trout, halibut or sea bass. In further aspects, the method can be used to identify a fish as from a farm-raised or wild caught fish. In still further aspects, the fish can be a shell fish. In still further aspects, methods of the embodiments may be used to identify the region of origin for the food product such a fish or meat. In certain aspects, a method of characterizing a material is carried-out using an apparatus as described herein. For example the apparatus can comprise apparatus comprising: a chamber comprising a solvent; a gas supply (e.g. a pressurized gas supply); a mass spectrometer; and a probe comprising a reservoir, a first conduit, a second conduit and a third conduit, wherein: the first conduit is in fluid communication with the chamber; the second conduit is in fluid communication with gas supply; and the third conduit is in fluid communication with the mass spectrometer.

In a further embodiment there is provided a method for characterizing a material comprising (a) applying a fixed or discrete volume of a solvent to the material; (b) collecting the applied solvent to obtain a liquid sample; and (c) subjecting the sample to mass spectrometry analysis to provide a mass spectrometry profile that characterizes the material. In some aspects, characterizing the material comprises detecting and/or quantifying the amount of a compound in the material. For example, the compound may be small molecule, such as pharmaceutical, a drug (e.g., a pain killer), a pesticide (e.g., an insecticide), a herbicide, an antibiotic or a toxin. For example, in some aspects, the a drug can be adderall, cocaine, codeine, morphine, marijuana, amphetamine, methamphetamine, MDMA, heroin, ketamine, lysergic acid diethylamide or oxycodone. In further aspects, the compound can be a pesticide or herbicide such as dicamba, glyphosate, azoxystrobin or atrazine. In certain aspects, a method of characterizing a material is carried-out using an apparatus as described herein. For example the apparatus can comprise apparatus comprising: a chamber comprising a solvent; a gas supply (e.g. a pressurized gas supply); a mass spectrometer; and a probe comprising a reservoir, a first conduit, a second conduit and a third conduit, wherein: the first conduit is in fluid communication with the chamber; the second conduit is in fluid communication with gas supply; and the third conduit is in fluid communication with the mass spectrometer.

As used herein, "sample" or "liquid samples" can refer to extracts from tissues or other biological specimens (e.g., extracts comprising proteins and metabolites) obtained by contacting tissue or biological specimen with a solvent according to the embodiments. In some aspects, a sample can be an extract from a non-biological specimen, such as the surface on an object (e.g., a forensic sample).

As used herein, "essentially free," in terms of a specified component, is used herein to mean that none of the specified components has been purposefully formulated into a composition and/or is present only as a contaminant or in trace amounts. The total amount of the specified component resulting from any unintended contamination of a composition is therefore well below 0.01%. Most preferred is a composition in which no amount of the specified component can be detected with standard analytical methods.

As used herein in the specification and claims, "a" or "an" may mean one or more. As used herein in the specification and claims, when used in conjunction with the word "comprising", the words "a" or "an" may mean one or more than one. As used herein, in the specification and claim, "another" or "a further" may mean at least a second or more.

As used herein in the specification and claims, the terms "conduit" and "tube" are used interchangeably and refer to a structure that can be used to direct flow of a gas or liquid.

As used herein in the specification and claims, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating certain embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

I. The Present Embodiments

Figure 1:
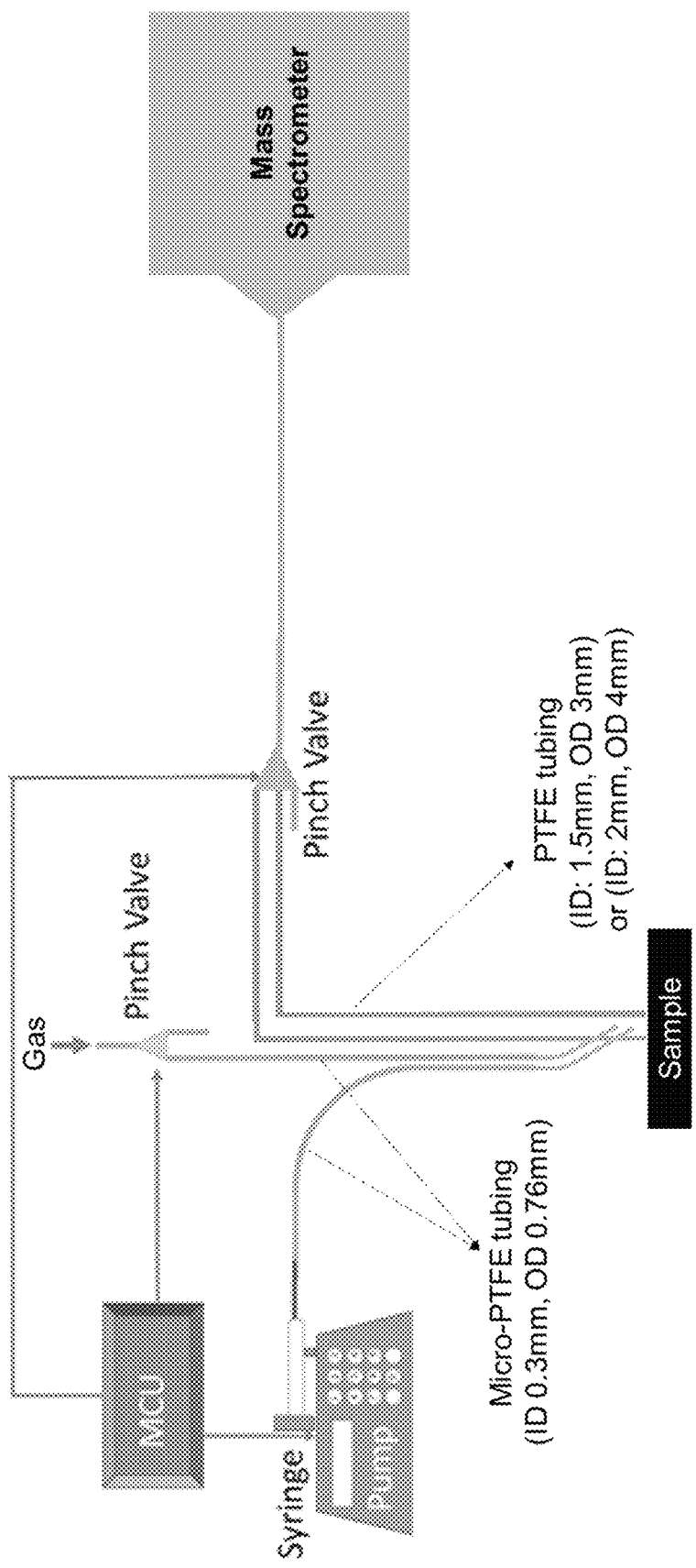
FIG. 1: Representative schematic of a mass spectroscopy probe for minimally invasive surgery.

In certain aspects, the instant application provides methods and devices for minimally invasive molecular assessment of samples, such as tissue samples. In particular, aspects the methods can be used to assess multiple tissue sites during an operation (or biopsy) of the tissue. This feature allows for accurate identification of diseased tissues (e.g., tissue sites retaining cancer cells) in "real-time" allowing surgeons to more accurately address only the diseased tissue relative to surrounding normal tissues. In particular aspects, the methods disclosed here can involve delivery of a fixed or discrete volume of solvent to a tissue site, followed by collection of a liquid sample from the site and analysis of the liquid sample by mass spectrometry. Importantly, rather than being applied in a high-pressure spray, solvent is applied as discrete droplets and at low pressure. These methods allow for accurate collection of samples from a distinct tissue site while avoiding damage to the tissue being assessed. The resulting mass spectrometry profile from collected samples allows for differentiation of diseased versus normal tissue sites. The method can be repeated at multiple sites of interest to very accurately map molecular changes (e.g., in a tissue). Importantly, the profiles of samples could be differentiated even without the use of an ionization source. Thus, while methods of the embodiments could be used in conjunction with an ionization source, the use of such a source is not required. These methodologies can allow assessment of plurality of tissue sites over a short range of time, thereby allowing for very accurate assessment of the boundaries of diseased versus normal tissues.

In some aspects, the methods detailed herein can be used to collect and analyze samples from a wide range of sources. For example, the methods can be used to assess surgical, forensic, agriculture, pharmaceutical, and/or oil/petroleum samples.

In some aspects, the materials (PDMS and PTFE) and solvent (e.g., water only solvents) used in the devices of the embodiments are biologically compatible, such that they can be used in surgery in for real-time analysis. Furthermore, because the devices can be very compact, it can be hand-held and used in used in minimally invasive surgical procedures, or non-surgical procedures.

In some aspects, the present invention provides devices of extended length and increased compactness for delivery of fixed or discrete volumes of solvents to tissues for use in minimally invasive surgeries. In some aspects, these methods can be encapsulated in a variety of form factors such as a conduit, ranging from 0.5 mm to 10.0 mm inner diameter (e.g., with an inner diameter of between about 1.0 and 5.0; 1.0 and 10.0; 2.0 and 8.0; or 5.0 and 10.0 mm). In some aspects, the site of delivery of a fixed or discrete volume of solvent, followed by collection of a liquid sample may be inside the body, such as a surgical site. In some aspects, two smaller conduits may be inserted into a third, larger, conduit to create a multi-lumen catheter. For example, the multi-lumen catheter can have 2, 3, 4, 5, 6 or more luminal spaces with each having an internal diameter of, e.g., 0.05 to 5.0 mm; 0.1 to 5.0 mm; 0.25 to 3.0 mm; or 0.5 mm to 10.0 mm. The multi-lumen catheter may be attached to a mass spectrometry device for analysis of sample tissues inside the body during surgery, while avoiding unnecessary damage to surrounding tissues.

In some aspects, the device may be used through cannulas or catheters in minimally invasive surgical or endoscopy procedures, or may be used in non-surgical procedures through needle guides or biopsy guides. In some aspects, the present invention can be integrated into a robotic surgical system allowing several regions of the human body cavity to be quickly sampled and analyzed. In some aspects, the device be used to analyze tissues using a database of molecular signatures and machine learning algorithms, allowing diagnosis in real time for each sampled region. The present invention may be used in a wide variety of oncological and other surgical interventions, such as endometriosis, for which real time characterization and diagnosis of tissues are needed.

In some aspects, the present disclosure provides an attachment to the probe, for fine manipulation of the probe during minimally or non-invasive procedures. For example, the attachment to the probe may be a fin. In some aspects, such a fin may be composed of the same material as the probe. In some cases, the fin is made of PDMS. A fin can, in some aspects, be formed by an injection molding process or it may be 3D printed. In some aspects, the present invention may further comprise a device for grasping the probe, external to the probe, in order to manipulate the probe during laparoscopic procedures. The grasping device may be used to hold, rotate, or move the probe, or may grasp the fin attached to the probe, in order to move or rotate the probe.

In some aspects, the present invention maintains a reservoir using a multi-lumen catheter with recessed ports for depositing water and nitrogen gas during laparoscopic surgical procedures. A multi-lumen catheter may be formed, for example, using a multi-lumen extrusion as is well known in the art. These catheters may be utilized in any cannula. The most commonly used cannulas are of 5 mm and 10 mm diameters, and are typically used for laparoscopic surgeries.

In some aspects, the present disclosure provides tools, devices and methods for manipulation of the probe during endoscopy. For example, multi-lumen tubing may be used with an external vacuum source in order to attach the probe to the tissue surface while analyzing.

In some aspects, the present invention provides a shutter system that occludes the orifice of the minimally invasive surgical device. In some aspects, this shutter system may be a catheter balloon that is integrated within the device or added separately to the device. The shutter, or balloon, may close the probe tip, preventing unwanted biological material from entering the device, including the lumens and tubing, upon insertion of the catheter into the patient. The shutter or balloon may disallow endogenous biological fluids from entering the mass spectrometer after analysis has been initiated, thus preventing contamination of the results. Finally, closing of the shutter or balloon may prevent excess nitrogen gas and water from entering the body. Inclusion of lengthened probes for minimally invasive surgeries and occlusion technologies for the tips of the probes may mitigate the unpredictable and often tumultuous nature of internal organ movement and organ systems during surgery which could affect signal acquisition. Balloons technologies could also be used in other region of the device instead or in addition to the pinch valves to control solvent and gas motions through the tubes.

In some aspects, the present invention may be used with robotic manipulation. In some aspects, the technologies of the present invention may integrate in modern surgical theaters through an accessory port, or via a robotic arm. These devices may be integrated into robotic systems such as the Intuitive Surgical da Vinci robotic surgical system. A device of the present invention may have its own dedicated arm in a robotic system, or be handled by robotic graspers by incorporating a "fin" onto the probe. Smaller and larger diameters can also be used to be coupled to any existing catheters, cannulas and also needle/biopsy guides.

In some aspects, a tracking probe can be integrated with this device in order to display and record where the tissue sample has been analyzed to better assist the surgeon in localizing the sampling points both intraoperatively or otherwise. For example, during intraoperative ultrasound, an ultrasound emitter on the device may be utilized to display the probe when sampling. The probe may be integrated with a tracking device based on radio frequency technology, such as the Biosense Webster Carto system. In that case, the probe may display the device/sampling location on any of a variety of imaging modalities, such as intraoperative UltraSound (US)/Computed Tomogrpahy (CT)/Magnetic Resonance Imaging (MRI)/Optical Coherence Tomography (OCT). Additionally, fluorescent imaging and molecular dyes may be used to track the analyzed areas and charted to provide 2-dimensional or 3-dimensional spatial imaging. More simply, the probe tip may be coated with a surgical dye which is then stamped on the tissue to track the region analyzed. Yet another tracking approach is to integrate an RF emitter into the probe so that the spatial location may be tracked.

In some aspects, the probe of the present invention may be used to assist surgeons and medical professionals during minimally invasive surgical interventions by providing comprehensive and definitive diagnostic molecular information in vivo and in real time, without necessarily causing damage or alteration to the patient's native living tissues. The handheld MasSpec Pen has demonstrated a capacity to do this during non-laparoscopic/endoscopic surgical procedures (U.S. patent application Ser. No. 15/692,167 incorporated herein by reference, in its entirety). Similarly to the handheld MasSpec Pen, the present invention is suitable for ex vivo analysis of tissues (fresh, frozen, sections, biopsies) or other clinical specimens that might be examined by a pathologist, and may be used for chemical analysis of any given sample for which direct analysis is desired in confined and spatially limited domains (animals, plants, explosives, drugs, etc). A variety of tissue types may be analyzed as well, including but not limited to, breast, kidney, lymph node, thyroid, ovary, pancreatic and brain tissues.

In some aspects, the probe of the present invention may be used in conjunction with surgical instruments for the treatment of a disease. A variety of surgical instruments may be used to excise or ablate cells or tissues, including, but not limited to, laser ablation tools, tools for cauterization or electrocauterization, or tools for the manual dissection of tissue such as a scalpel.

Thus, many regions of the human body cavity can be quickly sampled during surgery, and analyzed (e.g., by using a database of molecular signatures and machine learning algorithms). Therefore, the diagnostic results may be provided in real time for each sampled region. Exemplary devices for use in these methods are detailed below.

II. Exemplary Features of a Device of the Embodiments

A. Shutter Systems

In some aspects a device of the embodiments further comprises a shutter system that can occlude the orifice, and creates a separation between the reservoir and the tissue. For example, the shutter system can activate after the droplet rests for 3 seconds and before the droplet is transported to the mass spectrometer. One reason for this is to ensure no biological material reach the mass spectrometer and cause damage to the instrument. The shutter can be an iris diaphragm, a mechanical closure, gate, or tapenade. An additional design for the shutter is a balloon mechanism, which seals the exterior of the device from the tissue. The balloon can be positions on the distal end of the conduit, e.g., perpendicular to the pen or probe. When activated, the balloon expands and fills up the reservoir towards the direction of the tissue. This accomplishes at least 3 things: first it gently lifts the pen tip off of the tissue using the inflated balloon, insuring that there is no damage to the tissue. This is to ensure that the probe remains nondestructive and biocompatible in case the analyzed tissue is determined to be 'normal'. Secondly, it seals the solvent droplet that is inside the reservoir and prevents leakage or absorbance of lipids after the sampling window. Thirdly, it creates a seal at the end of the conduit, which will allow for more effective transfer of the droplet to the mass spectrometer.

B. Catheter Systems

In some cases, where a probe is incorporated into a laparoscopic/endoscopic device a reservoir includes using a multi-lumen catheter, e.g., with recessed ports for depositing water and nitrogen gas. The reservoir also retains the water during the extraction period. A multi-lumen catheter can be formed for example using a multi-lumen extrusion as is well known in the art. It has been demonstrated that these catheters can be utilized in any cannula, most commonly 5 mm and 10 mm diameters, for laparoscopic surgeries. This technology is compatible with robotic manipulation such as the Intuitive Surgical da Vinci robotic surgical system. The Laparoscopic/Endoscopic probes will easily integrate in current surgical theaters through an accessory port or via a robotic arm. Smaller and larger diameters can also be used to be coupled to any existing catheters, cannulas and also needle/biopsy guides.

C. Valve Systems

In further aspects, a probe system of the embodiments can incorporate additional valves. For example, micro-solenoid valves can be located at each conduit, e.g., at the distal end of the sampling probe. These will be individually controlled by an arduino, microcontroller, or signal. In some cases the value operation is automated. In other cases it can be manually controlled. In some aspects, valves are positioned in the inner wall of the solvent conduit sealing the conduits. Thus, by using such values, only two or even one conduit can be used in the sampling operation. For example, a delivering solvent conduit and a return conduit to transfer the droplet to the mass spectrometer. Additional microsolenoids could be implanted to have more control. For example, three or four micro-solenoids can be into the probes of the embodiments.

D. Further Surgical System Features

In some aspects, medical devices require passage to areas of the body that are difficult to maintain manual control. One solution is to use endoscopic catheters, but these are often less precise when compared to handheld devices. Further control can be attained using robotic tools that can function nearly to the same extent, and sometimes better than physicians equipped with a traditional scalpel. A further feature of the Laparoscopic/Endoscopic probes of the embodiments is a 'fin' that can be grasped by forceps, robotic tools, or laparoscopic graspers. This will allow the probe to be used in a variety of modalities without sacrificing resolution or sensitivity. In some aspects, the fin itself is a gradual sloped protrusion from the exterior of the conduit running parallel to said conduit. It is textured to provide extra traction for the grasping mechanism.

In further aspects, a tracking probe can be integrated with this device in order to display and record where the tissue sample has been analyzed to better assist the surgeon in localizing the sampling points both intraoperatively or otherwise. For intraoperative ultrasound, an ultrasound emitter on the device may be utilized to display the probe when sampling. Alternatively, the probe can be integrated with a tracking device based on radio frequency technology, such as the e.g., Biosense Webster Carto system. With this approach, the probe displays the device/sampling location on any various imaging modalities like intraoperative Ultra-Sound (US)/Computed Tomography (CT)/Magnetic Resonance Imaging (MRI)/Optical Coherence Tomography (OCT).

In some further aspects, tissue sites that are assessed by a probe of the embodiments can be marked. For example, a dye that is up-taken by cancerous cells and normal cells, which will mark where the probe has been placed. In some aspects, a chemical dye can be delivered using an additional conduit in the catheter or by using a multilumen catheter. An alternative delivery of a tracking dye is to dissolve it in the solvent that we use to analyze the tissue. For instance, one advantage of using a dye within the solvent is that it will directly correlate with where the tissue sample was taken, instead of the peripheral region. Of course in this aspects, the chemical dye would be present in the mass spectra and would have to be distinguished from biomolecules in a sample. In some aspects, it may useful to make the dye visible (e.g., in white operating room light). In other aspects, the dye may be a fluorescent dye. In yet a further aspect, the pen tip can be coated with a surgical dye, which is then stamped on the tissue to track the region analyzed. Likewise, as discussed above, a tracking approach can be used to virtually map the tissues sites analyzed. For instance, a RF emitter can be integrated into a probe so that the spatial location may be tracked. Thus, in some aspects, dyes (or probe tracking) can be used to track analyzed areas of tissues. In some aspects, tissues analyzed can be charted to provide 2 dimensional and 3 dimensional spatial imaging.

In further aspects, a probe system can include a filter. For example a filter can prevent biological tissue from going into the conduits. For example, a filter mesh system can be incorporated within the device to prevent smaller bodies of tissue, protein aggregates, or coagulated cell clusters from entering. This mesh could be placed at the opening and have contact with the tissue, or be positioned higher up within the probe, such that no tissue contact occurs. In some aspects such a filter mesh comprises average apature sizes of less than about 1.0, 0.5, 0.25 or 0.1 mm. Since solid matter can damage a mass spectrometer, such a filter system can increase instrument lifespan with out negatively effecting signal detected.

In still further aspects, an endoscopic/laparoscopic probe of the embodiments is integrated with a microcontroller, user interface, and/or associated hardware that will operate with appropriate software.

In some further cases, a light, such as a LED will be incorporated to provide visual feed back to the user, for example, to indicate that the probe is ready for sampling, in the process of doing so, or needs to be replaced/repaired. Acoustic feedback can also be used, for instance, to let the user know what step of the process the device is in (e.g., since physical cues may be unavailable laparoscopically). A user interface system can also be integrated with the device, such as in a foot pedal and buttons on the housing of the probe.

III. Assay Methodologies

In some aspects, the present disclosure provides methods of determining the presence of diseased tissue (e.g., tumor tissue) or detecting a molecular signature of a biological specimen by identifying specific patterns of a mass spectrometry profile. Biological specimens for analysis can be from animals, plants or any material (living or non-living) that has been in contact with biological molecules or organisms. A biological specimen can be samples in vivo (e.g. during surgery) or ex vivo.

A profile obtained by the methods of the embodiments can correspond to, for example, proteins, metabolites, or lipids from analyzed biological specimens or tissue sites. These patterns may be determined by measuring the presence of specific ions using mass spectrometry. Some non-limiting examples of ionizations methods that can be coupled to this device include chemical ionization, laser ionization, atmospheric-pressure chemical ionization, electron ionization, fast atom bombardment, electrospray ionization, thermal ionization. Additional ionization methods include inductively coupled plasma sources, photoionization, glow discharge, field desorption, thermospray, desorption/ionization on silicon, direct analysis in real time, secondary ion mass spectroscopy, spark ionization, and thermal ionization.

In particular, the present methods may be applied or coupled to an ambient ionization source or method for obtaining the mass spectral data such as extraction ambient ionization source. Extraction ambient ionization sources are methods with, in this case, liquid extraction processes dynamically followed by ionization. Some non-limiting examples of extraction ambient ionization sources include air flow-assisted desorption electrospray ionization (AF-ADESI), direct analysis in real time (DART), desorption electrospray ionization (DESI), desorption ionization by charge exchange (DICE), electrode-assisted desorption electrospray ionization (EADESI), electrospray laser desorption ionization (ELDI), electrostatic spray ionization (ESTASI), Jet desorption electrospray ionization (JeDI), laser assisted desorption electrospray ionization (LADESI), laser desorption electrospray ionization (LDESI), matrix-assisted laser desorption electrospray ionization (MALDESI), nanospray desorption electrospray ionization (nano-DESI), or transmission mode desorption electrospray ionization (TM-DESI).

As with many mass spectrometry methods, ionization efficiency can be optimized by modifying the collection or solvent conditions such as the solvent components, the pH, the gas flow rates, the applied voltage, and other aspects which affect ionization of the sample solution. In particular, the present methods contemplate the use of a solvent or solution which is compatible with human issue. Some non-limiting examples of solvent which may be used as the ionization solvent include water, ethanol, methanol, acetonitrile, dimethylformamide, an acid, or a mixture thereof. In some embodiments, the method contemplates a mixture of acetonitrile and dimethylformamide. The amounts of acetonitrile and dimethylformamide may be varied to enhance the extraction of the analytes from the sample as well as increase the ionization and volatility of the sample. In some embodiments, the composition contains from about 5:1 (v/v) dimethylformamide:acetonitrile to about 1:5 (v/v) dimethylformamide:acetonitrile such as 1:1 (v/v) dimethylformamide:acetonitrile. However, in preferred embodiment the solvent for use according to the embodiments is a pharmaceutically acceptable solvent, such as sterile water or a buffered aqueous solution.

IV. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Minimally Invasive Probe for Mass Spectrometry Design

Figure 2:
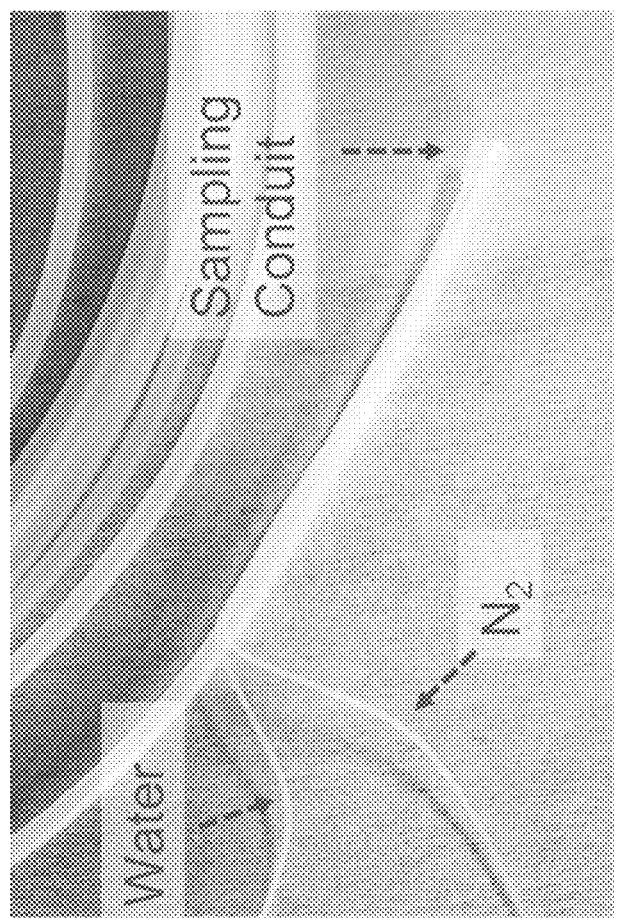
FIG. 2: Multilumen tubing for use with the mass spectroscopy probe for minimally invasive surgery.
Figure 3:
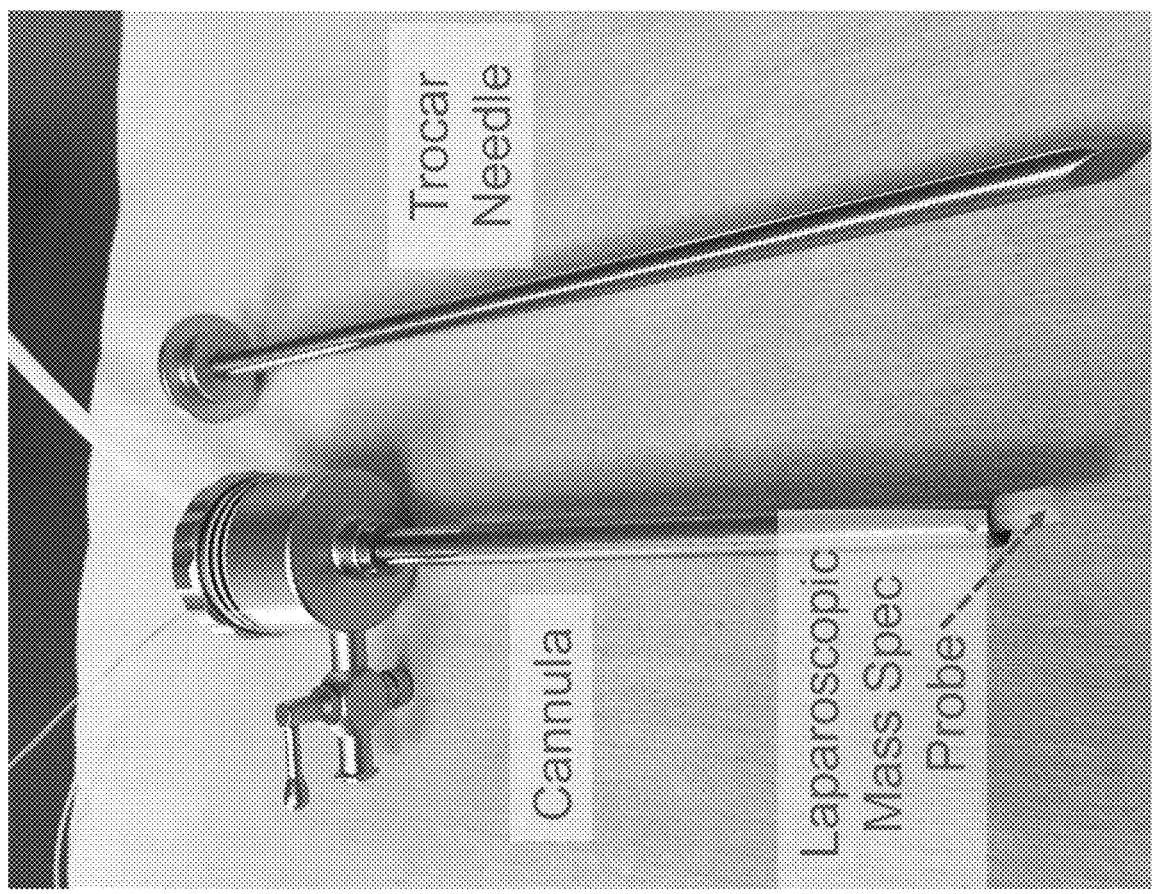
FIG. 3: A cannula and trocar needle for housing and inserting the mass spectrometry probe for minimally invasive surgery.
Figure 4:
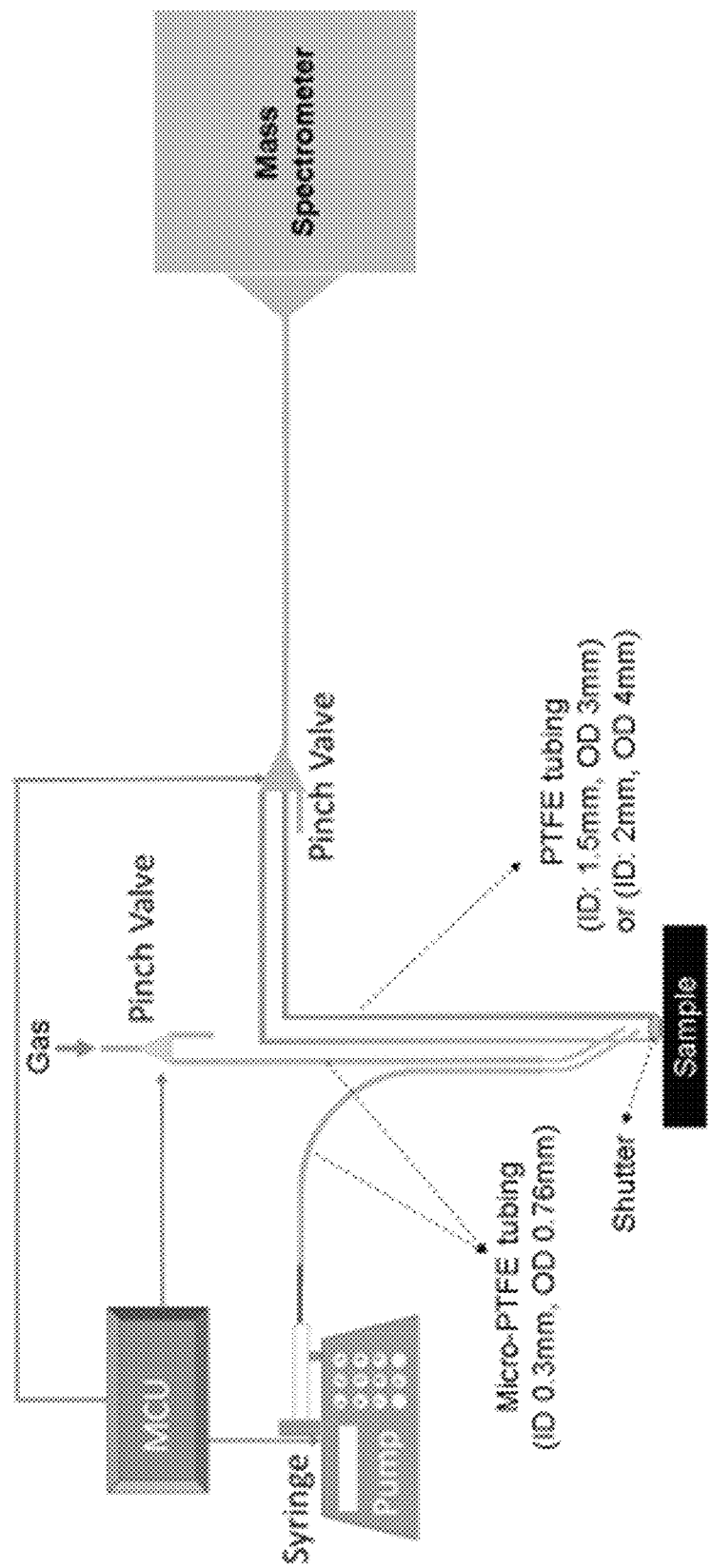
FIG. 4: Representative schematic of a mass spectrometry probe for minimally invasive surgery. This embodiment includes a shutter for occluding the probe.
Figure 5:
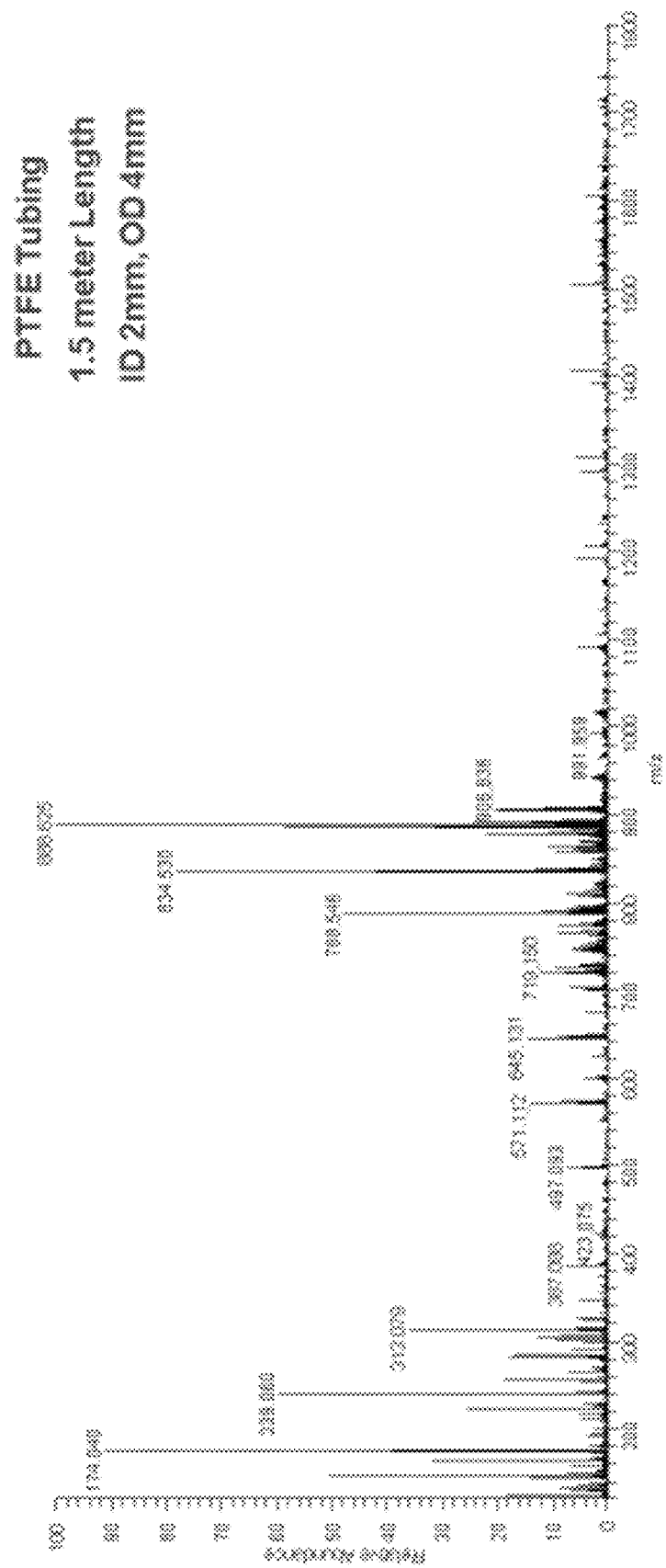
FIG. 5: Mass spectra of mouse brains tissue section from the minimally invasive mass spectrometry probe using Q Exactive Orbitrap Mass Spectrometer. PTFE tubing of 1.5 meters was used with an inner diameter of 2 mm and outer diameter of 4 mm.
Figure 6:
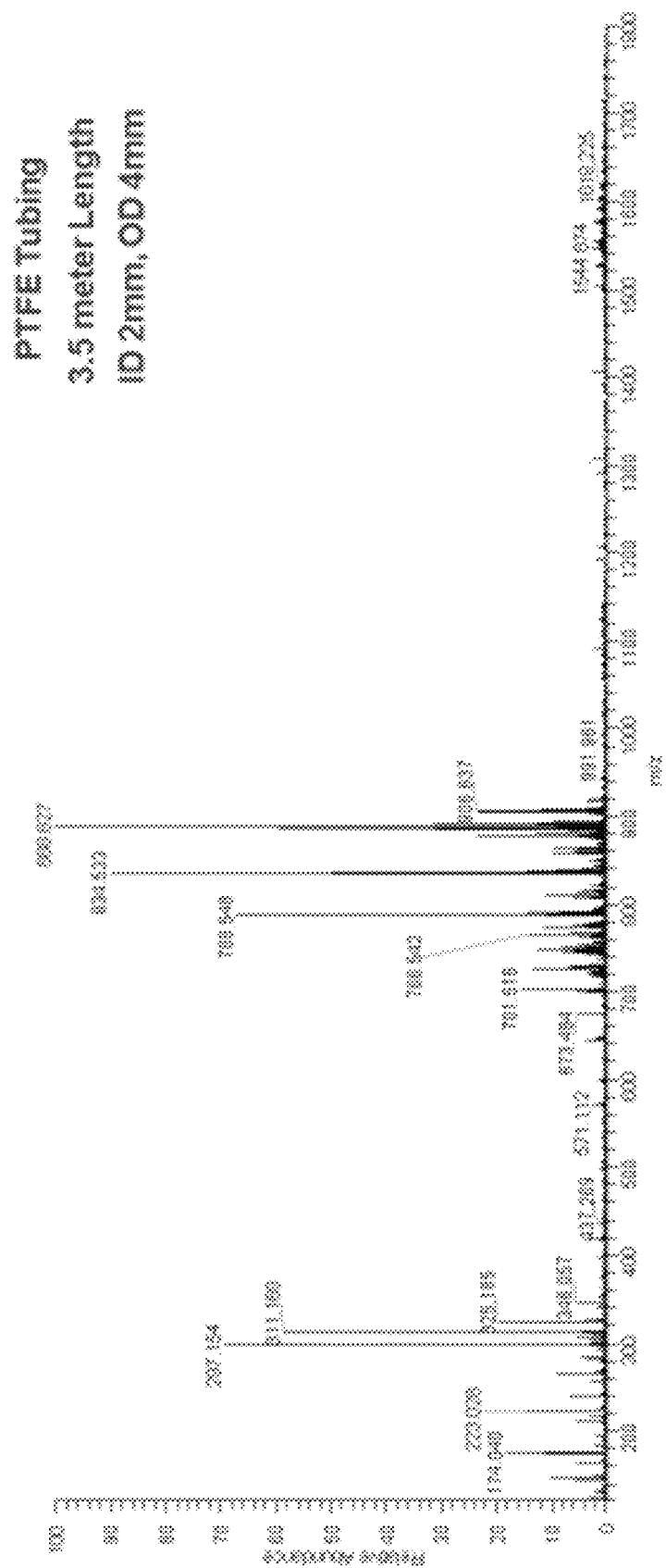
FIG. 6: Mass spectra of mouse brains tissue section from the minimally invasive mass spectrometry probe using Q Exactive Orbitrap Mass Spectrometer. PTFE tubing of 3.5 meters was used with an inner diameter of 2 mm and outer diameter of 4 mm.
Figure 7:
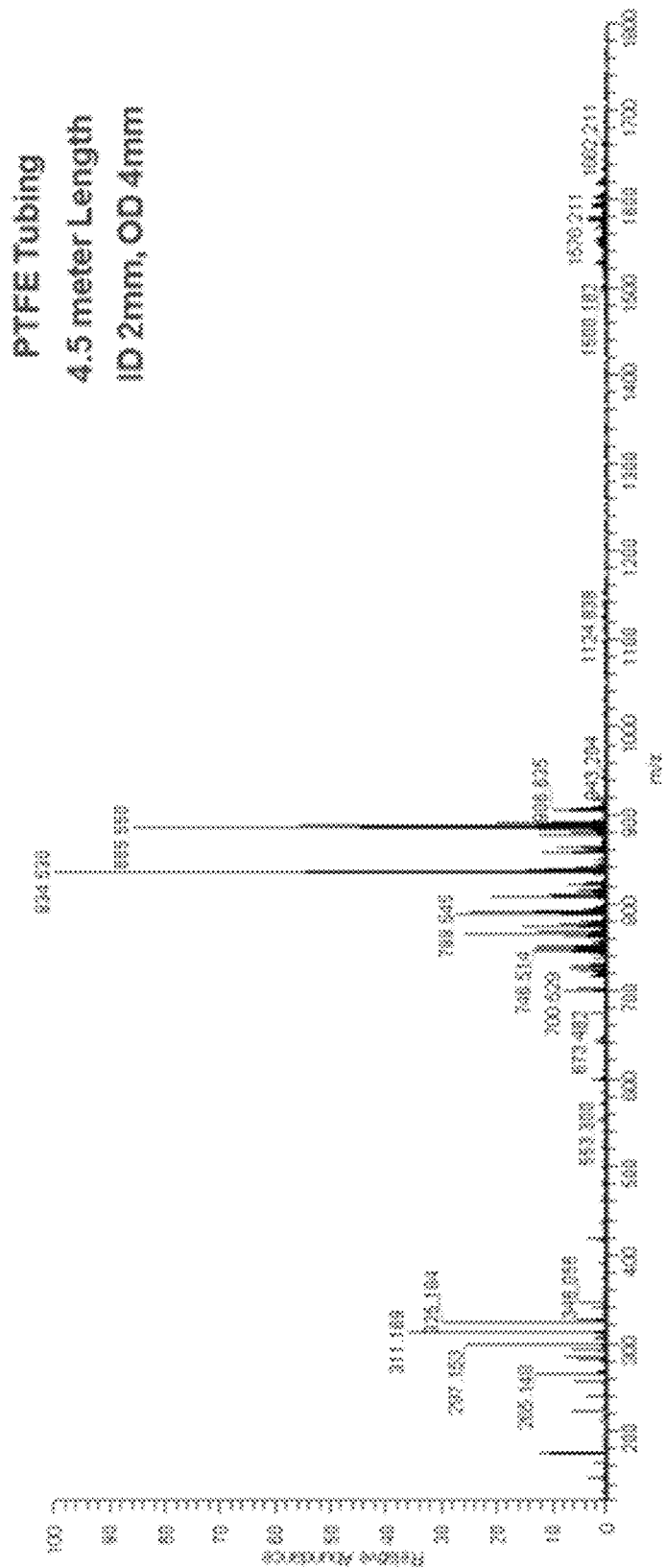
FIG. 7: Mass spectra of mouse brains tissue section from the minimally invasive mass spectrometry probe using Q Exactive Orbitrap Mass Spectrometer. PTFE tubing of 4.5 meters was used with an inner diameter of 2 mm and outer diameter of 4 mm.
Figure 8:
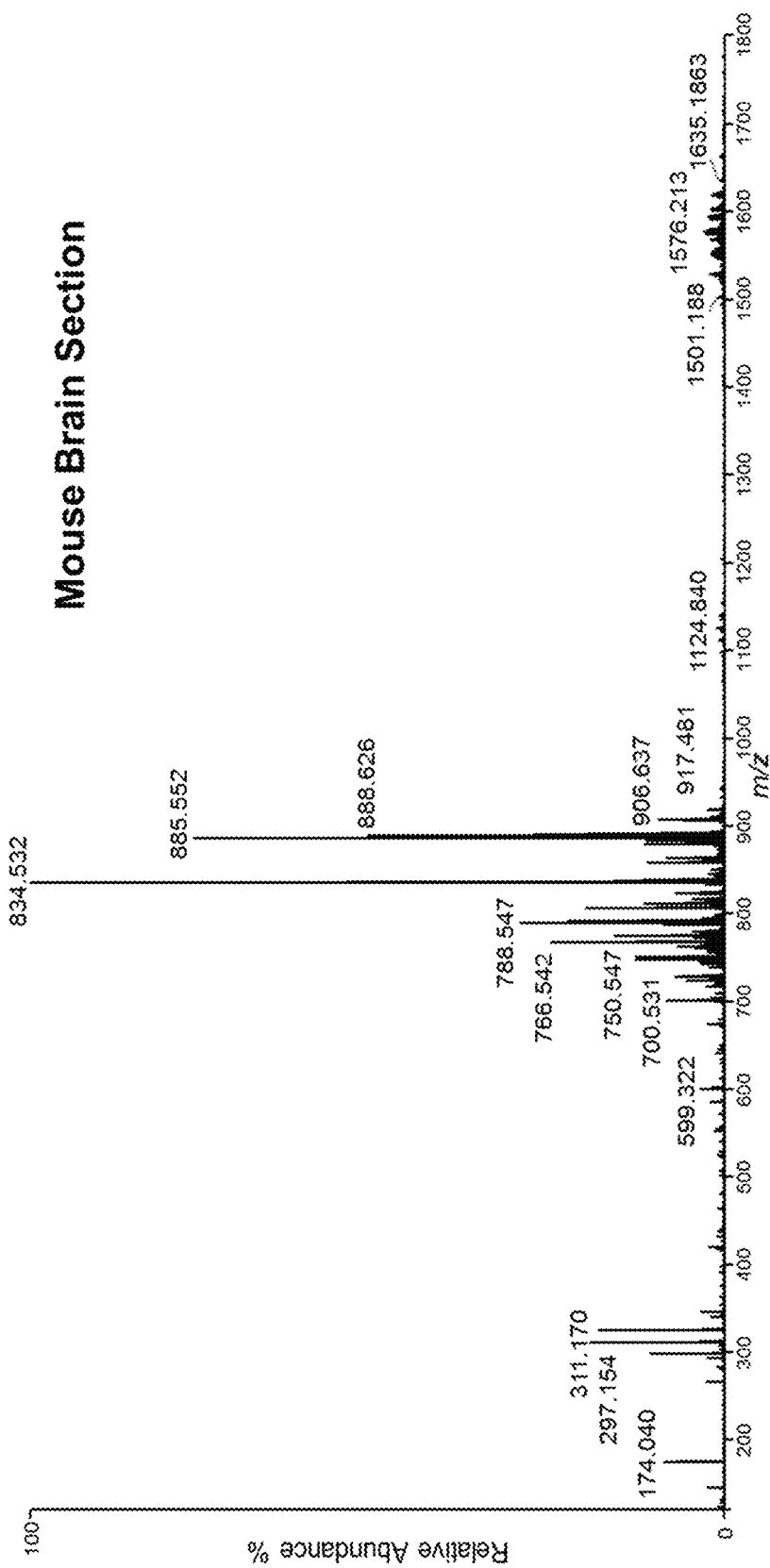
FIG. 8: Mass spectra of mouse brain tissue section from the minimally invasive mass spectrometry probe using Q Exactive Orbitrap Mass Spectrometer.
Figure 9:
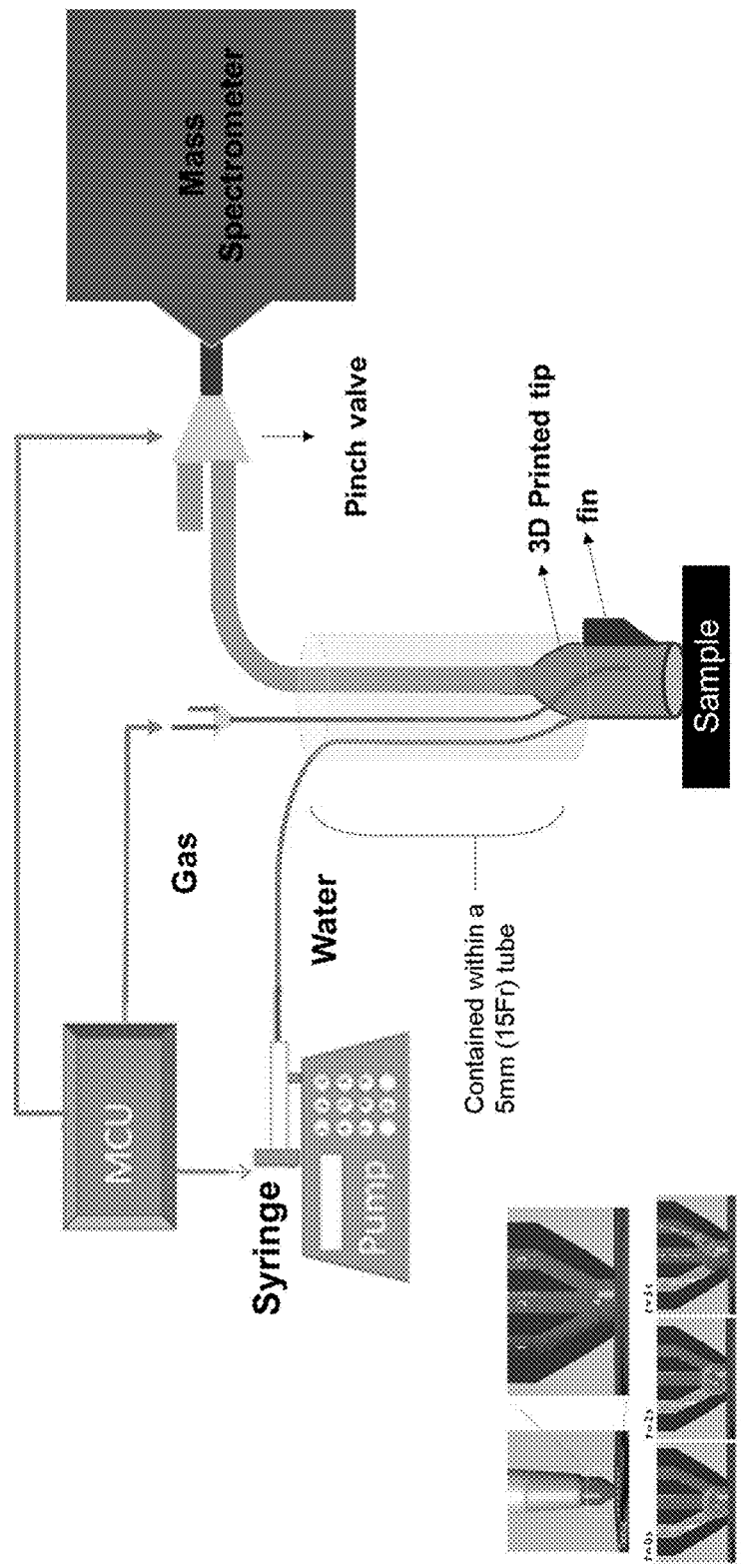
FIG. 9: Representative schematice of a mass spectrometry probe for minimally invasive surgery. Depicted on the lower left is the multichannel probe tip.
Figure 10:
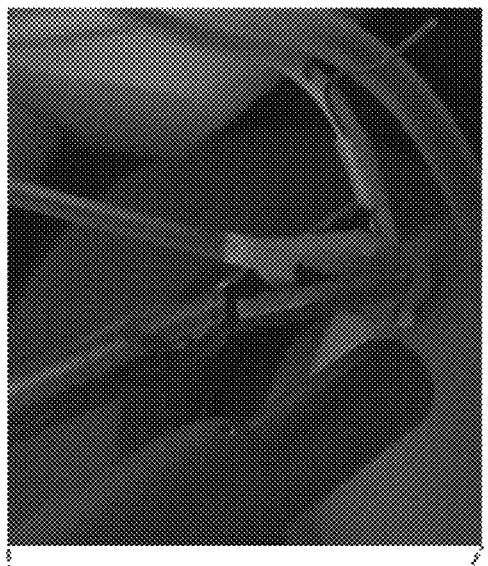
FIG. 10: Simulated laparoscopic surgery shown from a laparoscopic optical camera on a simulated uterus. Shown on the right are forceps holding the minimally invasive mass spectrometry probe.
Figure 10:
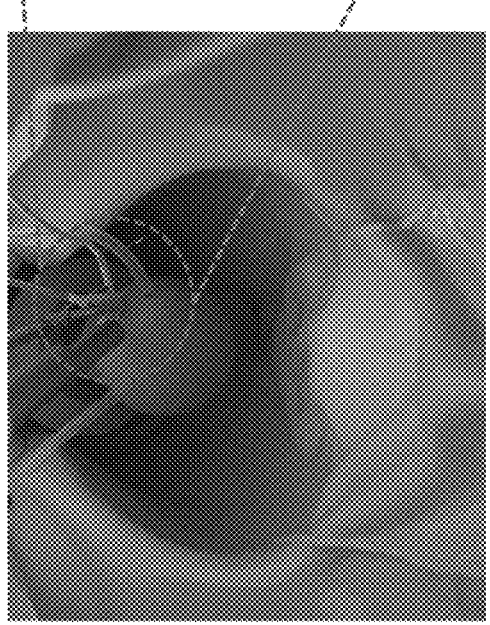
Figure 13:
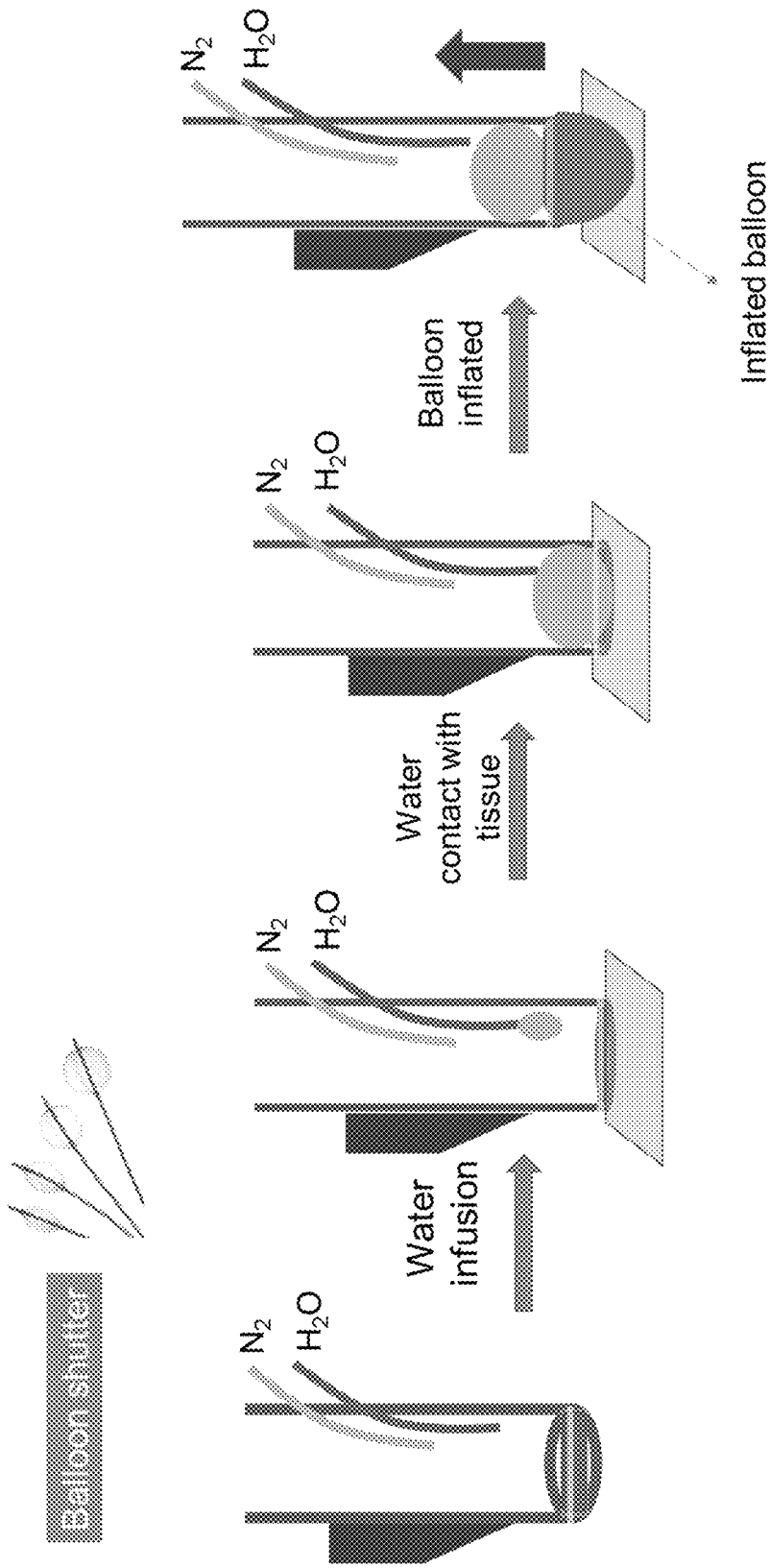
FIG. 13: Depiction of the mechanics of a balloon shutter for use with the minimally invasive mass spectrometry probe.

The system developed consists of three main parts: 1) a syringe pump that is programmed to deliver a discrete solvent volume using a controlled flow rate; 2) tubing systems integrated to two-way pinch valves for controlled solvent and gas transport; 3) a probe tip which is used for direct sampling of biological tissues. The tubing systems and probe tip are also integrated into a minimally invasive surgical device such as a cannula or catheter for use in laparoscopic or endoscopic surgeries. Several iterations of the system were explored and optimized with the ultimate goal of minimizing tissue damage, maximizing tissue-analyte extraction, and maximizing solvent transmission to the mass spectrometer. FIG. 1 shows a schematic figure of one example of a minimally invasive apparatus for analyzing biological tissue. The syringe pump feeds solvent and gas into the minimally invasive probe via micro-PTFE tubing. The probe maintains contact with the sample, retains solvent during interaction with the tissue. The tip was manufactured using 3D-printing and is made of biologically compatible polydimethylsiloxane (PDMS). The probe has three main ports: one for the incoming tubing system, a central port for gas delivery, and a third for the outgoing tubing system. All ports come in junction at a small reservoir where the droplet is retained and exposed to the tissue sample for a controlled amount of time, allowing for efficient extraction of molecules. The size of the reservoir determines the spatial resolution of the device. A solvent volume of 10 μL is exposed to the tissue sample. FIG. 2 shows the three conduit tubes. The three conduit tubes used are made of polytetrafluoroethylene (PTFE), which is also biologically compatible. The tube from the syringe pump is used to deliver solvent from syringe pump to the probe tip, while the other micro-PTFE tube is used to deliver an inert gas ($N_2$ or $CO_2$) to the probe tip. The gas serves three main purposes: 1) tissue drying prior to analysis; 2) prevent solvent gap due to the mass spectrometer's vacuum when the reservoir is closed by contacting the tissue specimen; 2) assist solvent transport from tissue to the mass spectrometer through the wider PTFE tubing. The larger PTFE tubing is directly connected to the inlet of the mass spectrometer so that the positive pressure of the mass spectrometer vacuum system is used to drive the droplet from the reservoir to the mass spectrometer inlet for ionization. FIG. 9 shows a schematic of the minimally invasive probe which includes a diagram of the tip of the probe, including the tree conduit tubes and the reservoir at the base (labelled 4). FIG. 3 shows two of the possible devices to house the minimally invasive probe. The cannula shown has the gas and solvent tubing entering the top, as well as the tubing to the mass spectrometer. The probe is shown emerging from the bottom of the cannula. The probe may also be introduced into the body cavity using a trocar needle. FIG. 10 depicts a simulated laparoscopic uterine surgery, and shows that the minimally invasive probe may be controlled by forceps. A shutter system that occludes the orifice of the minimally invasive probe may be employed as shown in FIG. 4. One option for the shutter is to use a catheter balloon which may close the probe tip, a diagram of which is shown in FIG. 13, preventing unwanted biological material from entering the device, including the lumens and tubing, upon insertion of the catheter into the patient. The shutter may disallow endogenous biological fluids from entering the mass spectrometer after analysis has been initiated, thus preventing contamination of the results. Closing of the shutter can also prevent excess nitrogen gas and water from entering the body. The use of a shutter in the lengthened probes necessary for minimally invasive surgery may help mitigate the unpredictable and often tumultuous nature of internal organ movement and organ systems during surgery which could affect signal acquisition. The minimally invasive mass spectrometry probe may also include a vacuum tube separate from the sample vacuum above. The purpose of this second vacuum tube is to gently secure, or latch, the tip of the probe onto the tissue during analysis.

The time events involved in the device operation are automated and precisely controlled by software that communicates with an Arduino system and two two-way pinch valves. All pinch valves are closed until the process is initiated when, under 300 µL/min, a pulse is sent to the pump to infuse the solvent for two seconds and stop, generating a 10 µL droplet filling in the minimally invasive probe reservoir. The gas and mass spectrometer tubes are closed at pinch valves, allowing the solvent in the reservoir to interact with the tissue for three seconds to extract the molecules. The pinch valves controlling the gas and mass spectrometer tubes are opened simultaneously, allowing the droplet to transfer to the mass spectrometer for ionization and molecular analysis. A pulse is sent to the pump to infuse the solvent for another 12 seconds and stop, to completely drive all the extracted molecules into the mass spectrometer. The gas and mass spectrometer tubes are left open for another 20 seconds to allow all the solvent in the mass spectrometer tube to go into the mass spectrometer. The total analyzing time is 37 seconds.

Figure 15:
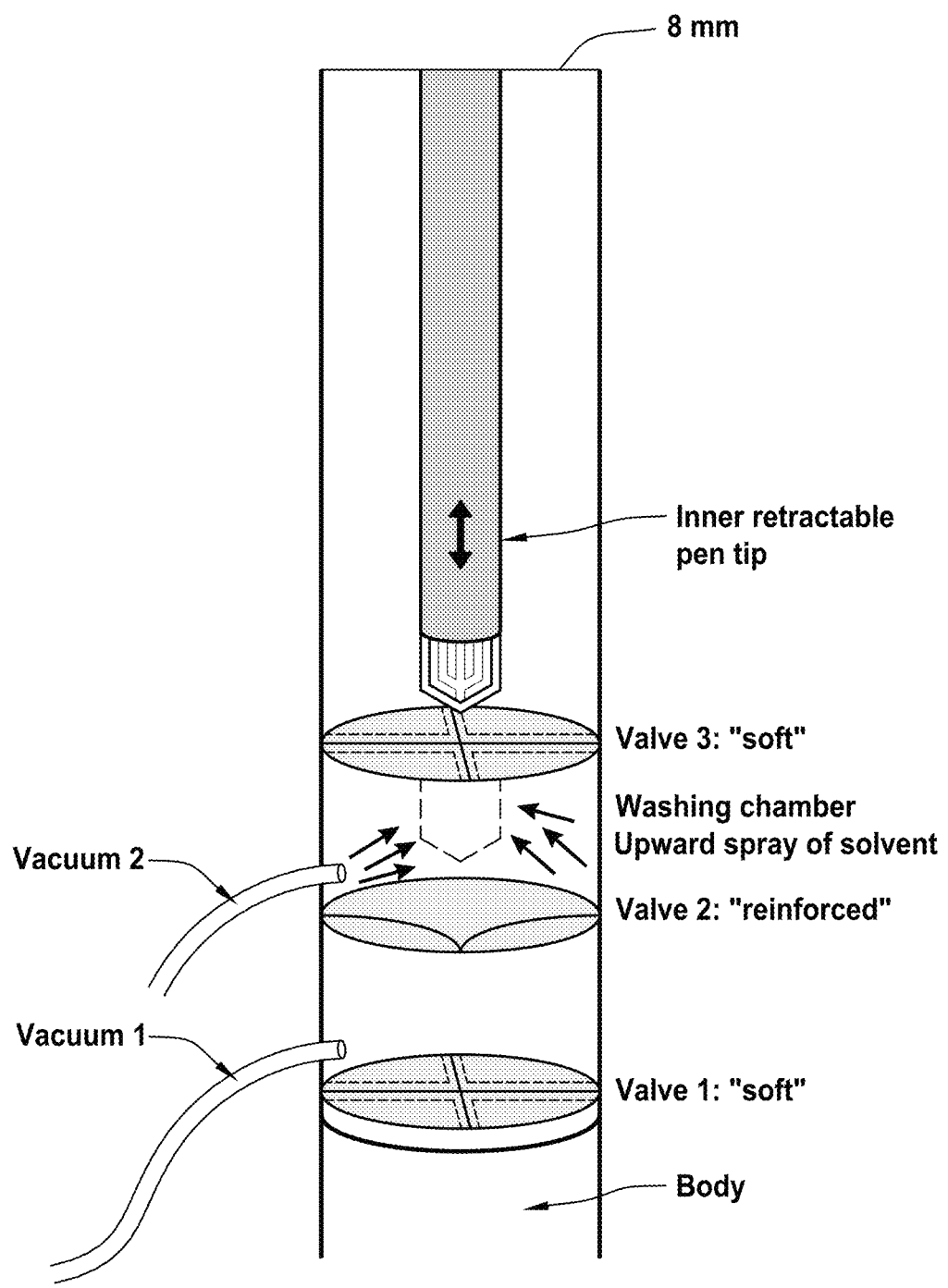
FIG. 15: Diagram of washing chamber for minimally invasive mass spectrometry probe.

The probe may be washed between analyses in a variety of methods. Generally, the tip of the probe is wiped with sterile water. An additional design that can facilitate the washing step is a retractable design that will wash the exterior of the probe without having to remove the device from the patient (FIG. 15). The design consists of a chamber with valves located at the openings to maintain a water and gas seal. A longer tube that contains the probe tip, water, and gas conduits will transect only the top valve when the tip is located in the washing chamber, but will pass through both valves when the tip is deployed into the patient environment. After the probe tip, tubing, or both have become contaminated during the surgery process, the probe will withdraw into the washing chamber. Water tubes can be located inside the washing chamber and point upwards providing a strong jet of cleaning solvent. Two positions of vacuum tubing will be located above the first and second valve to remove dirtied solvent. The vacuum tube placed above the first valve is an emergency tube in case any water breaks the first valve barrier. The entire system will fit smoothly inside of a trocar, and the deployable probe will be located inside of this system. The vacuums located inside the probe will also operate during this cleaning process, which will flush the tubing until clean.

Example 2—Molecular Profiles and Analysis

The system described herein operates by directly connecting the transfer tube to the mass spectrometer inlet for transporting the analyte-containing solvents to the mass spectrometer for molecular analysis. This set up greatly simplifies operational details and precludes the use of ionization sources. After the probe interacts with the tissue, the solvent is then transported to the mass spectrometer and directly infused without the need of an additional ionization source. Since the system is fully automated so that each 10 µL solvent droplet is delivered separately to the inlet, the mass spectrometer operates without any impact on its performance. Rich molecular information is obtained in this manner, similar to what is observed from other solvent-extraction ambient ionization techniques such as desorption electrospray ionization. The ionization mechanism may be similar to inlet ionization. For inlet ionization methods, the ionization occurs in the inlet pressure drop region between atmosphere and vacuum. Because of the nature of minimally invasive surgical techniques, the diameter of tubing, and length of tubing is of critical importance. A variety of tube lengths were tested for the delivery of solvent to the mass spectrometer, as seen in FIGS. 5-8).

Figure 11:
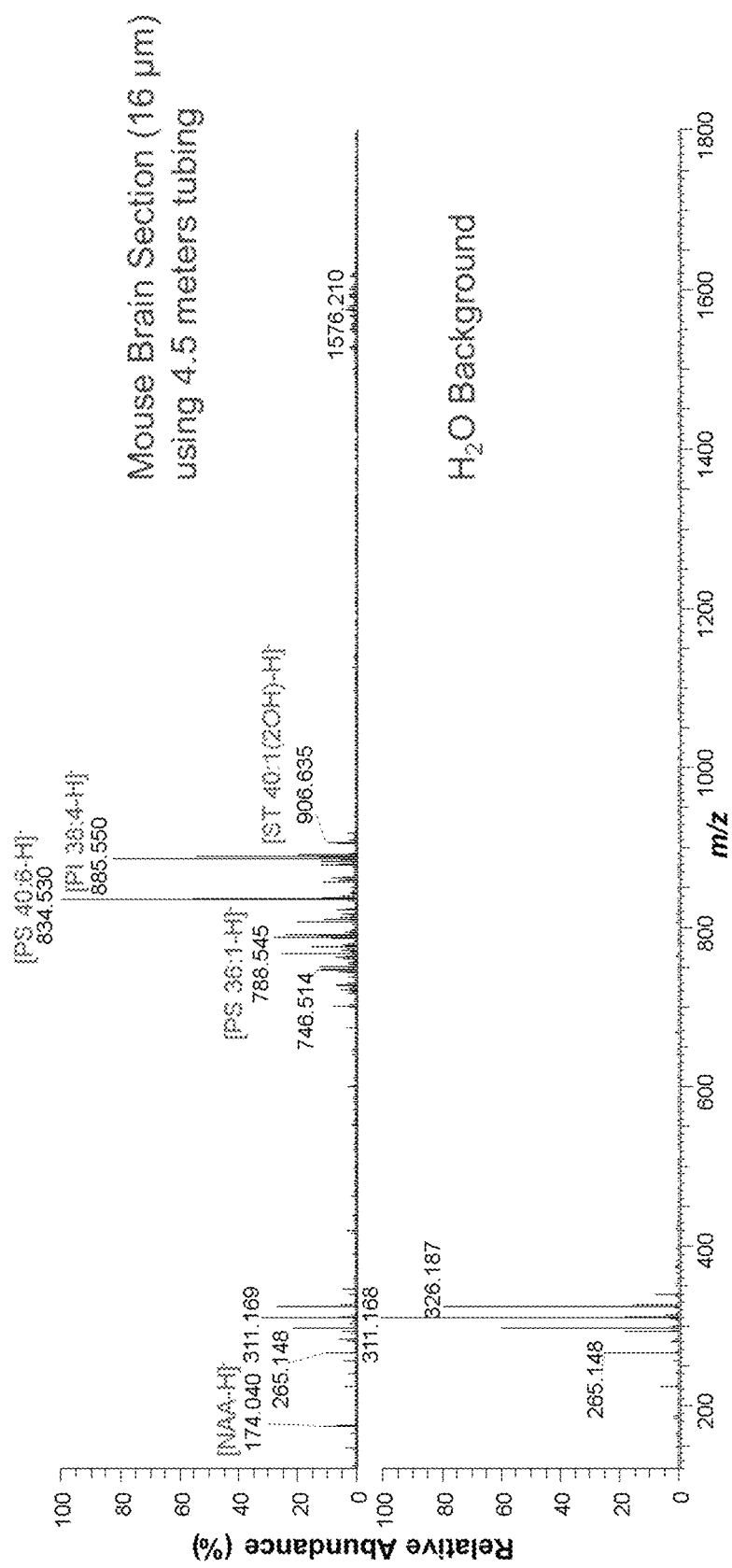
FIG. 11: Mass spectra generated from a 16 μm mouse brain section using 4.5 meter long tubing compared to the water background.
Figure 12:
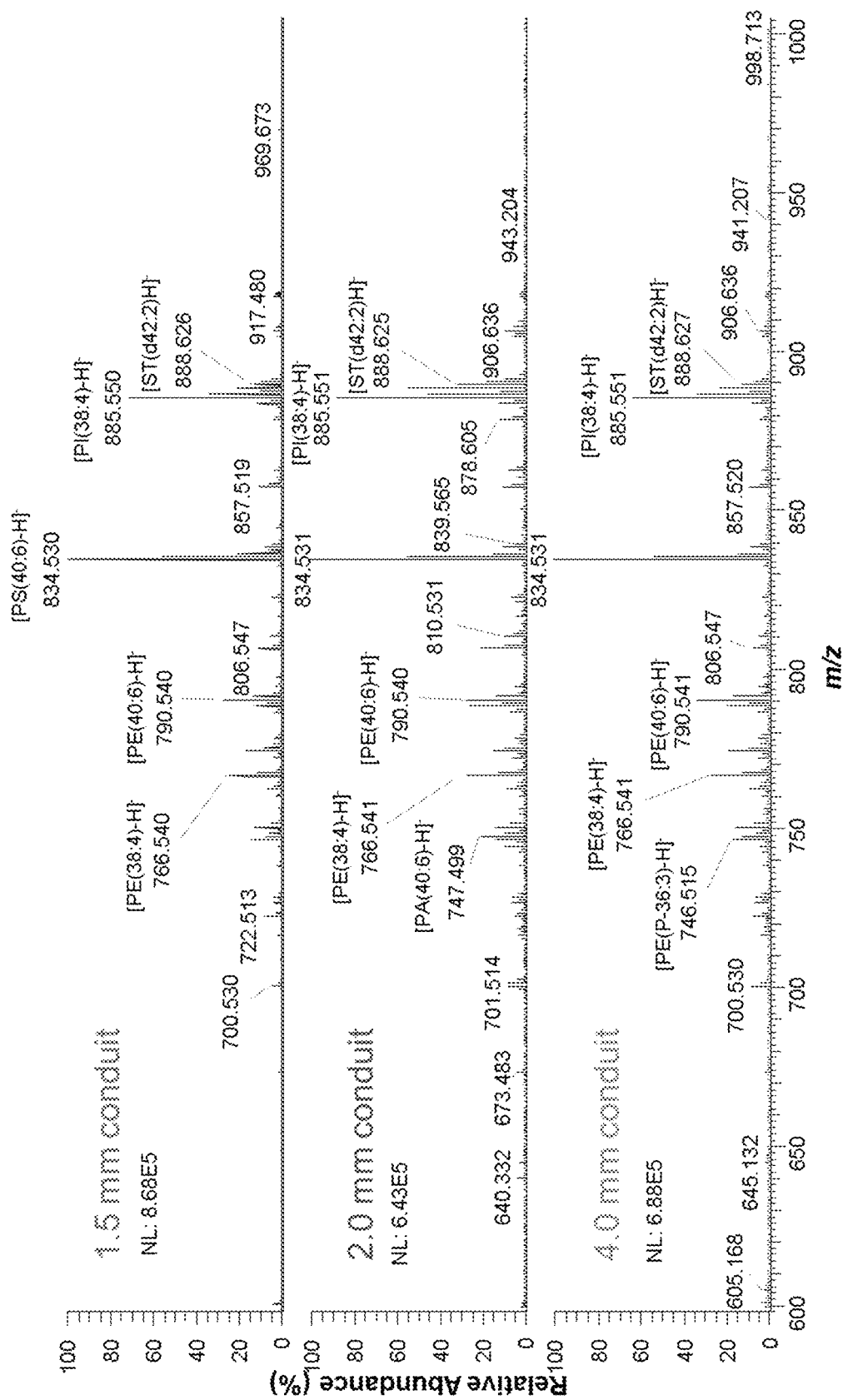
FIG. 12: Mass spectra generated with the minimally invasive mass spectrometry probe using Q Exactive Orbitrap Mass Spectrometer and conduits of 1.5-4.0 mm diameter.
Figure 14:
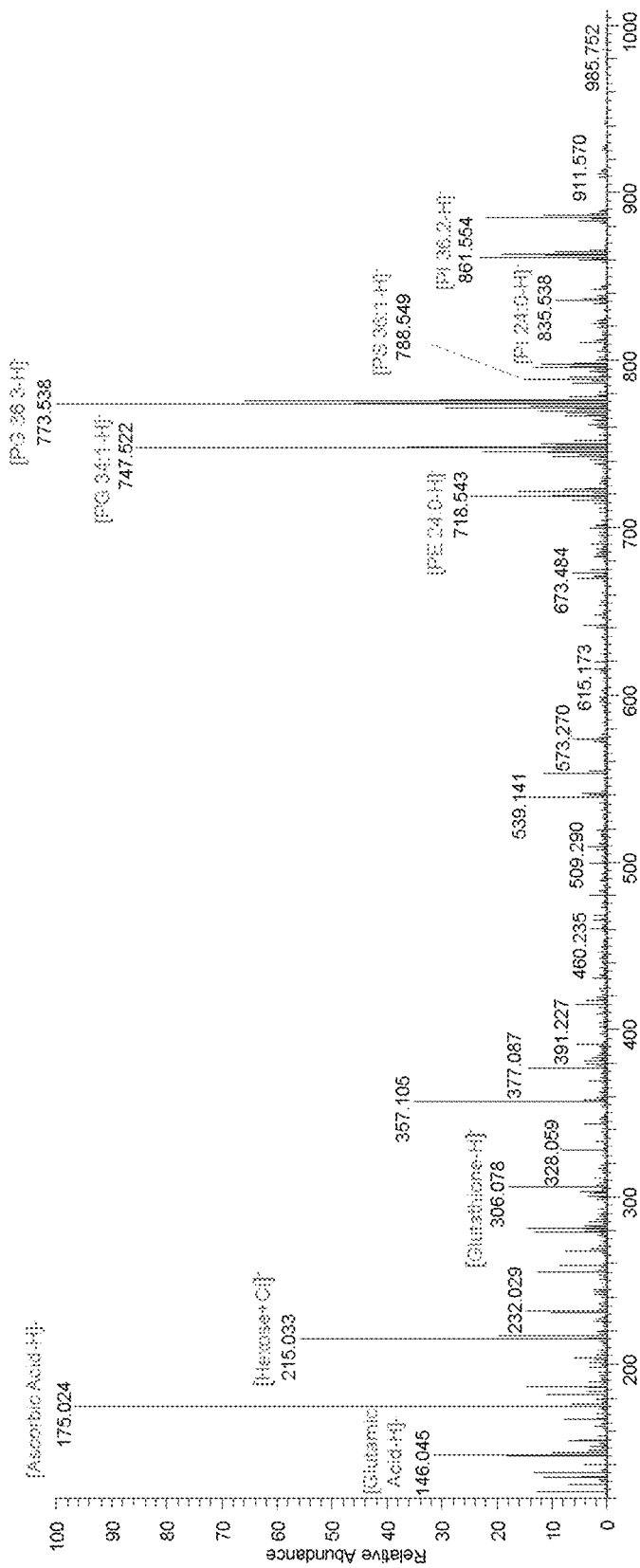
FIG. 14: Mass spectra of human lung tissue section from the minimally invasive mass spectrometry probe using Q Exactive Orbitrap Mass Spectrometer.

FIGS. 5-8 show the total ion chromatograms obtained from mouse brain sections during the total analysis period while using tubing lengths of 1.5 meters up to 4.5 meters. Rich molecular profiles were observed in all cases. At a tube length of 4.5 meters the molecular profile is easily established over the background signal of the water (FIG. 11). FIG. 12 shows total ion chromatograms obtained using conduit sizes from 1.5 mm to 4.0 mm. Again, rich molecular profiles were observed with each conduit size. To further demonstrate the utility of the minimally invasive probe for mass spectrometry, human lung tissue was analyzed (FIG. 14), and generated a robust molecular profile.

The molecular profiles generated by the minimally invasive mass spectrometry probe can also be used for tissue typing. A series of tissue samples were evaluated with the minimally invasive mass spectrometry probe and were able to be identified with an overall accuracy of 98.55% (Table 1).

TABLE 1

| Tissue typing results. | | | | | | | |
|---|---|---|---|---|---|---|---|
| TRUE | Thyroid | Lymph | Parathyroid | Breast | Lung | Ovarian | Pancreas |
| Thyroid | 42 | 0 | 1 | 0 | 0 | 0 | 0 |
| Lymph | 0 | 26 | 0 | 0 | 0 | 0 | 0 |
| Parathyroid | 0 | 1 | 62 | 0 | 0 | 0 | 0 |

TABLE 1-continued

Tissue typing results.

| TRUE | Thyroid | Lymph | Parathyroid | Breast | Lung | Ovarian | Pancreas |
|---|---|---|---|---|---|---|---|
| Breast | 0 | 0 | 0 | 29 | 0 | 0 | 0 |
| Lung | 0 | 0 | 0 | 0 | 47 | 0 | 0 |
| Ovarian | 0 | 1 | 0 | 1 | 0 | 41 | 0 |
| Pancreas | 0 | 0 | 0 | 0 | 0 | 0 | 24 |

The system was able to identify lymph, breast, and lung tissues with 100% accuracy, thyroid and parathyroid with between 97% and 99% accuracy, ovarian with 95.35% accuracy, and pancreas tissue with 83.33% accuracy. These tissue typing results were generated from selected features of the mass spectrometry profiles shown in Table 2.

TABLE 2

Selected features for tissue typing.

| m/z | Thyroid | Lymph | Parathyroid | Breast | Lung | Ovarian | Pancreas |
|---|---|---|---|---|---|---|---|
|  | −0.25915 | −1.37199 | 0.833471 | −0.44036 | −0.34999 | 2.269018 | −0.68101 |
| 125.01 | 0 | 0 | 0 | 0 | 0 | 0.097137 | 0 |
| 130.06 | 0 | 0 | 0.008242 | 0 | 0 | 0 | 0 |
| 146.05 | 0 | 0 | −0.00177 | 0 | 0 | 0 | 0 |
| 147.69 | 0 | 0 | 0.28651 | 0 | 0 | 0 | 0 |
| 148.95 | 0 | 0 | 0 | 0 | 0 | 0.025703 | 0 |
| 183.96 | 0 | 0 | 0 | 0 | 0 | 0.014118 | 0 |
| 191.02 | 0 | 0 | 0 | 0 | 0 | −0.01003 | 0 |
| 194.99 | 0 | 0 | 0 | 0 | 0.00062 | 0 | 0 |
| 200.17 | 0 | −0.00053 | 0 | 0 | 0 | 0 | 0 |
| 205.46 | 0 | 0 | 0 | 0 | 0 | 0 | 0.260268 |
| 218.1 | 0 | 0 | −0.01171 | 0 | 0 | 0 | 0 |
| 239.17 | 0 | −0.02264 | 0 | 0 | 0 | 0 | 0 |
| 241.92 | 0 | 0 | 0 | 0 | 0 | 0.00716 | 0 |
| 243.97 | 0 | 0 | −0.01202 | 0 | 0 | 0 | 0 |
| 244.92 | 0 | 0 | 0.004177 | 0 | 0 | 0 | 0 |
| 250.96 | 0.064681 | 0 | 0 | 0 | 0 | 0 | 0 |
| 251.96 | 0 | 0 | 0 | 0 | 0 | 0.030521 | 0 |
| 252.85 | 0 | 0.00771 | 0 | 0 | 0 | 0 | 0 |
| 255.9 | 0 | 0 | 0 | 0 | 0 | 0.032836 | 0 |
| 256.23 | 0 | 0 | 0 | 0 | 0.009842 | 0 | 0 |
| 271 | 0 | 0 | −0.0484 | 0 | 0 | 0 | 0 |
| 271.19 | 0 | −0.00793 | 0 | 0 | 0 | 0 | 0 |
| 272.01 | 0 | 0 | 0.042591 | 0 | 0 | 0 | 0 |
| 273.08 | 0 | 0 | 0.015766 | 0 | 0 | 0 | 0 |
| 276.8 | 0.014438 | 0 | 0 | 0 | 0 | 0 | 0 |
| 279.24 | 0 | 0 | 0 | 0 | 0.011053 | 0 | 0 |
| 279.92 | 0 | 0 | 0 | 0 | −0.03074 | 0 | 0 |
| 287.01 | 0 | 0 | 0 | 0 | 0 | 0.026693 | 0 |
| 287.98 | 0 | 0 | 0.131242 | 0 | 0 | 0 | 0 |
| 291.01 | 0 | 0.081933 | 0 | 0 | 0 | 0 | 0 |
| 294.82 | 0 | 0 | −0.01746 | 0 | 0 | 0 | 0 |
| 296.09 | 0 | 0 | −0.01414 | 0 | 0 | 0 | 0 |
| 296.94 | 0 | 0 | 0 | 0 | 0 | 0 | 0.105634 |
| 306.07 | 0 | 0 | 0 | 0 | 0.016765 | 0 | 0 |
| 318.85 | 0 | 0 | 0 | 0 | 0 | 0.004345 | 0 |
| 323.91 | 0 | 0 | 0 | 0 | 0 | 0.025689 | 0 |
| 326.06 | 0 | 0 | 0.031889 | 0 | 0 | 0 | 0 |
| 332.27 | 0 | 0 | 0 | 0 | 0 | 0.064138 | 0 |
| 341.27 | 0 | 0 | 0 | 0.01519 | 0 | 0 | 0 |
| 344.97 | 0 | 0 | 0 | 0 | 0 | 0.066306 | 0 |
| 354.16 | 0 | 0 | 0 | 0 | 0 | −0.04315 | 0 |
| 357.84 | 0 | 0 | 0 | 0 | 0 | 0.011447 | 0 |
| 362.24 | 0 | 0 | −0.07847 | 0 | 0 | 0.000379 | 0 |
| 407.23 | 0 | 0 | 0 | 0 | 0 | −0.00779 | 0 |
| 428.03 | 0 | 0.089313 | 0 | 0 | 0 | 0 | 0 |
| 428.19 | 0 | 0 | 0 | 0 | 0 | −0.00888 | 0 |
| 436.28 | 0 | 0 | 0 | 0 | 0 | 0 | 0.006734 |
| 437.29 | 0 | 0 | 0 | 0 | 0 | 0 | 0.077554 |
| 444.08 | 0.151553 | 0 | 0 | 0 | 0 | 0 | 0 |
| 453.28 | 0 | 0 | 0 | 0 | 0 | −0.00176 | 0 |

TABLE 2-continued

Selected features for tissue typing.

| | Thyroid | Lymph | Parathyroid | Breast | Lung | Ovarian | Pancreas |
|---|---|---|---|---|---|---|---|
| 455.8 | 0 | 0 | 0 | 0 | 0 | 0.01032 | 0 |
| 460.23 | 0 | 0 | 0 | 0 | 0 | −0.04105 | 0 |
| 462.3 | 0 | 0 | 0 | 0 | 0 | 0 | 0.08139 |
| 463.98 | 0 | 0 | 0.024299 | 0 | 0 | 0 | 0 |
| 465.3 | 0 | 0 | 0 | 0 | 0 | −0.03072 | 0 |
| 465.32 | 0 | 0 | 0 | 0 | 0 | 0 | 0.012348 |
| 476.21 | 0 | 0 | −0.02093 | 0 | 0 | 0 | 0 |
| 485.2 | 0 | 0 | 0 | 0 | 0 | 0.032981 | 0 |
| 519.32 | 0 | 0 | 0 | 0.181706 | 0 | 0 | 0 |
| 524.3 | 0 | 0 | 0 | 0 | 0 | 0 | 0.0418 |
| 530.26 | 0 | 0 | 0.011799 | 0 | 0 | 0 | 0 |
| 535.13 | 0 | 0 | 0 | 0 | 0 | 0.041376 | 0 |
| 565.05 | 0 | 0 | 0.076194 | 0 | 0 | 0 | 0 |
| 578.27 | 0 | 0.067343 | 0 | 0 | 0 | 0 | 0 |
| 616.17 | 0 | 0 | 0 | 0 | 0 | −0.03131 | 0 |
| 637.33 | 0.100992 | 0 | 0 | 0 | 0 | 0 | 0 |
| 655.51 | 0 | 0 | 0 | 0 | 0 | 0 | 0.088267 |
| 688.51 | 0 | 0 | 0 | 0.064253 | 0 | 0 | 0 |
| 690.51 | 0 | 0 | 0 | 0 | 0.044558 | 0 | 0 |
| 701.53 | 0 | 0 | 0 | 0 | 0 | −0.00473 | 0 |
| 714.51 | 0 | 0 | 0 | 0 | 0 | −0.02904 | 0 |
| 715.54 | 0 | 0 | 0 | 0.286059 | 0 | 0 | 0 |
| 717.53 | 0 | 0 | 0.032346 | 0 | 0 | 0 | 0 |
| 718.54 | 0 | 0 | 0 | 0 | 0.107471 | 0 | 0 |
| 719.49 | 0 | 0 | 0 | 0 | 0.166554 | 0 | 0 |
| 721.5 | 0 | 0 | 0 | 0 | 0.019482 | 0 | 0 |
| 724.99 | 0 | 0 | 0.012692 | 0 | 0 | 0 | 0 |
| 725.49 | 0 | 0 | 0.061029 | 0 | 0 | 0 | 0 |
| 726.5 | 0 | 0 | 0.022406 | 0 | 0 | 0 | 0 |
| 729.37 | 0 | 0.077857 | 0 | 0 | 0 | 0 | 0 |
| 741.53 | 0 | 0 | 0.04295 | 0 | 0 | 0 | 0 |
| 743.57 | 0 | 0 | 0 | 0.023627 | 0 | 0 | 0 |
| 747.52 | 0 | 0 | 0 | 0 | 0 | −0.0096 | 0 |
| 748.52 | 0 | 0 | 0 | 0 | 0.140912 | 0 | 0 |
| 752.56 | 0 | 0 | 0 | 0 | 0.022913 | 0 | 0 |
| 758.4 | 0.0479 | 0 | 0 | 0 | 0 | 0 | 0 |
| 761.4 | 0.025123 | 0 | 0 | 0 | 0 | 0 | 0 |
| 764.52 | 0 | 0 | 0.003296 | 0 | 0 | 0 | 0 |
| 768.55 | 0 | 0 | 0.002224 | 0 | 0 | 0 | 0 |
| 769.5 | 0 | 0 | 0 | 0 | 0 | −0.00431 | 0 |
| 769.51 | 0 | 0 | 0 | 0 | 0.004727 | 0 | 0 |
| 770.53 | 0 | 0 | 0 | 0 | 0.08501 | 0 | 0 |
| 771.52 | 0 | 0 | 0 | 0 | 0 | −0.03674 | 0 |
| 775.55 | 0 | 0 | 0 | 0 | 0 | −0.02396 | 0 |
| 776.55 | 0 | 0 | 0 | 0 | 0.121705 | 0 | 0 |
| 793.56 | 0 | 0.012003 | 0 | 0 | 0 | 0 | 0 |
| 795.52 | 0 | 0 | 0 | 0 | 0.039051 | 0 | 0 |
| 796.52 | 0 | 0 | 0 | 0 | 0.024792 | 0 | 0 |
| 809.52 | 0 | 0 | 0.063972 | 0 | 0 | 0 | 0 |
| 811.53 | 0 | 0.047294 | 0 | 0 | 0 | 0 | 0 |
| 812.55 | 0 | 0.087882 | 0 | 0 | 0 | 0 | 0 |
| 813.55 | 0 | 0.031647 | 0 | 0 | 0 | 0 | 0 |
| 822.47 | 0.062048 | 0 | 0 | 0 | 0 | 0 | 0 |
| 823.48 | 0.215822 | 0 | 0 | 0 | 0 | 0 | 0 |
| 833.52 | 0 | −0.0026 | 0 | 0 | 0 | 0 | 0 |
| 835.54 | 0 | −0.00055 | 0 | 0 | 0 | 0 | 0 |
| 836.55 | 0 | 0.311816 | 0 | 0 | 0 | 0 | 0 |
| 838.56 | 0 | 0.020823 | 0 | 0 | 0 | 0 | 0 |
| 860.54 | 0 | 0 | 0 | 0.004644 | 0 | 0 | 0 |
| 861.55 | 0 | 0 | 0 | 0 | 0 | −0.02476 | 0 |
| 991.29 | 0 | 0.001467 | 0 | 0 | 0 | 0 | 0 |
| 991.69 | 0 | 0.069562 | 0 | 0 | 0 | 0 | 0 |
| 1305.95 | 0 | 0 | 0 | 0 | 0 | 0.058809 | 0 |
| 1448.97 | 0 | 0 | 0.002613 | 0 | 0 | 0 | 0 |

Similarly to the differentiation of tissue types, the minimally invasive mass spectrometry probe can be used to differentiate between normal and cancerous tissues. The system predicted normal tissues with greater than 89% accuracy, and cancer tissues with greater than 91% accuracy as seen in Table 3.

TABLE 3

Cancer tissue prediction results.

|      |        | Predicted |        |
|------|--------|-----------|--------|
|      |        | Normal    | Cancer |
| True | Normal | 247       | 28     |
|      | Cancer | 12        | 129    |

These tissues were predicted based on the selected features shown in Table 4.

TABLE 4

Selected features used for the prediction of cancer tissues.

| m/z    | Cancer       | MaxIntensityNorm | MinIntensityNorm | MaxIntensity | MinIntensity |
|--------|--------------|------------------|------------------|--------------|--------------|
|        | −0.1200838   | 0.00000000       | 0                | 0.0          | 0            |
| 124.01 | −40.9603959  | 0.07309089       | 0                | 1910468.9    | 0            |
| 146.05 | −25.4909642  | 0.08721183       | 0                | 4249182.8    | 0            |
| 154.06 | −1.7548952   | 0.27268945       | 0                | 1028115.5    | 0            |
| 165.02 | 42.8950874   | 0.02168110       | 0                | 189918.4     | 0            |
| 174.04 | 114.2977347  | 0.01893967       | 0                | 703388.7     | 0            |
| 175.02 | −27.1843207  | 0.21139870       | 0                | 6752479.6    | 0            |
| 175.03 | −24.4596324  | 0.12211639       | 0                | 2175467.9    | 0            |
| 187.04 | −60.8607370  | 0.22046140       | 0                | 5731647.5    | 0            |
| 201.04 | 118.9618023  | 0.08163593       | 0                | 1262331.3    | 0            |
| 214.05 | −128.8755917 | 0.03867785       | 0                | 773249.9     | 0            |
| 215.03 | −31.7356346  | 0.09055005       | 0                | 3274645.3    | 0            |
| 221.01 | 138.9164198  | 0.01083151       | 0                | 568690.6     | 0            |
| 241.04 | −74.5285436  | 0.01626196       | 0                | 3302753.8    | 0            |
| 246.95 | −2.9550154   | 0.05776215       | 0                | 1111366.1    | 0            |
| 267.07 | 4.3468095    | 0.03979236       | 0                | 4039159.9    | 0            |
| 268.8  | −51.7317355  | 0.04524576       | 0                | 1488145.8    | 0            |
| 271    | −3.2679671   | 0.06004618       | 0                | 492594.7     | 0            |
| 283.27 | −55.5183712  | 0.14933261       | 0                | 2355024.1    | 0            |
| 296.94 | 7.5951233    | 0.22379688       | 0                | 2429905.2    | 0            |
| 313.16 | −3.7134875   | 0.17606736       | 0                | 7786035.2    | 0            |
| 328.06 | 71.2579706   | 0.04428292       | 0                | 957525.7     | 0            |
| 332.9  | 23.4374773   | 0.03396153       | 0                | 1214185.0    | 0            |
| 341.27 | −1.6023939   | 0.28304768       | 0                | 6590254.4    | 0            |
| 345.16 | −50.1650411  | 0.04368856       | 0                | 1696500.0    | 0            |
| 346.05 | 83.1031168   | 0.01781918       | 0                | 628038.1     | 0            |
| 353.16 | 23.4132756   | 0.06995437       | 0                | 2172310.7    | 0            |
| 377.09 | −9.9688497   | 0.10964367       | 0                | 1100627.9    | 0            |
| 559.47 | −2.7064435   | 0.05334380       | 0                | 49840406.6   | 0            |
| 572.48 | 83.3837979   | 0.01727858       | 0                | 1439590.6    | 0            |
| 585.49 | −20.0678254  | 0.09010271       | 0                | 86114572.9   | 0            |
| 615.17 | −115.9821356 | 0.03578691       | 0                | 2801168.1    | 0            |
| 722.51 | 66.9597188   | 0.04599428       | 0                | 13448313.9   | 0            |
| 742.54 | 89.8907769   | 0.04732031       | 0                | 8284542.5    | 0            |
| 744.55 | 64.7272067   | 0.02038387       | 0                | 905261.7     | 0            |
| 748.52 | −39.0756981  | 0.04027318       | 0                | 1870669.2    | 0            |
| 766.54 | −23.4133796  | 0.05266494       | 0                | 4504433.6    | 0            |
| 773.53 | −60.0910994  | 0.09127090       | 0                | 3784388.4    | 0            |
| 788.54 | 44.1054014   | 0.04591038       | 0                | 1660366.4    | 0            |
| 788.55 | −1.4204710   | 0.03125159       | 0                | 4032842.0    | 0            |
| 822.47 | −19.2490565  | 0.05601076       | 0                | 738427.0     | 0            |
| 823.48 | −66.6013083  | 0.02864992       | 0                | 320932.5     | 0            |
| 861.55 | −135.4621348 | 0.05829841       | 0                | 9614626.2    | 0            |
| 885.55 | 25.0244403   | 0.12046562       | 0                | 9712708.6    | 0            |
| 888.57 | 90.5815624   | 0.02339633       | 0                | 1145858.3    | 0            |

To evaluate the system performance, consecutive analysis was conducted on the same tissue section, and on different tissue sections to demonstrate that the system is highly reproducible within samples and across different samples.

Materials and Methods.

Mass Spectrometer. Q Exactive Hybrid Quadrupole-Orbitrap mass spectrometer (Thermo Scientific, San Jose, Calif.) was used. Full-scan was carried out at the range of m/z 500-1800, and the other mass spectrometric parameters were listed as follows: resolving power 140,000, micro scan 2, maximum injection time 300 ms, capillary temperature 350° C. and S-lens RF level 100.

Biological Tissues. Wild-type mouse brains were purchased from Bioreclamation IVT. 62 frozen human tissue specimens including breast, thyroid, lymph node, ovarian, and kidney were obtained from Cooperative Human Tissue Network and Baylor College Tissue Bank. Samples were stored in a −80° C. freezer. Tissue slides were sectioned at 16 μm using a CryoStar™ NX50 cryostat. Frozen tissue specimen were thawed under room temperature before use.

Statistical Analysis. IBM SPSS Statistics 22.0 (IBM Corporation, Armonk, N.Y., USA) was used to perform principal component analysis (PCA) to reveal patterns in the data. The analysis was performed directly using the raw data. The 10 peaks of the top relative intensities in the m/z range of 700-900 were used for PCA. Typically, the first three components, which all encompassed more than 85% of the total variance, are used in the present results.

Example 3—System Automation for Handheld and Laparoscopic Use

Because all the materials (PDMS and PTFE) and solvent (only water) used in the minimally invasive probe design are biologically compatible, the system has a high potential to be used in laparoscopic and endoscopic surgeries for real-time analysis. More than that, due to the small dimension of the device, it can be integrated to a robotic surgical system, such as the Da Vinci surgical system, through an accessory port or one of its robotic arms. Several regions of the human body cavity can be quickly sampled during surgery with or without wash/flush steps in between each analysis, and analyzed by using a database of molecular signatures and machine learning algorithms. Therefore, the diagnosing results may be provided in real time for each sampled region. This system can be broadly used in a wide variety of oncological and other surgical interventions (such as endometriosis) for which real-time characterization and diagnosis of tissues are needed.

Figures 16A, 16B, 16C, 16D:
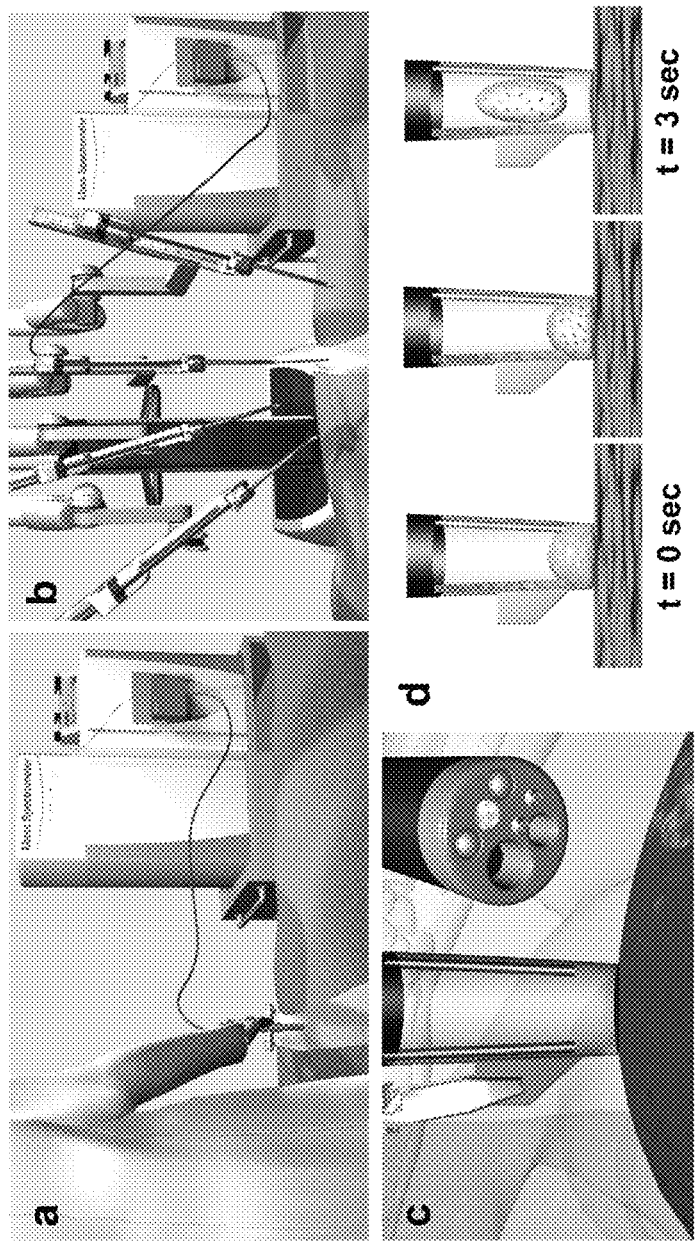
FIGS. 16A-16D: Schematic representation of the laparoscopic MasSpec Pen system being used in a (a) manual laparoscopic MIS procedure and (b) robotic assisted MIS. (c) The pen tip was designed with a grasping fin to allow manipulation and application of the MasSpec Pen using forceps or other graspers. (d) The tip contacts tissue for analysis and when the system is triggered (t=0 sec) by use of the foot pedal, the syringe pump delivers a controlled volume of water to the reservoir. The discrete water droplet interacts with the tissue to extract molecules. After 3 seconds, the vacuum and the gas conduits are concomitantly opened to transport the droplet from the MasSpec Pen to the mass spectrometer through the tubing system for molecular analysis.

Thus, a laparoscopic MasSpec Pen platform was developed, which may be used in manual or robotically controlled MIS procedures (FIGS. 16A and 16B). The laparoscopic MasSpec Pen platform was developed with emphasis on three main design features: 1) adherence to dimensions and material specifications necessary for use in the laparoscopic environment; 2) similar performance specification to the handheld MasSpec Pen to ensure compatibility with the previously generated statistical models; and 3) integration to an automated software and graphical user interface for real time data analysis and statistical classification.

Figures 17A, 17B, 17C:
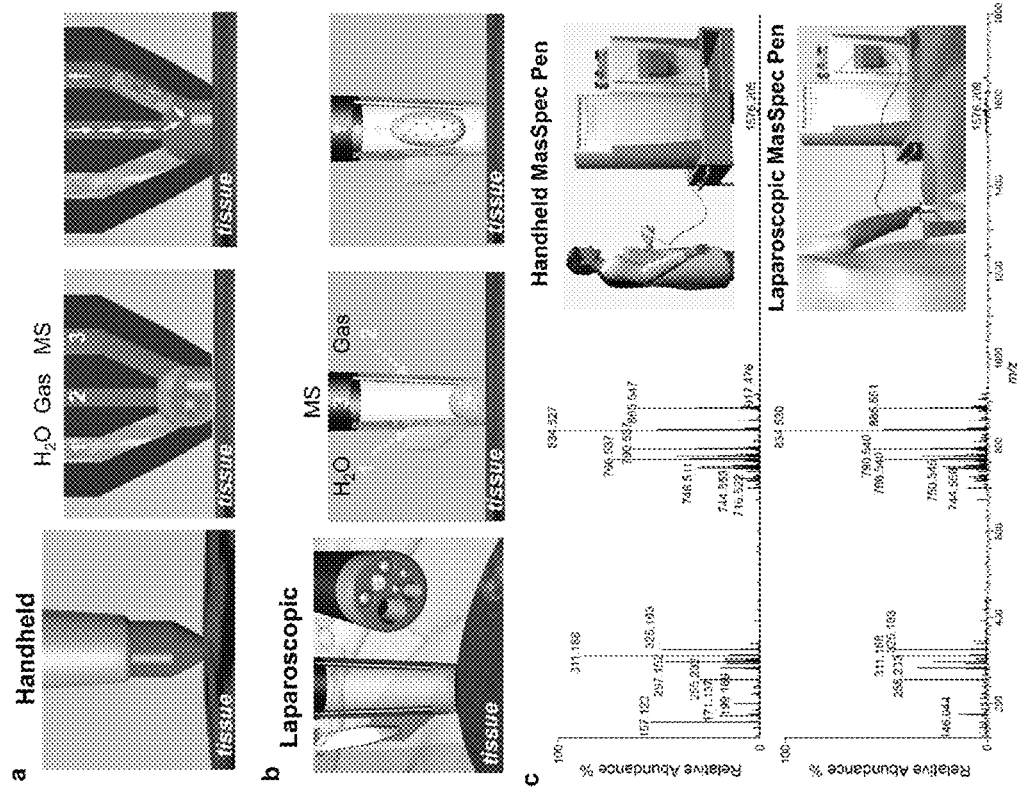
FIGS. 17A-17C: Comparison between designs and performance of the handheld and laparoscopic MasSpec Pen. (a) The handheld MasSpec Pen contains a PDMS tip and three PTFE conduits, which provide incoming water (1) and gas (2) to the tip, and an outgoing conduit (3) for the water droplet to the mass spectrometer. The pen tip holds a water droplet within the reservoir, which contacts tissue for analysis. (b) The laparoscopic MasSpec Pen PDMS tip is grafted with two micro-PTFE tubes, one for the incoming water (1), and another for incoming gas (2). The proximal end of the pen tip was then connected to a larger PTFE conduit, which functions as the outgoing water conduit (3). Using this design, the hollow space in the distal end of pen tip functions as the water droplet reservoir (c) Representative mass spectra obtained with the handheld and laparoscopic MasSpec Pen of a mouse brain tissue section, both operated at 2.7 mm reservoir diameter and a 1.5 meter tubing length.

The laparoscopic MasSpec Pen was engineered with the specifications needed to function in MIS. Design modifications allowed introduction of the MasSpec Pen through the cannula of a laparoscopic trocar, or through the open ports of robotic systems (commonly of 5 mm, 8 mm, or 12 mm in diameter), while maintaining similar operation to the handheld MasSpec Pen. The handheld MasSpec Pen has a diameter of 10 mm, which was dictated by the diameter of the 3D printed polydimethylsiloxane (PDMS) pen tip. The tip of the handheld MasSpec Pen was designed with three conduits (incoming water, incoming gas, and outgoing water), which are in fluid communication with an open reservoir that positions the water droplet for contact with tissue surface (FIG. 17A). In the laparoscopic MasSpec Pen, two micro-polytetrafluoroethylene (PTFE) tubes (OD 0.794 mm, ID 0.339 mm), one for the incoming water, and another for incoming gas, were grafted into a 3D printed PDMS tip (FIG. 17B). The proximal end of pen tip was connected to a larger PTFE conduit (OD 1.59 mm, ID 0.794 mm) to serve as the outgoing water conduit. In this design, the hollow space in the distal end of pen tip functions as the water droplet reservoir and can be customized to varied diameters depending on the intended use.

In this study, the reservoir was designed with three diameters of 1.5 mm, 2.7 mm, and 4.0 mm to display a range of capabilities. Although reservoir diameters below 1.5 mm could be manufactured via micromolding, these were not tested due to limitations in manufacturing capabilities. Further, current recommended cancer-free margins for solid cancer excision are often larger than 1.5 mm—such as 3 mm for basal cell carcinoma, 2 mm for breast cancer, and 5 cm for gastric cancer.

To manipulate the MasSpec Pen for contact with the organ of interest in vivo, a grasping fin was incorporated on the pen tip to provide an anchor point for a laparoscopic tool, such as forceps or a robotic arm (FIG. 16C). As in any laparoscopic procedure, organ access is dictated by trocar placement. One benefit of the laparoscopic MasSpec Pen is flexibility and light weight of the polymer-based tubing system. These features allow the device to be easily manipulated through a trocar in the x, y, and z directions given the cannula's placement in reference to an organ of interest. A 3 mm in length fin was incorporated into the 3D printed molds unilaterally at the proximal end of the pen tip to avoid increasing the diameter of the device. The total diameter of the laparoscopic MasSpec Pen including the fin was 7.5 mm for the 1.5 and 2.7 mm reservoir diameter tips, and 9.5 mm for the 4.0 mm reservoir diameter tip; all compatible for use through common sized trocars.

Different tube lengths between the laparoscopic MasSpec Pen and the mass spectrometer were investigated for use within the operating room environment (FIG. 18). Longer tubing lengths than those used in the handheld MasSpec Pen (1.5 m) were tested considering the additional length needed to insert the MasSpec Pen through the laparoscopic trocars (5-12 mm length), constraints of the operating room (OR) workspace, and the need for instrument placement outside of the surgical sterile field. As with the handheld MasSpec Pen, 3 seconds of contact time between the water droplet within the pen tip and the probed brain tissue section was used for molecular extraction (FIG. 16D).

Figures 18A, 18B, 18C:
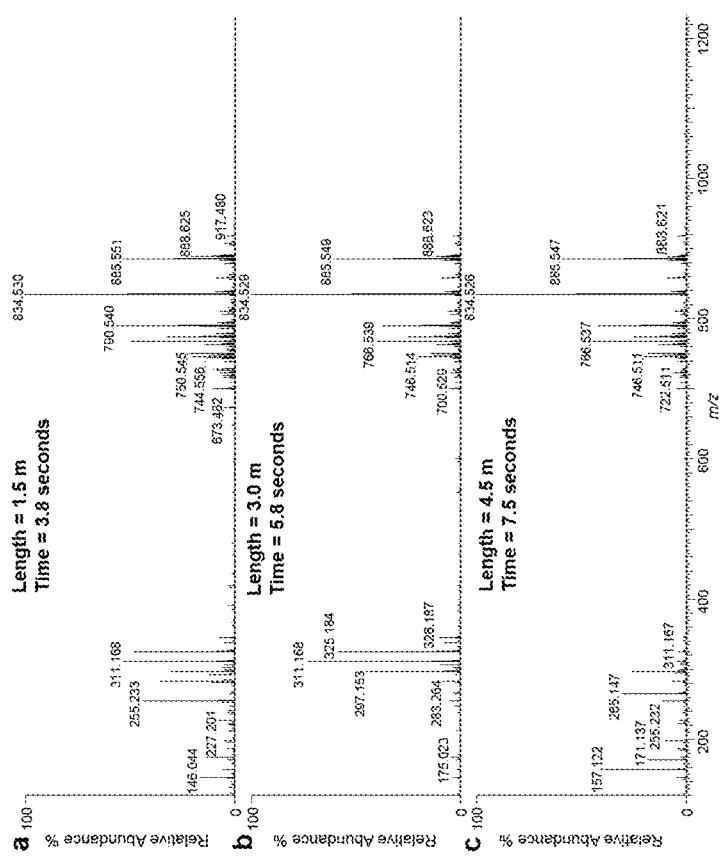
FIGS. 18A-18C: Different tubing lengths between the laparoscopic MasSpec Pen (2.7 mm reservoir diameter) and the mass spectrometer were evaluated using mouse brain tissue sections. Similar molecular profiles were obtained at different transfer times using (a) 1.5 m (3.8 seconds, n=10), (b) 3.0 m (5.8 seconds, n=10), and (c) 4.5 m (7.5 seconds, n=10).

After the sampling period, a 4-second water flush was used to facilitate droplet transport from the pen tip, through the PTFE tube, to the mass spectrometer. The PTFE tube was directly connected to an extended, heated mass spectrometer transfer tube (350° C.) via flexible silicon tubing, therefore eliminating the use of an external ionization source. Analyses were performed in the negative ion mode. FIGS. 18A-C show the mass spectra obtained from serial sections of mouse brain tissue analyzed with the 2.7 mm laparoscopic MasSpec Pen at 1.5 m, 3.0 m and 4.5 m tubing lengths. Similar patterns were observed in the recorded mass spectra, displaying high relative abundances of a variety of negatively charged ions, identified as lipid species typically observed from mouse brain tissue sections using MasSpec Pen and other ambient ionization techniques. For example, m/z 834.529 (identified as [PS(40:6)-H]$^-$), m/z 885.550 (identified as [PI(38:4)-H]$^-$), and m/z 790.539 (identified as [PE(40:6)-H]$^-$) were observed at high relative abundances in the mass spectra obtained from the grey matter of mouse brain.

Figures 20A, 20B, 20C:
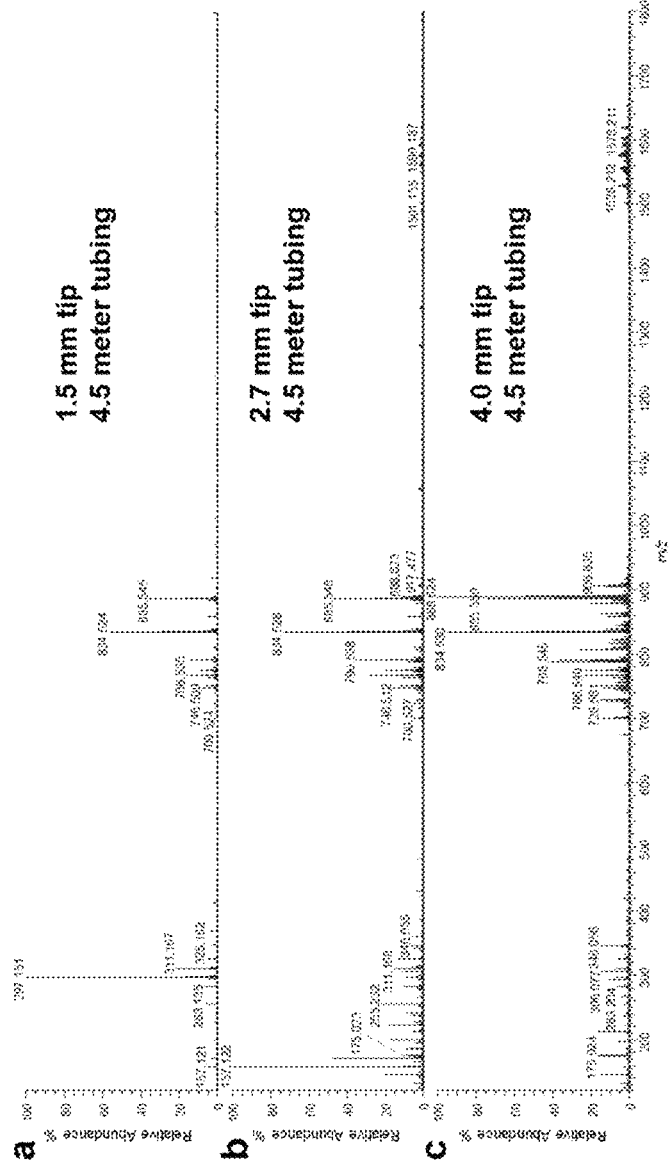
FIGS. 20A-20C: (a-c) Representative mass spectra obtained from mouse brain tissue sections with laparoscopic MasSpec Pen at reservoir diameters of 1.5, 2.7, and 4.0 mm and a 4.5 meter tubing length.

An average cosine similarity of 0.93 (n=12) was achieved for the mass spectra obtained with various tube lengths, which demonstrates that the molecular information obtained is reproducible and independent of tube length (Table 5). Additionally, transfer time was measured for each length tested, yielding 3.8 s±0.5 s (n=10), 5.8 s±0.7 s (n=10), and 7.5 s±0.4 s (n=10), for tube lengths of 1.5 m, 3.0 m, and 4.5 meters, respectively (Table 6). Interestingly, tripling the tube length from 1.5 m to 4.5 m resulted in doubling of the transfer time, which indicates a non-linear velocity of droplet transport in the tubing system. At a tube length of 4.5 meters, different laparoscopic MasSpec Pen reservoir diameters (1.5, 2.7, and 4.0 mm) were tested, yielding comparable performance with expected changes in the mass spectral profile due to sampling of different brain tissue regions (FIG. 20).

To compare the performance of the laparoscopic MasSpec Pen with that of the handheld system, serial tissue sections of mouse brain were analyzed using the same dimensions previously described for the handheld MasSpec Pen (2.7 mm pen tip diameter and 1.5 m tubing length). Similar profiles were observed from mouse brain tissue sections analyzed with both designs across the full m/z range (m/z 120-1800, cosine similarly=0.88, n=8) and restricted m/z range (m/z 600-1800, cosine similarly=0.92, n=8) (FIG. 17C). These results suggested that the laparoscopic MasSpec Pen produced comparable results to those obtained with the handheld MasSpec Pen, despite changes in reservoir design and tube length. A 2.7 mm reservoir diameter and 4.5 m tubing length were chosen for the remaining experiments performed with the laparoscopic MasSpec Pen. Using these parameters, an overall measurement time of ~20 seconds/spot was achieved, which includes the time employed for tissue sampling (3 seconds), droplet transport (7 seconds), and droplet ionization and analysis (~10 seconds).

Figures 19A, 19B:
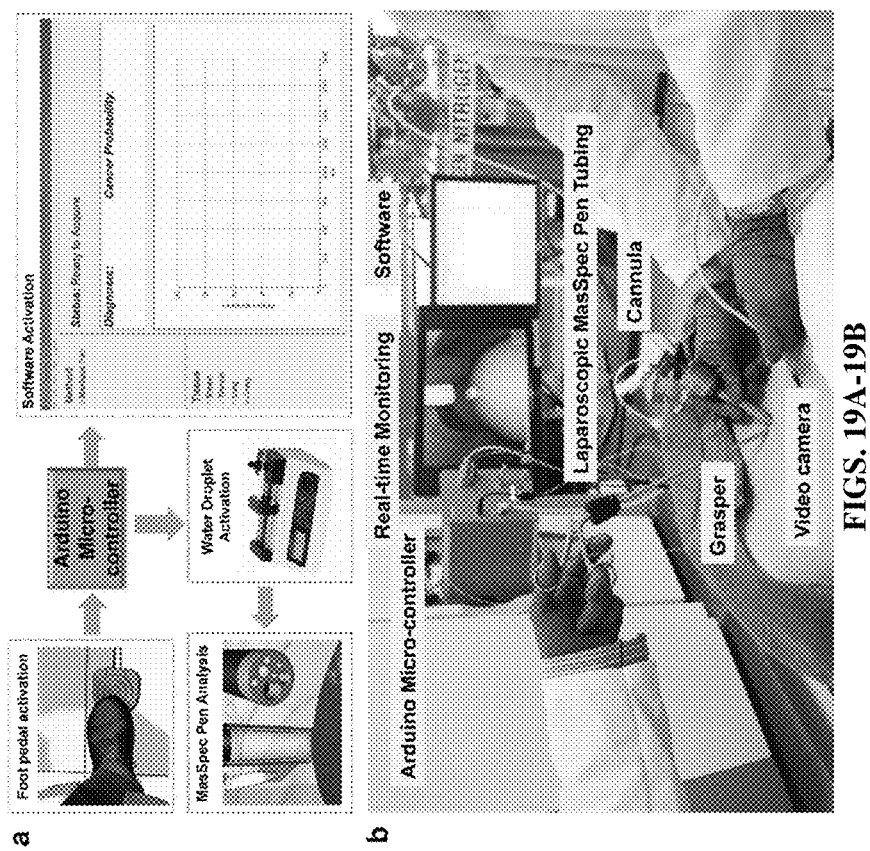
FIGS. 19A-19B: An automated system was developed for automatic mass spectrometry data acquisition, statistical analysis, and communication of results. (a) A foot pedal is used to trigger the analysis workflow through communication with an Arduino microcontroller, which then activates water droplet deposition by triggering the syringe pump. In the GUI, the user selects which type of tissue is being evaluated prior to usage, so that the software selects the proper statistical classifier, providing a predictive diagnosis with the associated cancer probability. (b) The laparoscopic MasSpec Pen platform was tested using a mannequin through an 8 mm cannula. Laparoscopic forceps were used to manipulate the MasSpec Pen, while a video camera was employed to transmit an image and/or video of the organs inside the abdomen and guide the operator during the procedure.

To facilitate clinical use of the laparoscopic MasSpec Pen, a software with a graphical user interface (GUI) was developed for real time mass spectrometry data acquisition, statistical analysis, and display of results. As previously reported for the handheld MasSpec Pen, a foot pedal is used to trigger the analysis workflow. Here, the system was further refined so that the foot pedal also triggers the lab-built software (FIG. 19A). Using this approach, the user selects which type of tissue is being evaluated in the GUI prior to tissue analysis, so that the software properly selects the corresponding statistical model for data analysis. Then, upon activation by the pedal, a syringe pump is triggered so that a discrete water droplet is formed in the pen tip, where it interacts with the tissue for 3 seconds. Following the tissue contact, the droplet enriched with extracted bio-molecular species is transported to the Orbitrap mass spectrometer through a PTFE tube for ionization and mass analysis, as previously explained. The mass spectra data is continuously recorded and read by the software program. The three mass spectra with the highest intensity for selected ions are averaged and pre-processed for statistical analysis. Prediction is then performed using the statistical models previously built by the Lasso method using data acquired from histologically validated tissues and the probability of the tissue being cancer is reported in the GUI.

Figure 21:
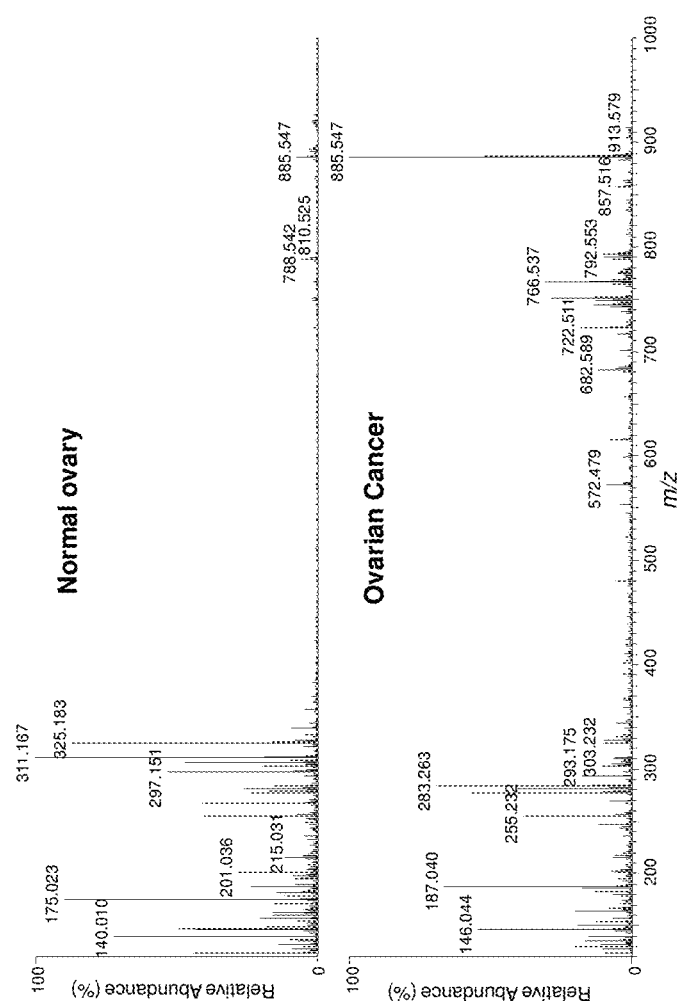
FIG. 21: Representative mass spectra obtained with the laparoscopic MasSpec Pen (2.7 mm reservoir diameter and a 4.5 meter tubing length) of a human normal and a cancerous ovarian tissues.
Figure 22:
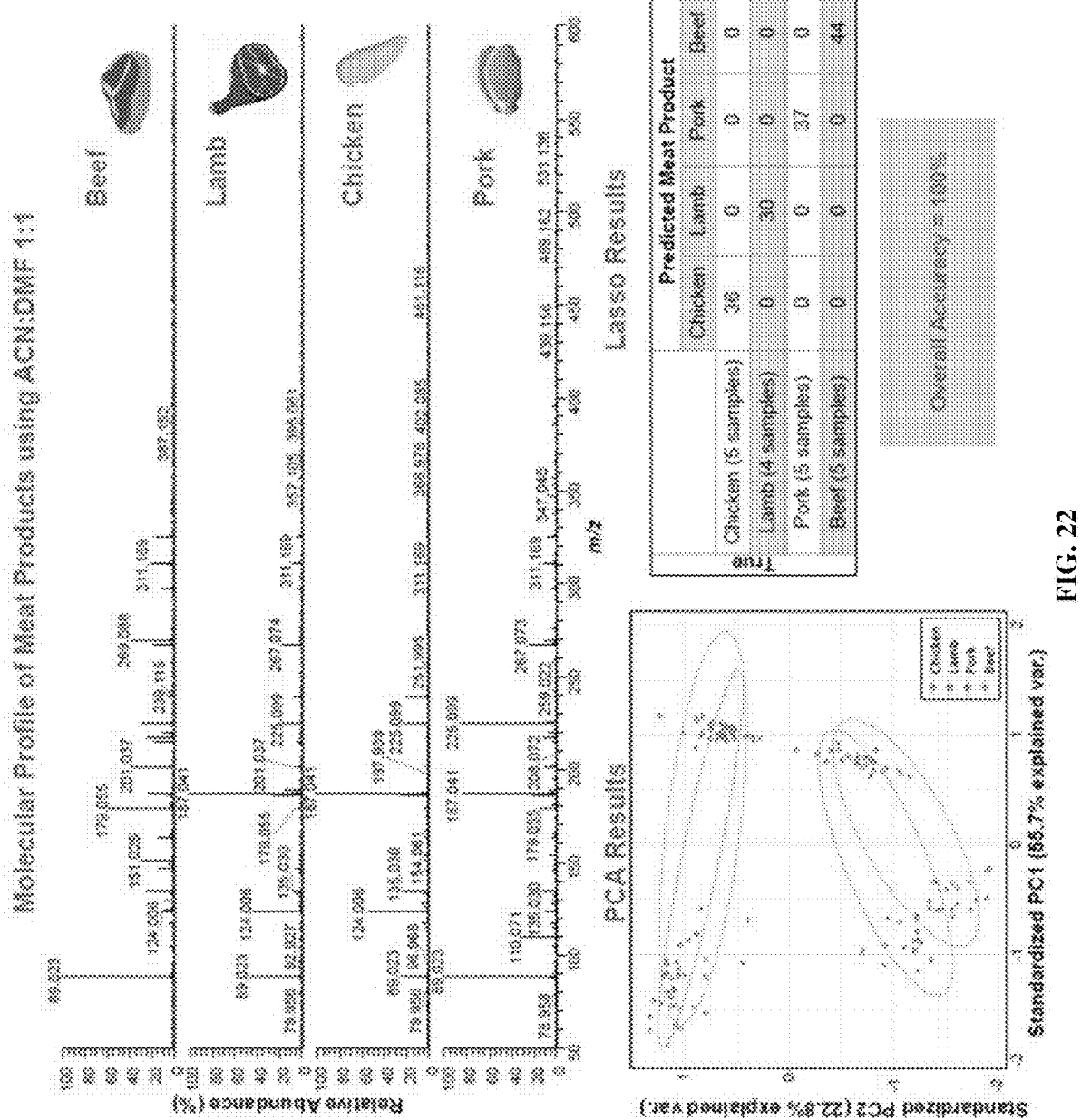
FIG. 22: Representative mass spectra obtained with the MasSpec Pen from samples of beef, lamb, chicken and pork using CAN:DMF 1:1 as the solvent. Results show that the spectra obtained using the MasSpec Pen were able to assess the source of the meat with a high level of accuracy.
Figure 23:
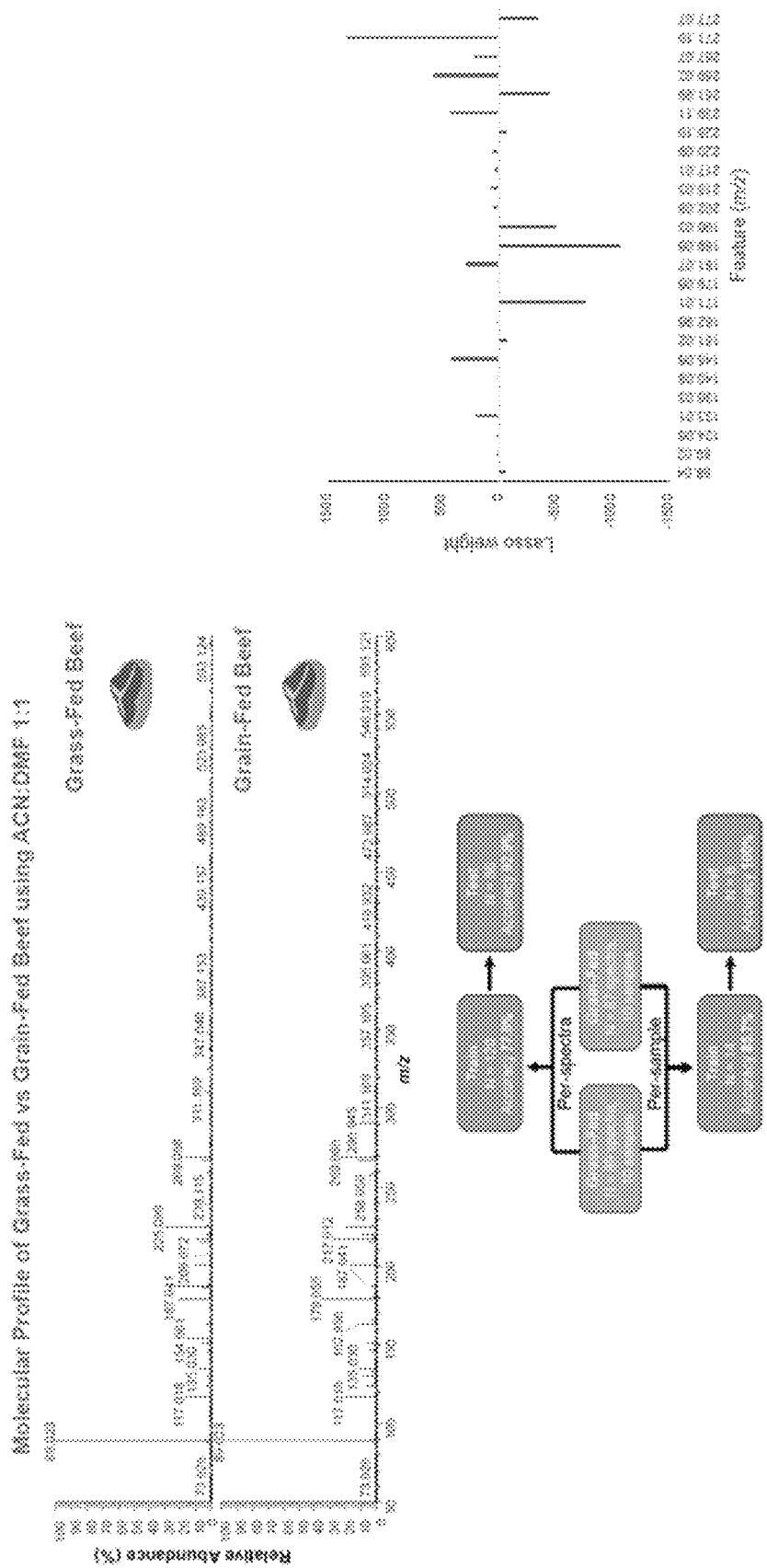
FIG. 23: Representative mass spectra obtained with the MasSpec Pen from samples of grass-fed versus grain-fed beef (using CAN:DMF 1:1 as the solvent). Results show that the spectra obtained using the MasSpec Pen were able determine whether the meat was sourced from a grass-fed or grain-fed animal with a high level of accuracy.

To test performance of the integrated system for tissue diagnosis, 12 human ovarian tissue samples including 7 normal tissues and 5 high grade serous carcinoma (HGSC) were analyzed following the workflow described above. A statistical classifier previously built for ovarian cancer diagnosis was incorporated in the software and analysis was triggered using foot pedal activation. For larger-sized tissue specimens, several regions within the same tissue sample were analyzed, yielding a total of 24 analyses. The mass spectra obtained presented characteristic lipid profiles similar to those we have previously described for normal and cancer ovarian tissues (FIG. 21). Using the software and statistical classifier, a cancer probability and associated predictive diagnosis were reported for each region analyzed.

Based on the cut-off values generated through the statistical classifier, samples with a predictive probability greater than 0.51 were as "cancer", while samples with predictive probabilities lower than 0.51 were called "normal". As shown in Table 7, 100% sensitivity for cancer diagnosis was achieved, as all of the regions of the five cancer samples analyzed were classified as cancer. One of the seven normal tissue samples (ON_164b) was misclassified as cancer in both regions analyzed, while one of the four regions analyzed of sample ON_135a was classified as cancer, yielding 80% selectivity. Overall, an 87.5% agreement between the predictive and pathologic diagnoses was achieved.

Lastly, the laparoscopic MasSpec Pen was tested using a laparoscopic simulation mannequin. The laparoscopic MasSpec Pen was inserted into the mannequin through an 8 mm cannula. Inside the mannequin, laparoscopic forceps were used to manipulate the MasSpec Pen, while a video camera was employed to transmit an image and/or video of the organs inside the abdomen and guide placement of the laparoscopic MasSpec pen during the procedure (FIG. 19B). Normal and cancer human ovarian samples were placed on top of a mimic organ and accessed through the laparoscopic incisions inside the mannequin, and then analyzed using the laparoscopic equipment. Forceps were used to grasp the engineered fin and correctly guide the pen to the tissue surface for analysis. Using the foot pedal, the analysis was automatically activated, as previously described. A predictive diagnosis of "normal" was achieved for the normal ovarian tissue (probability of cancer=0.37), while a predictive diagnosis of "cancer" was achieved for the ovarian cancer tissue (probability of cancer=0.68), which agrees with the histopathologic diagnosis of the samples. Overall, the laparoscopic MasSpec Pen showed robust performance in the simulated mannequin suggesting its compatibility for use in MIS procedures.

TABLE 5

Cosine similarity results between the mass spectra obtained using the laparoscopic MasSpec Pen (2.7 mm reservoir diameter) and different tubing lengths.

| | Tubing Length | |
|---|---|---|
| | 1.5 meters (n = 4) | 3.0 meters (n = 4) |
| 3.0 meters (n = 4) | 0.91 | — |
| 4.5 meters (n = 4) | 0.92 | 0.97 |

TABLE 6

Droplet transport time from pen tip to mass spectrometer through various tubing lengths.

| | Droplet Transport Time | |
|---|---|---|
| | Average (n = 10) | Relative Standard Deviation (RSD) |
| 1.5 meters | 3.8 | 12.4% |
| 3.0 meters | 5.8 | 11.5% |
| 4.5 meters | 7.5 | 5.2% |

TABLE 7

Pathologic diagnosis, software predictive diagnosis and cancer probabilities for the human ovarian tissue samples analyzed using the laparoscopic MasSpec Pen (2.7 mm reservoir diameter and 4.5 m tubing length).

| Pathologic Diagnosis | Tissue ID | | Software Predictive Diagnosis | Cancer Probability |
|---|---|---|---|---|
| Normal Ovary | ON_135a | Spot 1 | Cancer | 0.59 |
| | | Spot 2 | Normal | 0.40 |
| | | Spot 3 | Normal | 0.32 |
| | | Spot 4 | Normal | 0.01 |
| | ON_263c | Spot 1 | Normal | 0.39 |
| | | Spot 2 | Normal | 0.42 |

TABLE 7-continued

Pathologic diagnosis, software predictive diagnosis
and cancer probabilities for the human ovarian tissue
samples analyzed using the laparoscopic MasSpec Pen
(2.7 mm reservoir diameter and 4.5 m tubing length).

| Pathologic Diagnosis | Tissue ID | | Software Predictive Diagnosis | Cancer Probability |
|---|---|---|---|---|
| | ON_294a | Spot 1 | Normal | 0.04 |
| | ON_220a | Spot 1 | Normal | 0.11 |
| | | Spot 2 | Normal | 0.38 |
| | ON_164b | Spot 1 | Cancer | 0.76 |
| | | Spot 2 | Cancer | 0.62 |
| | ON_335c | Spot 1 | Normal | 0.00 |
| | | Spot 2 | Normal | 0.00 |
| | ON_161a | Spot 1 | Normal | 0.38 |
| | | Spot 2 | Normal | 0.36 |
| High Grade Serous Ovarian Cancer | OT_403a | Spot 1 | Cancer | 0.88 |
| | | Spot 2 | Cancer | 0.98 |
| | OT_054a | Spot 1 | Cancer | 0.98 |
| | | Spot 2 | Cancer | 0.72 |
| | OT_337a | Spot 1 | Cancer | 0.89 |
| | | Spot 2 | Cancer | 1.00 |
| | OT_405a | Spot 1 | Cancer | 0.99 |
| | | Spot 2 | Cancer | 0.99 |
| | OT_058a | Spot 1 | Cancer | 0.93 |

In conclusion, the laparoscopic MasSpec Pen is an automated device that provides near real time diagnostic information for MIS. The unique design and features of laparoscopic MasSpec Pen described meet many of the requirements needed for manual and robotic MIS. When compared to the handheld version, similar molecular patterns were obtained from mouse brain tissue sections. Different pen tip diameters and tube lengths were also tested for various clinical needs. Finally, a customized lab-built software was developed, providing a fully automated workflow for tissue analysis and diagnostic feedback. This technology may be a complementary tool for MIS, which could expedite clinical workflow and improve surgical outcomes.

Example 4—Materials and Methods

Laparoscopic MasSpec Pen Design. Three different laparoscopic/robotic MasSpec Pen tips were created from PDMS with diameters of 1.5 mm, 2.7 mm, and 4.0 mm. Grasping fins were built-in unilaterally in order to minimize overall cross section. Two micro-PTFE tubings (OD 0.794 mm, ID 0.339 mm) were grafted to the interior of the PDMS tip near the distal end. The micro-PTFE tubing was terminated 2 millimeters above the reservoir in order to avoid tissue interaction. The PDMS mixing solution from Dow Corning (Midland, Mich.) was molded into negative prints created by a Stratasys uPrint SE Plus 3D Printer (Eden Prairie, Minn., USA). PTFE tubing was purchased from Sigma-Aldrich (St. Louis, Mo., USA), and silicone tubing was purchased from Saint Gobain (Tygon #3550, Malvern, Pa., USA). This design allows the formation of a water droplet at the distal end of the PDMS tip that interacts with tissue to extract cellular lipids and small metabolites via phase diffusion. This entire system was inserted into a laparoscopic simulation mannequin through a 10 mm HiCap 30107 H5 trocar by Karl Storz, (Tuttlingen, Germany). Images were taken with a wireless endoscope IP67 snake camera in the simulation mannequin.

Tissue Samples. Human tissues were obtained from the Cooperative Human Tissue Network (CHTN) (Charlottesville, Va.) under approved Institutional Review Board protocol. Mouse brains were obtained from BioIVT (Westbury, N.Y., USA). Tissue samples were thawed to room temperature before analysis.

Mass Spectrometry Analysis. Experiments were performed on a Q Exactive™ Hybrid Quadrupole-Orbitrap™ mass spectrometer (Thermo Fisher Scientific, San Jose, Calif., USA). HPLC grade water was used for analysis. Full scan mode was carried out at the range of m/z 120 to 1800, at a resolving power of 140,000, capillary temperature was set to 350° C., and an S-lens radio frequency level was set to 100.

Statistical Analysis and Software Tools. The statistical analysis procedure for generating the statistical model using Lasso was explained in a previous work. The lab-built desktop software designed to predict and display a diagnosis in real time. Following activation by the pedal through the Arduino microcontroller, data from the mass spectrometer is continuously read using MSFileReader (Thermo Fisher Scientific) and the MSFileReader-Python-bindings package open-sourced on GitHub. The three consecutive mass spectra of highest intensity for selected ions are averaged and pre-processed for statistical prediction. Then, using the previously fitted Lasso model, a prediction is generated and displayed back to the user via the GUI.

Example 5—Characterizing Materials Using the MasSpec Pen

The MasSpec pen was also used to obtain samples from various materials to further evaluate the use of the pen is characterizing materials in the environment such a foods and forensic samples. Results demonstrated a wide range of further application for the mass spectroscopy analyses of the embodiments. For example, studies presented in FIGS. 22-25 and 30 demonstrated effect spectra could be produced from a wide range of food products including meats, fish and fruits. These spectra could be used to accurately characterize the source material for the samples, such the type of meat or fish that was being assessed. For these studies, meat and fish (salmon, trout, atlantic cod, and pollack) samples were obtained from a local supermarket (Central Market, Austin, Tex. Samples were stored in a fridge (4° C.) until analysis at room temperature. Analysis was performed using LTQ Orbitrap XL mass spectrometer (Thermo Scientific) coupled to the MasSpec Pen. Analyzed regions of the samples were marked to prevent duplicated analysis. Molecular profiles of each sample were collected and used to create a classification model with the least absolute shrinkage and selection operator (Lasso). Lasso was used to identify predictive markers of meat type and build a classification models for identification of unknown samples.

Figure 24:
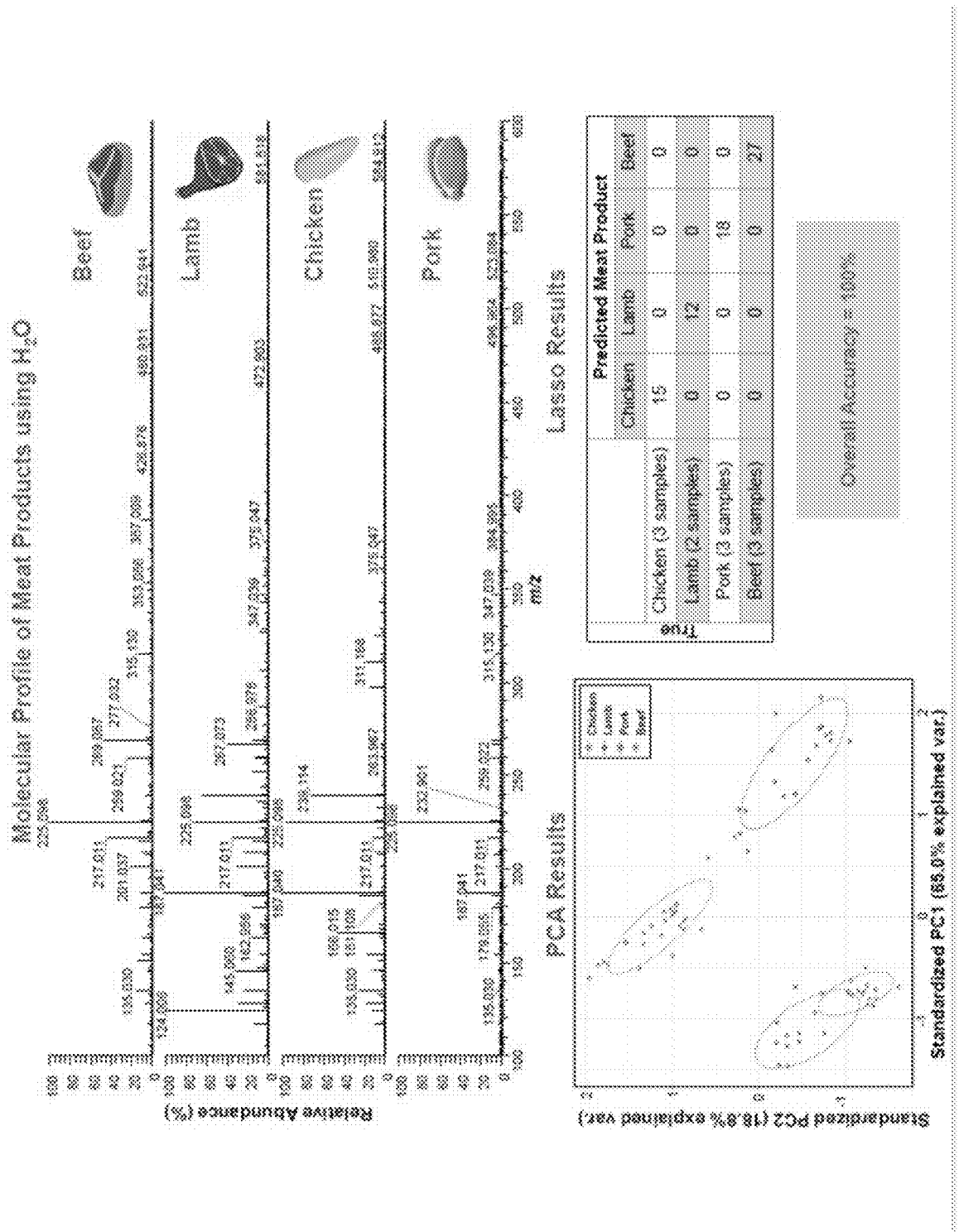
FIG. 24: Representative mass spectra obtained with the MasSpec Pen from samples of beef, lamb, chicken and pork using water as the solvent. Results show that the spectra obtained using the MasSpec Pen were able to assess the source of the meat with a high level of accuracy even when using water as the only solvent.
Figure 25:
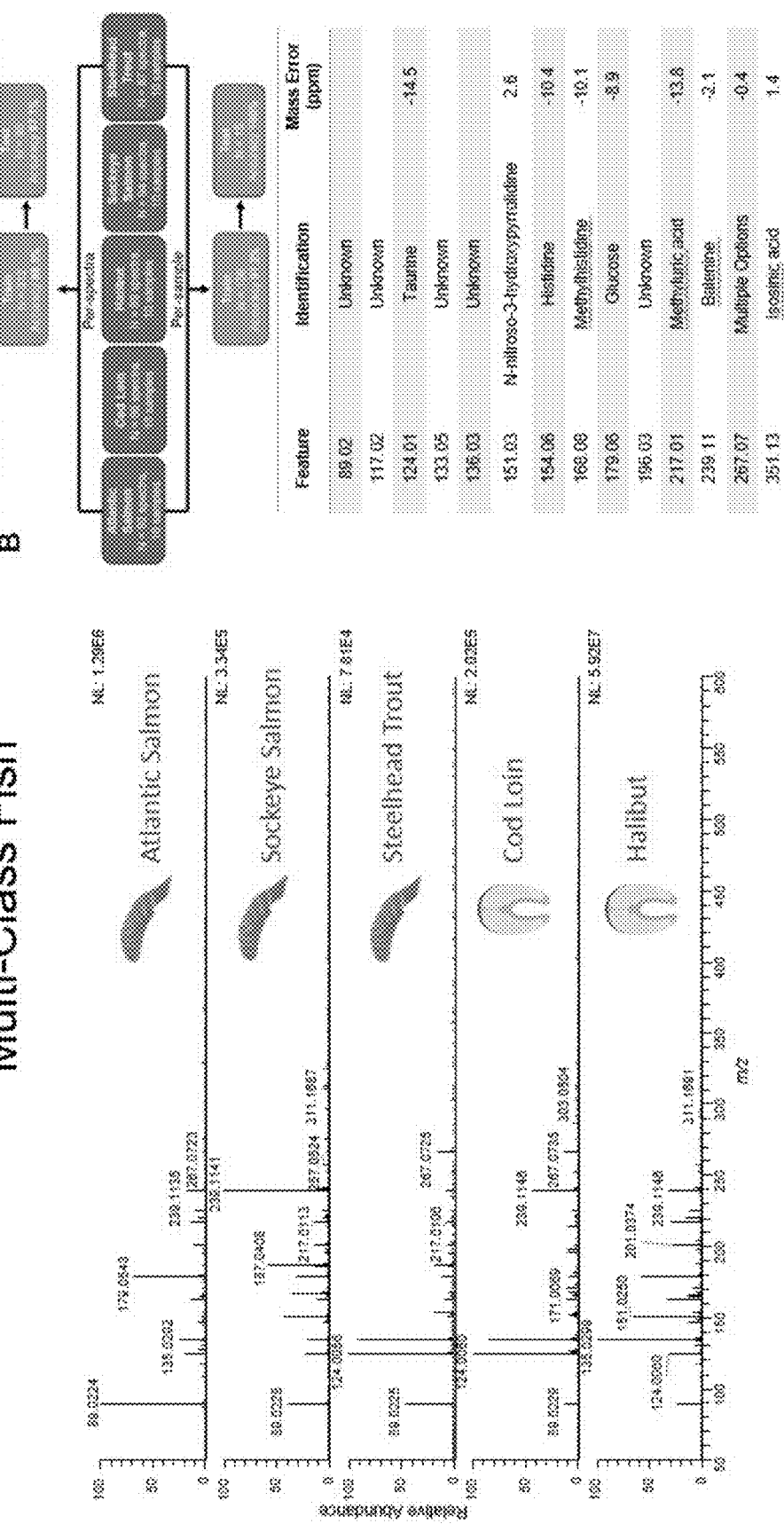
FIG. 25: Representative mass spectra obtained with the MasSpec Pen from samples of fish, including Atlantic salmon, sockeye salmon, steelhead trout, cod loin or halibut (using ACN:DMF (1:1) as a solvent). Results show that the spectra obtained using the MasSpec Pen were able to assess the source of the fish with a high level of accuracy.

The MasSpec Pen was used to analyze meat samples as well as 5 samples of each type of fish. Initial experiments were performed to optimize parameters of the MasSpec Pen for the highest lipid extraction and transmission. In the negative ion mode, detection of various glycerophospholipid species (GP), such as glycerophosphoinositols, glycerophosphoserines, and glycerophosphoethanolamines was achieved. In addition to GP, small metabolites, sphingolipids (SP), such as ceramides, and free fatty acids (FA), such as arachidonic acid and oleic acid were also observed. Despite the mass spectra complexity, the profiles obtained demonstrated trends in ion abundances characteristic of each meat sample. Statistical analysis was then applied to identify predictive markers of each meat type, as well as to build and evaluate the performance of classification models for prediction of meat type. These analysis demonstrated a high degree of accuracy in correctly identifying source meat samples. In fact, the methods were sensitive enough to even discern between grass-and grain-raised meat products (FIG. 24). Accordingly, methods of the embodiments could be used to authenticate consumer products such as meats and fish, which would otherwise be difficult to accurately and quickly authenticate.

Figure 26:
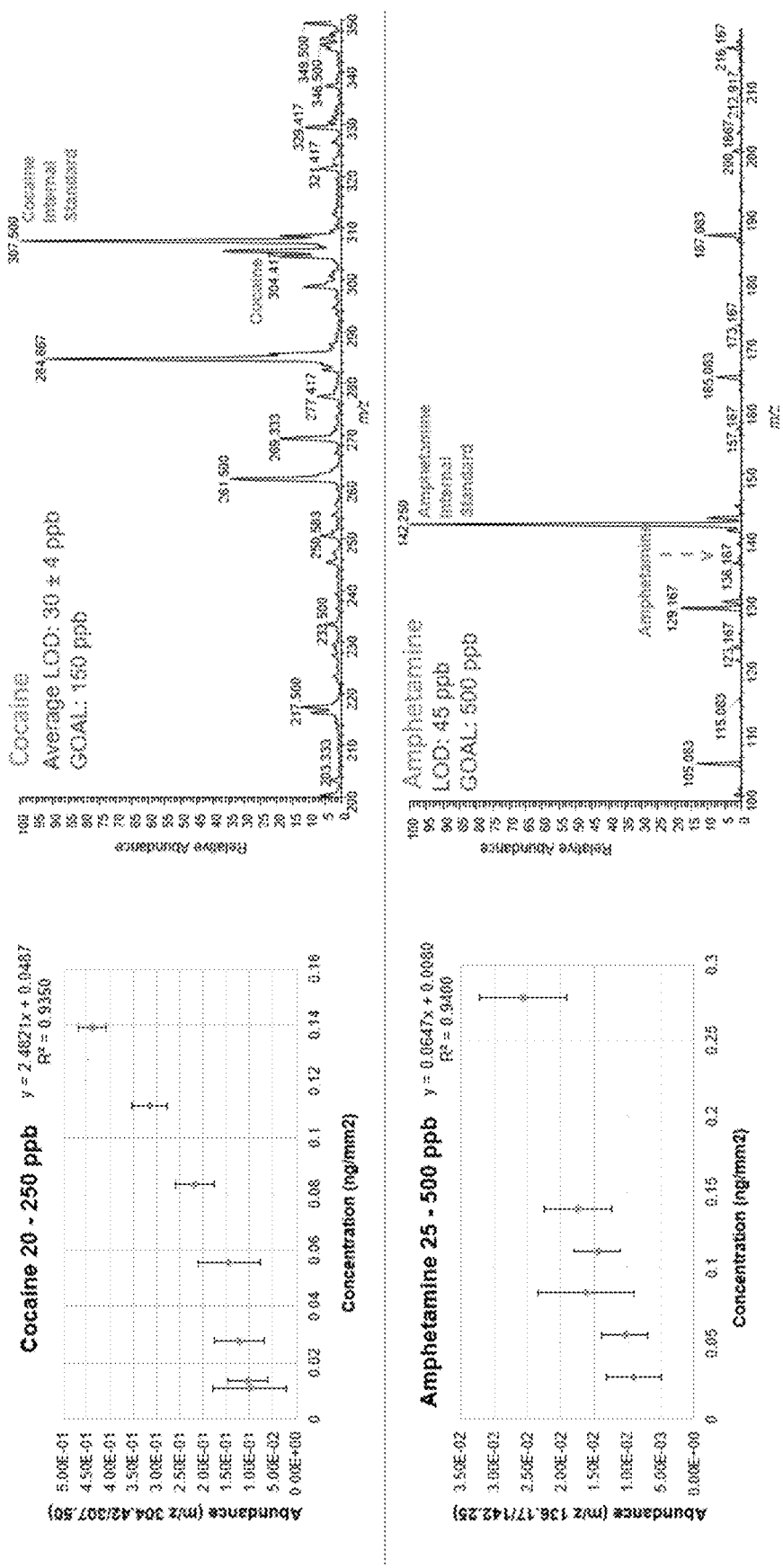
FIG. 26: Representative mass spectra obtained with the MasSpec Pen from samples including amounts of illicit drugs, cocaine and amphetamine. Results show that the spectra obtained using the MasSpec Pen were able to detect the drugs with a high degree of sensitivity and quantify the amount of drug in the sample.
Figure 27:
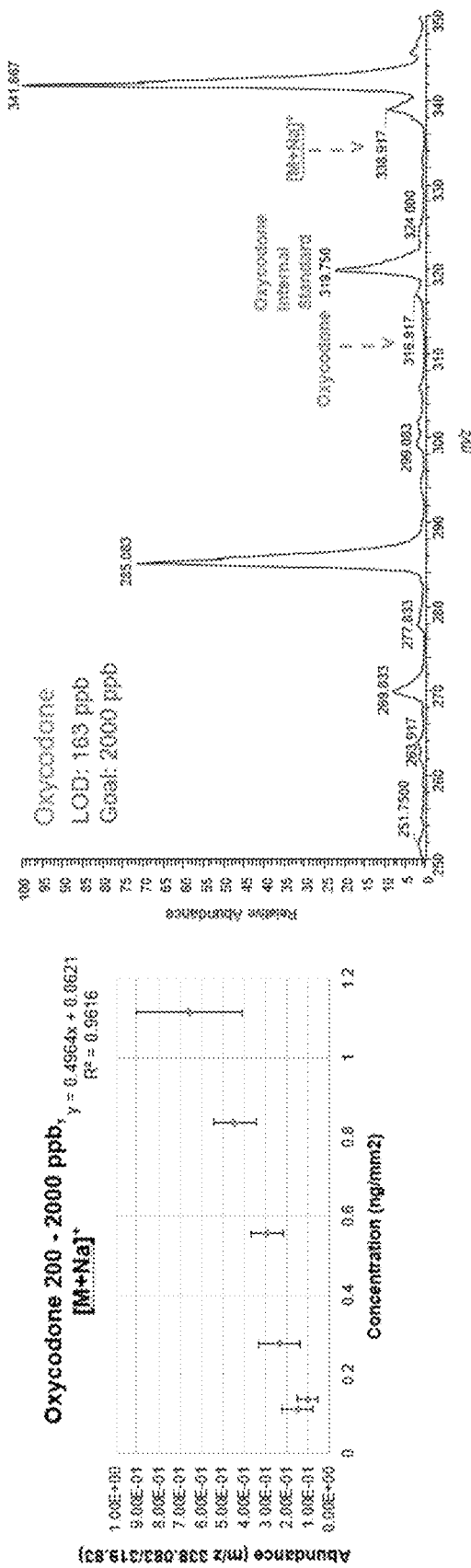
FIG. 27: Representative mass spectra obtained with the MasSpec Pen from samples including amounts of oxycodone. Results show that the spectra obtained using the MasSpec Pen were able to detect and quantify the amount of oxycodone in the sample.
Figure 28:
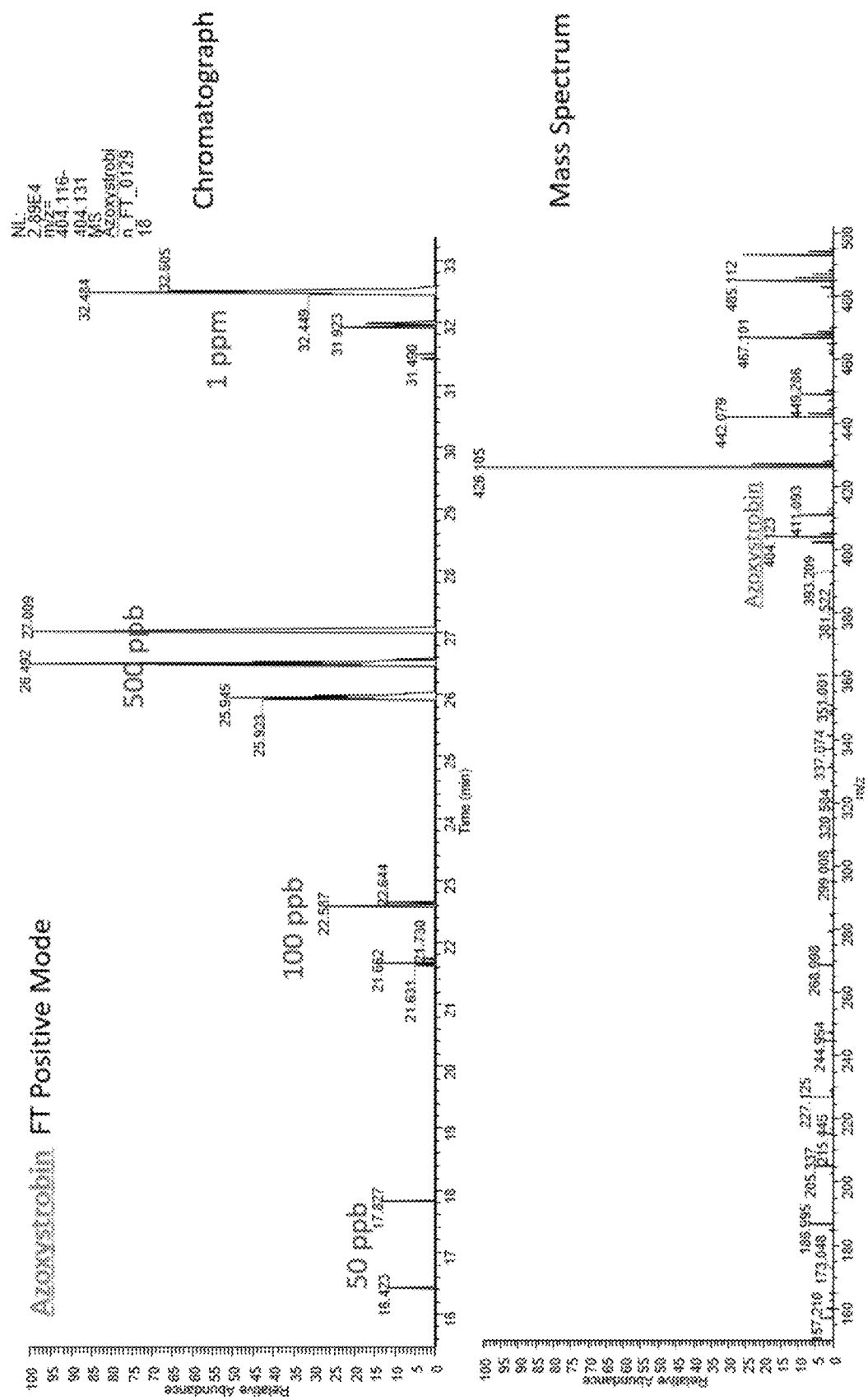
FIG. 28: Representative mass spectra (and a comparative chromatograph) obtained with the MasSpec Pen from samples including the pesticide azoxystrobin. Results show that the MasSpec Pen analysis was able to detect and quantify the amount of pesticide in the sample.
Figure 29:
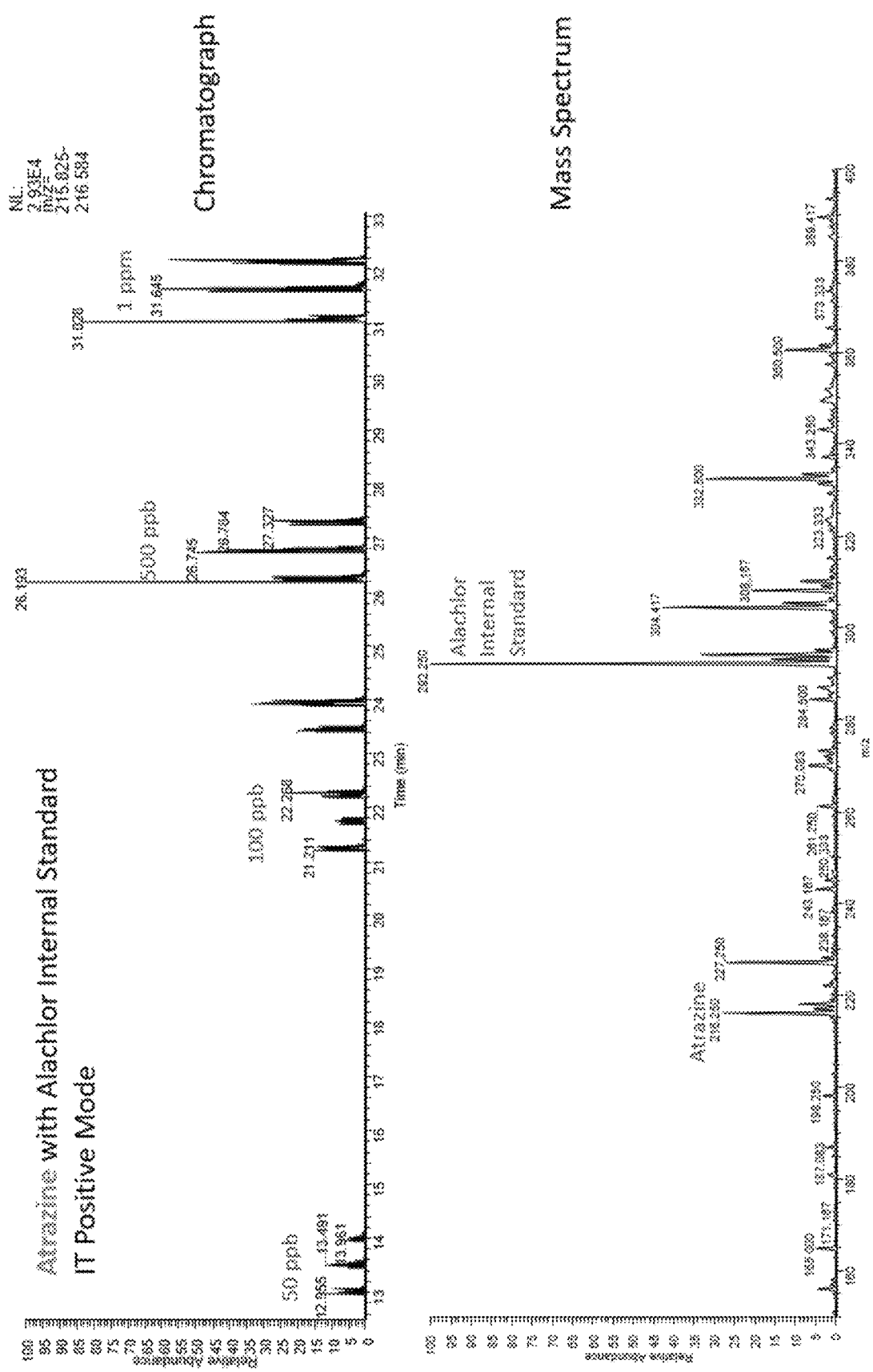
FIG. 29: Representative mass spectra (and a comparative chromatograph) obtained with the MasSpec Pen from samples including the pesticide atrazine. Results show that the MasSpec Pen analysis was able to detect and quantify the amount of pesticide in the sample.
Figure 30:
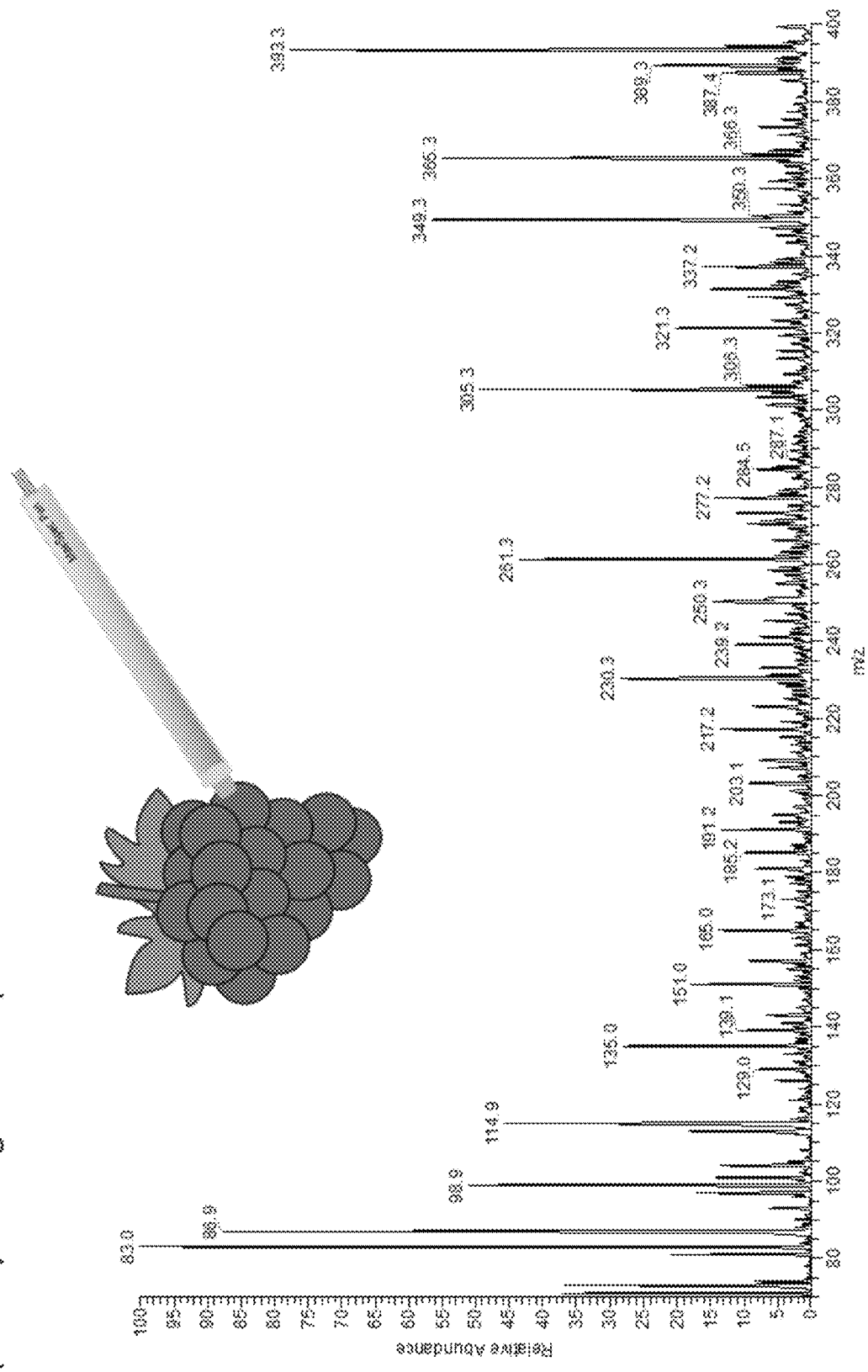
FIG. 30: Representative mass spectra obtained with the MasSpec Pen from grapes. Results show that the MasSpec Pen analysis was able to produce a spectrum that could be used to characterize the sample.

The methods likewise can be used to detect and quantify the amounts of compounds present in materials. For example, in the case of forensic samples, the amount of illicit drugs could be accurately determined using a sampling taken by the MasSpec Pen (see, FIGS. 26 and 27). Likewise, the methods have been shown to be effective in detecting the presence of pesticides in source materials (see, FIGS. 28-29). Thus, methods of the embodiments can be effectively applied to characterize a wide range of materials and the determine and quantify the presence of compounds of interest in the materials.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. An apparatus comprising:
   a chamber comprising a solvent;
   a mass spectrometer; and
   a probe comprising a reservoir, a first conduit, a second conduit and a third conduit, wherein:
   the probe is, or is comprised in, a cannula of a surgical instrument;
   the first conduit is in fluid communication with the chamber;
   the second conduit is in fluid communication with a gas supply; and
   the third conduit is in fluid communication with the mass spectrometer.

2. The apparatus of claim 1, wherein the surgical instrument is a laparoscope, a trocar needle, a biopsy guide, or a multiple-lumen catheter.

3. The apparatus of claim 1, wherein the reservoir is a space formed in said first, second or third conduits.

4. The apparatus of claim 3, wherein the reservoir is a space formed in said first conduit.

5. The apparatus of claim 1, wherein the reservoir comprises from 0.01 to 1.0 ml of fluid.

6. The apparatus of claim 1, wherein the surgical instrument comprises a fin that can be gripped.

7. The apparatus of claim 1, further comprising a fourth conduit, wherein: the first conduit, the second conduit and the third conduit are each in fluid communication with the fourth conduit.

8. The apparatus of claim 7, further comprising:
   a first valve configured to control flow between the first conduit and the fourth conduit; and
   a second valve configured to control flow between the second conduit and the fourth conduit.

9. The apparatus of claim 8, further comprising a third first valve configured to control flow between the third conduit and the fourth conduit.

10. The apparatus of claim 1, wherein the gas supply provides air from an atmosphere of the probe, nitrogen or carbon dioxide to the probe.

11. The apparatus of claim 1, wherein the probe comprises a tracking device or dye to track a location of the probe.

12. The apparatus of claim 1, further comprising a control system configured to control:
   a solvent flow from the chamber through the first conduit; and
   a sample flow through the third conduit to the mass spectrometer.

13. The apparatus of claim 1, wherein the mass spectrometer is in electronic communication with a computer that can provide sample analysis, and the computer provides a visual or auditory read-out of the sample analysis.

14. The apparatus of claim 1, further comprising a waste container in fluid communication with the third conduit.

15. The apparatus of claim 1, further comprising a pump in fluid communication with the third conduit.

16. The apparatus of claim 1, further comprising a heating element coupled to the third conduit.

17. The apparatus of claim 1, further comprising an ionization device in fluid communication with the third conduit.

18. The apparatus of claim 1, wherein the third conduit is not directly coupled to the mass spectrometer.

19. The apparatus of claim 1, further comprising a venturi device in fluid communication with the third conduit.

20. A method for assessing tissue samples from a subject, the method comprising:
   (a) applying a fixed or discrete volume of a solvent to a tissue site in the subject through a cannula of a surgical instrument via a probe;
      wherein the probe is, or is comprised in, the cannula of the surgical instrument;
      wherein the probe comprises a reservoir, a first conduit, a second conduit, and a third conduit, wherein:
         the first conduit is in fluid communication with a chamber comprising the solvent;
         the second conduit is in fluid communication with a gas supply; and
         the third conduit is in fluid communication with a mass spectrometer;
   (b) collecting the applied solvent with the probe to obtain a liquid sample; and
   (c) subjecting the sample to mass spectrometry analysis using the mass spectrometer.

* * * * *